United States Patent
Lu

(10) Patent No.: US 10,463,662 B2
(45) Date of Patent: Nov. 5, 2019

(54) NON-PLATINUM-BASED ANTI-CANCER COMPOUNDS FOR USE IN TARGETED CHEMOTHERAPY

(71) Applicant: Qing-Bin Lu, Waterloo (CA)

(72) Inventor: Qing-Bin Lu, Waterloo (CA)

(*) Notice: Subject to any disclaimer, the term of this patent is extended or adjusted under 35 U.S.C. 154(b) by 0 days.

(21) Appl. No.: 15/028,169

(22) PCT Filed: Oct. 8, 2014

(86) PCT No.: PCT/CA2014/050974
§ 371 (c)(1),
(2) Date: Apr. 8, 2016

(87) PCT Pub. No.: WO2015/051458
PCT Pub. Date: Apr. 16, 2015

(65) Prior Publication Data
US 2016/0235743 A1    Aug. 18, 2016

Related U.S. Application Data

(60) Provisional application No. 61/887,988, filed on Oct. 8, 2013.

(51) Int. Cl.
*A61K 31/44* (2006.01)
*A61K 31/4965* (2006.01)
(Continued)

(52) U.S. Cl.
CPC ........ *A61K 31/4965* (2013.01); *A61K 31/136* (2013.01); *A61K 31/44* (2013.01);
(Continued)

(58) Field of Classification Search
CPC ... A61K 31/44; A61K 31/495; A61K 31/4965
(Continued)

(56) References Cited

U.S. PATENT DOCUMENTS

2003/0219440 A1* 11/2003 Tobia ............... A61K 8/44
424/146.1
2006/0089316 A1* 4/2006 Brown ............... A61K 31/415
514/23

FOREIGN PATENT DOCUMENTS

DK    2008/01600 L    5/2010
WO    2006/088920 A1  8/2006
(Continued)

OTHER PUBLICATIONS

D'Addario et al, Journal of Clinical Oncology, vol. 23 (13), published May 1, 2005, pp. 2926-2936.*
(Continued)

*Primary Examiner* — Craig D Ricci
*Assistant Examiner* — Janet L. Coppins
(74) *Attorney, Agent, or Firm* — The Dobrusin Law Firm, PC

(57) ABSTRACT

Disclosed herein are non-platinum-based (NPB) anti-cancer compounds useful for targeted chemotherapy, e.g., to generate anti-cancer effects for the treatment of cancer and other disorders while having no or minimal toxicity. The compounds N have the general formula I: (I) wherein A represents an aromatic core; at least one of $R^a$ and $R^b$ is an electron transfer promoter as defined herein, e.g., $NH_2$; and at least one of $R^c$ is a leaving group as defined herein, e.g., halogen; and the remainder of the molecule is as defined herein. Pharmaceutical compositions, methods, uses, kits and commercial packages comprising the anti-cancer compounds are also disclosed.

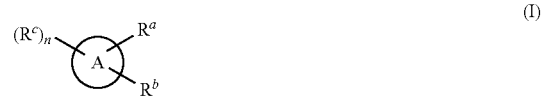

15 Claims, 32 Drawing Sheets

(51) Int. Cl.
  A61K 31/136   (2006.01)
  A61K 31/495   (2006.01)
  C07D 213/73   (2006.01)
  C07C 211/52   (2006.01)
  C07D 241/20   (2006.01)

(52) U.S. Cl.
  CPC .......... *A61K 31/495* (2013.01); *C07C 211/52* (2013.01); *C07D 213/73* (2013.01); *C07D 241/20* (2013.01)

(58) Field of Classification Search
  USPC ........................................................ 514/255
  See application file for complete search history.

(56) References Cited

FOREIGN PATENT DOCUMENTS

| WO | WO 2006088920 A1 * | 8/2006 | ........... C07D 211/58 |
|---|---|---|---|
| WO | WO-2006088920 A1 * | 8/2006 | ........... C07D 211/58 |
| WO | 2014/094178 A1 | 6/2014 | |

OTHER PUBLICATIONS

Kang et al, World Journal of Gastroenterology, published May 14, 2014, vol. 20 (18), pp. 5396-5402.*
Ben-Ari, Journal of the NCI (2004), vol. 96(8), pp. 577-579.*
Ben-Ari, Journal of the NCI (2004), vol. 96(8), pp. 577-579. (Year: 2004).*
Anderson, Chem & Biology (2003), vol. 10, pp. 787-797. (Year: 2003).*
Kopf-Maier and Kopf, Chem Reviews (1987), vol. 87, pp. 1137-1152. (Year: 1987).*
Thiel, Nature Biotech (2004), vol. 22(5), pp. 513-519. (Year: 2004).*
Ahmed et al., *Molecular modeling and synthesis of certain substituted aryl compounds which have a potential anticancer activity*, Bulletin of Faculty of Pharmacy, Cairo University, vol. 49, No. 1, pp. 25-36, Aug. 26, 2011. ISSN: 1110-0931.
Godemann et al., *Fragment-Based Discovery of BACEI Inhibitors Using Functional Assays*, Biochemistry, vol. 48, No. 45, pp. 10743-10751, Nov. 17, 2009. ISSN: 0006-2960.
P. G. Rose, B. N. Bundy, E. B. Watkins, J. T. Thigpen, G. Deppe, M.A. Maiman, D. L. Clarke-Pearson , S. Insalaco. Concurrent cisplatin-based radiotherapy and chemotherapy for locally advanced cervical cancer. N. Engl. J. Med. 340, 1144-53(1999).
D. M. Reese, Anticancer drugs, Nature 378, 532 (1995).
H. Varmus, The New Era in Cancer Research. Science 312, 1162 (2006).
B. Alberts, The Promise of Cancer Research, Science 320, 19 (2008).
B. Alberts, The Challenge of Cancer. Science 331, 1491 (2011).
A. H. Zewail, Femtochemistry: Atomic-Scale Dynamics of the Chemical bond using ultrafast lasers (Nobel Lecture).Angew. Chem. Int. Ed. 39,2587-2631 (2000).
Q.-B. Lu, Effects of Ultrashort-Lived Prehydrated Electrons in Radiation Biology and Their Applications for Radiotherapy of Cancer. Mutat. Res. :Rev. Mutat. Res. 704, 190-199 (2010).
L.Y. Lu, N. Ou, & Q.-B. Lu, Antioxidant induces DNA Damage, Cell Death and Mutagenicity in Human Lung and Skin Normal Cells. Sci. Rep. 3, 3169(1-11) (2013).
Q.-B. Lu, Molecular Reaction Mechanisms of Combination Treatments of Low-Dose Cisplatin with Radiotherapy and Photodynamic Therapy, J. Med. Chem. 50, 2601-2604 (2007).
Q.-B. Lu, S. Kalantari, & C.-R. Wang, Electron Transfer Reaction Mechanism of Cisplatin with DNA at the Molecular Level. Mol. Pharmaceutics 4, 624-628 (2007).
M.D. Prados et al. "A phase 3 randomized study of radiotherapy plus procarbazine, CCNU, and vincristine (PCV) with or without BUdR for the treatment of anaplastic astrocytoma: a preliminary report of RTOG 9404", Int. J. Radiat. Oneal. Bioi. Phys. 45, 1109(1999).
A. Choudhury et al., Targeting homologous recombination using imatinib results in enhanced tumor cell chemosensitivity and radiosensitivity, Mol Cancer Ther 8, 203-213 (2009).
International Search Report and Written Opinion from the Canadian Intellectual Property Office for Application No. PCT/CA2014/050974, dated Dec. 24, 2014.
International Preliminary Report on Patentability from The International Bureau of WIPO for Application No. PCT/CA2014/050974, dated Apr. 12, 2016.
Murata, M., et al., Oxidative DNA damage induced by hair dye components ortho-phenylenediamines and the enhancement by superoxide dismutase, Mutation Research, Genetic Toxicology and Environmental Mutagenesis, Elsevier, Amsterdam, NL, Sep. 5, 2006, p. 184-191, vol. 607, No. 2.
Kidani, Y, et al., Synthesis of Platinum (II) Complexes of 4-Substituted o-Phenylenediamine Derivatives and Determination of their Antitutmor Activity, Chem. Pharm. Bull., 1979, p. 2577-2581, vol. 27, No. 11.

* cited by examiner

| Toxicity Test Results | | |
|---|---|---|
| Hepatotoxicity | | |
|  | 0mg/kg | 7mg/kg |
| ALP | 68 (+/-4)U/L | 67 (+/-11)U/L |
| ALT | 132(+/-64)U/L | 172 (+/-88)U/L |
| TBIL | 1 (+/-0) umol/L | 1 (+/-0)umol/L |
| Nephrotoxicity | | |
|  | 0mg/kg | 7mg/kg |
| Creatinine | 6 (+/-1)umol/L | 7(+/-1)umol/L |
| Urea | 6.9 (+/-2.1)mmol/L | 6.0(+/-1.1) mmol/L |
| Electrolytes | | |
|  | 0mg/kg | 7mg/kg |
| Chloride | 111.7 (+/-1.5)mmol/L | 110 (+/-3.0)mmol/L |
| Potassium | 6.3 (+/-0.3)mmol/L | 8.4 (+/-3.6)mmol/L |
| Sodium | 148.7 (+/-1.2)mmol/L | 144.7 (+/-4.5)mmol/L |

NON-PLATINUM-BASED ANTI-CANCER COMPOUNDS FOR USE IN TARGETED CHEMOTHERAPY

CROSS-REFERENCE TO RELATED APPLICATIONS

This application claims the benefit of priority of U.S. Provisional Patent Application No. 61/887,988, filed Oct. 8, 2013, which is incorporated herein by reference in its entirety.

BACKGROUND

Cancer is a major health problem across the globe and the conquest of cancer poses great challenges to medical science. Chemotherapy is one of the major modalities for cancer therapy and generally refers to the treatment of cancer with the use of one or more anti-cancer agents (chemotherapeutic agents). Some chemotherapeutic agents are also used to treat other diseases and conditions, such as arthritis, systemic lupus erythematosus, AL amyloidosis, ankylosing spondylitis, multiple sclerosis, Crohn's disease, psoriasis, and scleroderma.

Many anti-cancer agents act by impairing mitosis and thereby target rapidly-dividing cells, a hallmark property of most cancer cells. Some agents stop the cells from dividing and others kill the cells, e.g. by triggering apoptosis. Certain newer agents (e.g., various monoclonal antibodies) are being developed to provide a more targeted therapy (as distinct from traditional chemotherapy), for example, those targeting specific proteins that are over expressed in certain types of cancer cells and essential for their growth. Such treatments are often used in combination with traditional chemotherapeutic agents in antineoplastic treatment regimens.

Chemotherapy may employ one anti-cancer agent at a time (single-agent chemotherapy or mono-chemotherapy) or multiple agents at once (combination chemotherapy). Chemical agents that enhance the radiosensitivity of cancer to radiation therapy (ionizing radiation) are called radiosensitizers. Treatment using chemical substances (called photosensitizers) that convert to cytotoxic activity only upon exposure to light is called photodynamic therapy.

While a variety of anti-cancer agents are available, nearly all are toxic. Chemotherapy generally causes significant, and often dangerous, side effects, including kidney toxicity, liver toxicity, severe nausea and vomiting, bone marrow depression, myelosuppresion/immunosuppression, mucositis (inflammation of the lining of the digestive tract), alopecia (hair loss), cytopenia, pain and fatigue. Additional side-effects can include cachexia, cutaneous complications, such as hypersensitivity reactions, as well as neurological, pulmonary, cardiac, reproductive and endocrine complications. Side effects associated with anti-cancer agents are generally the major factor in defining a dose-limiting toxicity (DLT) for the agent. Managing the adverse side effects induced by chemotherapy is of major and critical importance in the clinical management of cancer treatment. In addition, many tumor cells are resistant, or develop resistance, to anti-cancer agents, e.g. through multi-drug resistance.

Cisplatin (cis-Pt(NH3)$_2$Cl$_2$) is a platinum-based antineoplastic drug and is one of the most widely used drugs for cancer treatment. Cisplatin has also been used as a radiosensitizer to enhance the radiosensitivity of cancer cells to ionizing radiation [Rose et al., 1999]. Despite its widespread use, cisplatin has two major drawbacks: severe toxic side effects and both intrinsic and acquired resistance. These drawbacks even led to a call for terminating the clinical applications of heavy-metal Pt-based anticancer drugs [Reese, 1995]. There remains a need to identify less toxic analogues that reduce cisplatin toxicity and/or prevent or overcome drug resistance.

Despite increasing costs to pharmaceutical companies, the number of truly innovative new medicines approved by the US Food and Drug Administration and other major regulatory bodies around the world has been decreasing over the past decade. The identification of new anti-cancer agents remains a somewhat empirical process, generally involving screening a large number of compounds in order to identify a very small number of potential candidate molecules for further investigation. Thus, there is a need for a more rational and efficient approach to the design of novel anti-cancer agents. While various drug discovery tools are available, such as binding-based screening, inhibitor-based screening and structure-based drug design, an outstanding problem has been lack of understanding of the precise molecular mechanisms of action of most anticancer drugs currently in use or in clinical trials. Without a specific mechanistic understanding, it is difficult to learn from the successes and failures of individual therapies. Thus, the search for new anticancer drugs by traditional methods has proven to be expensive, difficult and inefficient. There is a compelling need for innovative cancer research focusing on a much deeper understanding of fundamental mechanisms of DNA damage/repair, apoptosis, tumorigenesis, and therapy in molecular terms in order to ultimately conquer cancer [Varmus, 2006; Alberts, 2008, 2011], which in turn will enable breakthroughs in cancer therapy.

Direct observation of molecular reactions is of great importance in diverse fields from chemistry and biology to medicine. Femtosecond (fs) (1 fs=$10^{-15}$ s) time-resolved laser spectroscopy (fs-TRLS) is a direct technique to visualize molecular reactions in real time. Its key strength lies in short duration laser flashes of a time scale at which many molecular reactions truly occur. Its application to chemical and biological systems gave birth to new fields of femtochemistry and femtobiology [Zewail, 2000].

Over the past decade, the inventor has coined an emerging transdisciplinary frontier, femtomedicine (FMD), which involves a fusion of ultrafast laser techniques with biomedical sciences to advance fundamental understanding and therapies of major human diseases [Lu, 2010]. Indeed, femtomedicine holds the promise of accelerating discovery and new advances in therapies of major human diseases, notably cancer.

FMD studies by the inventor have led to the discoveries of a reductive damaging mechanism in the cell, which may be closely related to human diseases notably cancer [Lu et al., 2013], and a dissociative electron transfer (DET) reaction mechanism of cisplatin as both an anti-cancer drug and a radiosensitizer in combination with radiotherapy [Lu, 2007; Lu et al., 2007; Lu, 2010]. These mechanistic understandings provide opportunities to improve the therapies of existing drugs and to develop new effective drugs.

PCT/CA2013/051005 (to the present inventor), entitled Radiosensitizer Compounds for Use in Combination With Radiation, discloses a class of non-platinum based compounds in combination with radiation therapy, using ionizing radiation, to enhance the anti-cancer efficacy of radiotherapy. The compounds were shown to enhance the radiosensitivity of cancer cells to ionizing radiation (also see, Lu, 2014).

SUMMARY OF THE INVENTION

Generally, the present disclosure relates to a class of non-platinum-based anti-cancer compounds (abbreviated as NPBs hereafter) discovered through the femtomedicine approach. The compounds induce anti-cancer effects in vitro and in vivo and were found to have little to no toxicity to normal cells. The compounds can be used as anti-cancer agents in targeted chemotherapy since they have the ability to kill cancer cells while having minimal toxicity toward normal cells. Accordingly, the present disclosure also relates to a targeted chemotherapy for cancer and other conditions treatable by chemotherapy. Also disclosed herein are compositions, dosage forms, methods, uses, commercial packages and kits relating to the NPB compounds disclosed herein.

In one aspect, there is provided an NPB anti-cancer compound having the general formula I:

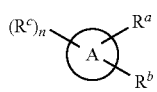
(I)

wherein A represents an aromatic core; at least one of $R^a$ and $R^b$ is an electron transfer promoter as defined herein; and at least one of $R^c$ is a leaving group as defined herein.

In one aspect, the NPB anti-cancer compound has the general formula I:

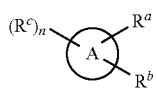
(I)

wherein A is a 5- or 6-membered aryl or heteroaryl ring containing 0-2 ring heteroatoms selected from the group consisting of N, O and S, the remaining ring atoms being carbon; $R^a$ and $R^b$ are, independently, H, OH, alkyl, alkoxy, alkenyl, alkynyl, cycloalkyl, cycloalkenyl, cycloalkynyl, aryl, heterocyclyl, heteroaryl or an electron transfer promoter, wherein at least one of $R^a$ and $R^b$ is an electron transfer promoter; $R^c$ is, independently for each occurrence, H, OH, alkyl, alkoxy, alkenyl, alkynyl, cycloalkyl, cycloalkenyl, cycloalkynyl, aryl, heterocyclyl, heteroaryl, or a leaving group, or two adjacent $R^c$ groups taken together with the ring atoms to which they are attached form a 5- or 6-membered saturated, partially saturated or unsaturated ring which contains 0-2 ring heteroatoms selected from N, O and S and which can be optionally substituted with 1-4 $R^d$; wherein at least one $R^c$ is a leaving group; $R^d$ is independently OH, alkyl, alkoxy, alkenyl, alkynyl, cycloalkyl, cycloalkenyl, cycloalkynyl, aryl, heterocyclyl or heteroaryl; and n=1-4, wherein each of the alkyl, alkoxy, alkenyl, alkynyl, cycloalkyl, cycloalkenyl, cycloalkynyl, aryl, heterocyclyl and heteroaryl moieties is optionally substituted; or a pharmaceutically acceptable salt thereof.

In another aspect, there is provided a NPB anti-cancer compound having the general formula II:

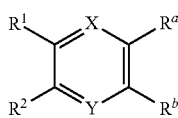
(II)

wherein: X and Y are independently C—$R^3$ or N; $R^3$ is H, OH, halogen, alkyl, alkoxy, alkenyl, alkynyl, cycloalkyl, cycloalkenyl, cycloalkynyl, aryl, heterocyclyl, or heteroaryl; $R^a$ and $R^b$ are, independently, H, OH, alkyl, alkoxy, alkenyl, alkynyl, cycloalkyl, cycloalkenyl, cycloalkynyl, aryl, heterocyclyl, heteroaryl or an electron transfer promoter, wherein at least one of $R^a$ and $R^c$ is an electron transfer promoter; $R^1$ and $R^2$ are, independently, H, OH, alkyl, alkoxy, alkenyl, alkynyl, cycloalkyl, cycloalkenyl, cycloalkynyl, aryl, heterocyclyl, heteroaryl, or a leaving group; wherein at least one of $R^1$ and $R^2$ is a leaving group, wherein each of the alkyl, alkoxy, alkenyl, alkynyl, cycloalkyl, cycloalkenyl, cycloalkynyl, aryl, heterocyclyl and heteroaryl moieties is optionally substituted; or a pharmaceutically acceptable salt thereof.

In another aspect, there is provided a NPB anti-cancer compound having the general formula III,

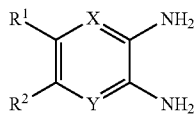
(III)

wherein X and Y are independently C—$R^3$ or N; $R^3$ is H, OH, halogen, alkyl, alkoxy, alkenyl, alkynyl, cycloalkyl, cycloalkenyl, cycloalkynyl, aryl, heterocyclyl, or heteroaryl; $R^1$ and $R^2$ are, independently, H, OH, alkyl, alkoxy, alkenyl, alkynyl, cycloalkyl, cycloalkenyl, cycloalkynyl, aryl, heterocyclyl, heteroaryl, or a leaving group; wherein at least one of $R^1$ and $R^2$ is a leaving group, wherein each of the alkyl, alkoxy, alkenyl, alkynyl, cycloalkyl, cycloalkenyl, cycloalkynyl, aryl, heterocyclyl and heteroaryl moieties is optionally substituted; or a pharmaceutically acceptable salt thereof.

In some embodiments of Formula I or II, each of $R^a$ and $R^b$ is an electron transfer promoter. In some embodiments described herein, the electron transfer promoter is selected from the group consisting of —$NH_2$, —NHR, —$NR_2$, —OH, —$NHCOCH_3$, —NHCOR, —$OCH_3$, and —OR. In some embodiments, the electron transfer promoter is —$NH_2$, —NHR, or —$NR_2$. In some embodiments, R is substituted or unsubstituted alkyl. In some embodiments, $R^a$ and $R^b$ are each electron transfer promoters. In some embodiments, $R^a$ and $R^b$ are on adjacent ring carbon atoms. In some embodiments, the electron transfer promoter is —$NH_2$.

In some embodiments, the leaving group is halogen. In some embodiments of Formula I, one or two $R^c$ groups on Ring A are halogen. In some embodiments of Formula I, two $R^c$ groups on Ring A are halogen. In some embodiments, the halogen is Cl, Br, I or F. In some embodiments, the halogen is Cl, Br or I.

In some embodiments of Formula I, Ring A is a 6-membered aryl or heteroaryl ring, such as, benzene, pyridine or pyrazine. In some embodiments Ring A is benzene.

In some embodiments of Formula I, Ring A is benzene, pyridine or pyrazine; each of $R^a$ and $R^b$ are $NH_2$; two $R^c$ substituents on Ring A are halogen each positioned meta to $R^a$ and $R^b$ on Ring A; and any remaining Re groups are as defined herein. In some embodiments, Ring A is benzene and, in some further embodiments, the remaining carbons on Ring A are unsubstituted carbon. In some embodiments, Ring A is pyridine and, in further embodiments, the remaining carbon on Ring A is unsubstituted. In some embodiments, Ring A is pyrazine.

In some embodiments of Formula II or III, $R^1$ and $R^2$ are both leaving groups, such as halogen. In some embodiments, each halogen is selected from the group consisting of Cl, Br, I or F.

In some embodiments of Formula II or III, X and Y are C—$R^3$. In some embodiments of Formula II or III, X is C—$R^3$ and Y is N. In some embodiments, $R^3$ is H, OH, halogen, alkyl, alkoxy, alkenyl, alkynyl, cycloalkyl, cycloalkenyl, cycloalkynyl, aryl, heterocyclyl, or heteroaryl. In some embodiments, where the ring carbon is unsubstituted, R is H. In some embodiments of Formula II or III, X and Y are each N.

In some embodiments, the NPB compound is a compound selected from the group consisting of:

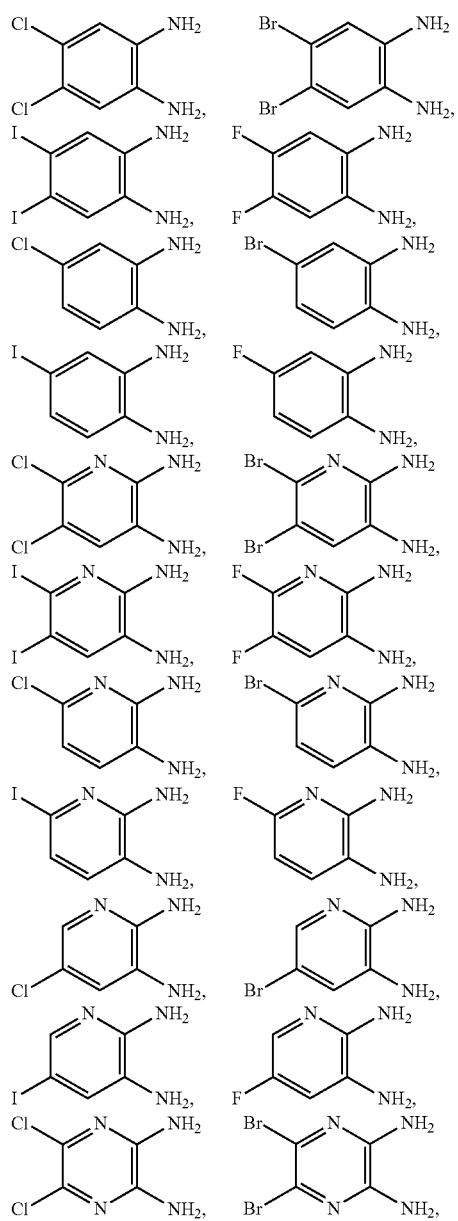

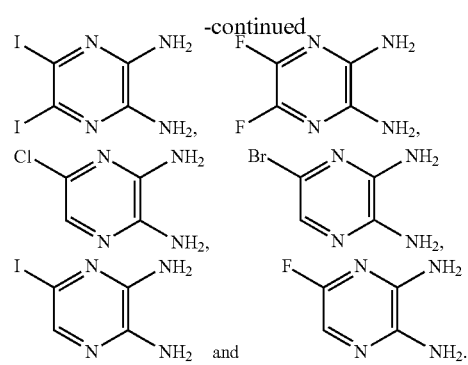

In some embodiments, the NPB compounds disclosed herein have an electron affinity greater than 0 eV. In some embodiments, the compounds disclosed herein have an electron affinity between about +0.0 eV to +5 eV. In some embodiments, the compounds disclosed herein have an electron affinity between about +0.5 eV and about +2.5 eV.

In another aspect, there are provided NPB compounds as defined herein for use in treating a cancer cell (e.g. to induce an anti-cancer effect in a cancer cell).

In another aspect, there are provided NPB compounds as defined herein for use for use in treating a disease or condition treatable by chemotherapy in a subject. The disease or condition may be a non-caner disease or condition.

In another aspect, there are provided NPB compounds as defined herein for use in the treatment of cancer in a subject. In some embodiments, the method may be for prevention, control, inhibition, or complete cure of cancer in a subject.

In another aspect, there are provided NPB compounds as defined herein for use in the manufacture of a medicament for the treatment of cancer in a subject.

In another aspect, there is provided a use of a NPB compound as defined herein to treat a disease or condition that is treatable by chemotherapy in a subject. In some cases, the disease or condition may be a non-cancer disease or condition such as those recited elsewhere herein. In some cases, the disease or condition is cancer.

In another aspect, there is provided a use of a NPB compound as defined herein in the treatment of cancer in a subject. In another aspect, there is provided a use of a NPB compound as defined herein in the manufacture of a medicament for the treatment of cancer in a subject.

In another aspect, there is provided a pharmaceutical composition for use in the treatment of cancer or another disease or condition treatable by chemotherapy, comprising: an effective amount of a NPB compound as defined herein; and a pharmaceutically acceptable carrier or diluent.

In another aspect, there is provided a targeted chemotherapy for cancer comprising a NPB compound as defined herein.

In another aspect, there is provided a method of treating cancer or another disease or condition treatable by chemotherapy in a subject in need thereof comprising: administering an effective amount of an anti-cancer compound as defined herein.

In another aspect, there is provided method of inducing an anti-cancer effect in a cancer cell, comprising: administering to the cancer cell an effective amount of a NPB compound as defined herein. In some embodiments, the anti-cancer effect is killing of the cancer cell. In some embodiments, the cancer cell is a tumour cell.

In another aspect, there is provided a method of inducing apoptosis in a cancer cell, comprising, administering to the cell an effective amount of a compound as defined herein.

In another aspect, there is provided a method of generating chemotherapeutic effects in a subject in need thereof comprising: administering an effective amount of a compound as defined herein.

In another aspect, there is provided a combination therapy for treating cancer or another disease treatable by chemotherapy comprising: administering an effective amount of a compound as defined as defined herein to the subject; and administering one or more additional therapeutic agents to the subject. In some embodiments, the therapeutic agent is a chemotherapeutic agent.

In another aspect, there is provided commercial package or kit comprising a NPB compound as defined herein; and instructions for use in chemotherapy.

In some embodiments of the methods, compounds, compositions, uses and kits described herein, the treatment excludes radiation. In other words, the compounds are used in the absence of radiation such that they are used as anti-cancer agents rather than radiosensitizers. This means that the subject is not receiving radiation treatment in a manner that would interact with the NPB anti-cancer activity. The subject may however receive radiation treatment at another time that does not interact with the compounds of the invention.

In some embodiments of the methods, compounds, compositions, uses and kits described herein, the cancer is sensitive to Pt-based anti-cancer drugs (e.g., cisplatin) or other anti-cancer drugs that have toxic side effects. In some embodiments, the cancer is resistant to Pt-based anti-cancer drugs (e.g., cisplatin) or other anti-cancer drugs that have toxic side effects.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached figures.

FIG. 32 shows in vivo toxicity of Compound B in mice. The hepatotoxicity (ALT, ALP, TBIL), nephrotoxicity (blood urea, creatinine), and electrolytes (Na, K, etc) were measured from the blood samples collected at the end of the treatment by 5 mg/kg Compound B daily for 5 days to show acute toxicity. ALP=Alkaline phosphatase, ALT=alanine aminotransferase, TBIL=total bilirubin. The results show no significant changes between the control group and the treated group, indicating no acute toxicity induced by Compound B.

DETAILED DESCRIPTION

Figure 1:
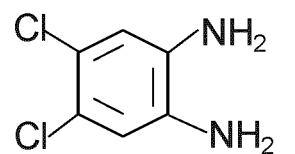
FIG. 1. Molecular structures of 12 exemplary NPB compounds: A: (4,5-)dichloro-(1,2-)diamino-benzene (4,5-dichloro-1,2-phenylenediamine); B: (4,5-)dibromo-(1,2-)diamino-benzene (4,5-dibromo-1,2-phenylenediamine); C: (4,5-)diiodo-(1,2-)diamino-benzene (4,5-diiodo-1,2-phenylenediamine); D: bromo-(1,2-)diamino-benzene; E: chloro-(1,2-)diamino-benzene; F: iodo-(1,2-)diamino-benzene; G: (4,5-)dichloro-(1,2-)diamino-pyrazine; H: (4,5-)dibromo-(1,2-)diamino-pyrazine; I: (4,5-)diiodo-(1,2-)diamino-pyrazine; J: bromo-(1,2-)diamino-pyrazine; K: chloro-(1,2-)diamino-pyrazine; L: iodo-(1,2-)diamino-pyrazine.
Figure 1:
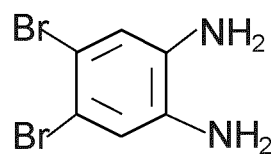
Figure 1:
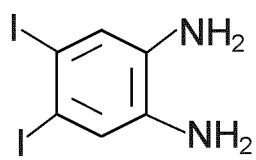
Figure 1:
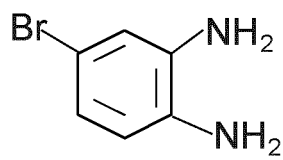
Figure 1:
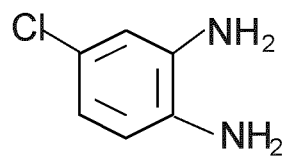
Figure 1:
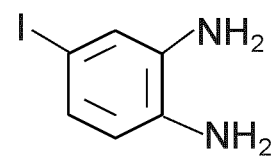
Figure 1:
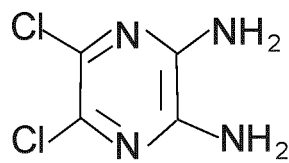
Figure 1:
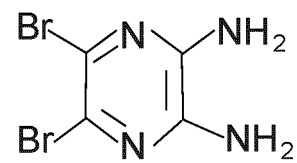
Figure 1:
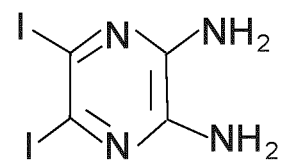
Figure 1:
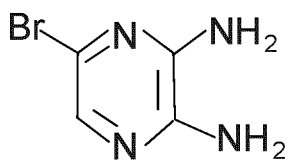
Figure 1:
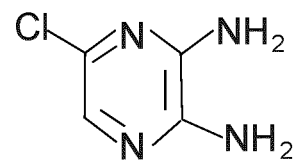
Figure 1:
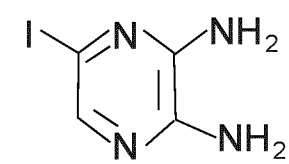

Generally, the present disclosure relates to a class of non-platinum-based (NPB) anti-cancer compounds discovered through the femtomedicine approach. The compounds induce anti-cancer effects in vitro and in vivo and were found to have little to no toxicity to normal cells. They were strikingly found to be much less toxic to normal cells than the platinum-containing anti-cancer drug, cisplatin, even at doses up to 200 µM. The compounds can be used as anti-cancer agents for targeted chemotherapy since they have the ability to kill cancer cells while having minimal toxicity toward normal cells. Accordingly, the present disclosure also relates to a targeted chemotherapy for cancer and other conditions treatable by chemotherapy. Also disclosed herein are compositions, dosage forms, methods, uses, commercial packages and kits relating to the NPB compounds disclosed herein.

Non-Platinum-Based (NPB) Anti-Cancer Compounds

The term "NPB compound" refers to a non-platinum-containing anti-cancer compound as defined herein that may be used to generate anti-cancer effects in vitro or in vivo, for example, in the treatment of cancer cells or in the treatment of cancer or other disorders treatable by chemotherapy. The compounds may essentially be thought of as cisplatin analogues without the platinum core. The terms "compound", "molecule" and "agent" may be used interchangeably herein.

The NPB compounds of the present disclosure are capable of generating the anti-cancer effects effect while having minimal toxicity. Without wishing to be bound by theory, the NPB compounds are believed to be highly reactive with weakly-bound electrons, which are intrinsically rich in the characteristic reductive microenvironment of cancer cells. The latter was recently unraveled by the inventor [Lu et al., 2013]. Some general features of the compounds of the present disclosure are that they comprise an aromatic ring (rather than a platinum coordinating ion), coupled to one or more electron transfer promoters, such as $NH_2$ groups, and one or more electron-accepting leaving groups, such as halogen.

It has been surprisingly demonstrated that the NPB compounds disclosed herein are non-toxic toward normal cells, even at very high doses up to 200 µM, while they alone can induce significant DNA double-strand breaks and apoptosis and effectively kill the cancer cells in vitro or in vivo. The compounds are essentially inert to normal cells, possibly due to the lack of weakly-bound electrons (i.e., a reductive intracellular environment) within normal cells [Lu et al., 2013], and therefore have no or low systemic or acute toxicity in the body. They are highly effective anti-cancer agents that can preferentially kill cancer cells and are therefore useful for natural targeted chemotherapy of cancer and potentially other disorders treatable by chemotherapy. The disclosed compounds are expected to be superior to cisplatin, which is highly toxic due to the containing of the heavy metal (Pt), and halopyrimidines, which are ineffective as anti-cancer agents [Prados et al., 1999] due to the lack in their structures of an electron-transfer promoter (such as, e.g., diamino) for effective DET reactions [Lu, 2007, 2010].

In some embodiments, the NPB anti-cancer compound has the general formula I:

(I)

wherein A is a 5- or 6-membered aryl or heteroaryl ring containing 0-2 ring heteroatoms selected from the group consisting of N, O and S, the remaining ring atoms being carbon, $R^a$ and $R^b$ are, independently, H, OH, alkyl, alkoxy, alkenyl, alkynyl, cycloalkyl, cycloalkenyl, cycloalkynyl, aryl, heterocyclyl, heteroaryl or an electron transfer promoter, wherein at least one of $R^a$ and $R^b$ is an electron transfer promoter; $R^c$ is, independently for each occurrence, H, OH, alkyl, alkoxy, alkenyl, alkynyl, cycloalkyl, cycloalkenyl, cycloalkynyl, aryl, heterocyclyl, heteroaryl, a leaving group, or two adjacent $R^c$ groups taken together with the ring atoms to which they are attached form a 5- or 6-membered saturated, partially saturated or unsaturated ring which contains 0-2 ring heteroatoms selected from N, O and S and which can be optionally substituted with 1-4 $R^d$; wherein at least one $R^c$ is a leaving group; $R^d$ is independently OH, alkyl, alkoxy, alkenyl, alkynyl, cycloalkyl, cycloalkenyl, cycloalkynyl, aryl, heterocyclyl or heteroaryl; and n=1-4, wherein each of the alkyl, alkoxy, alkenyl, alkynyl, cycloalkyl, cycloalkenyl, cycloalkynyl, aryl, heterocyclyl and heteroaryl moieties is optionally substituted; or a pharmaceutically acceptable salt thereof.

In some embodiments, the NPB anti-cancer compound has the general formula II:

(II)

wherein: X and Y are independently C—$R^3$ or N; $R^3$ is H, OH, halogen, alkyl, alkoxy, alkenyl, alkynyl, cycloalkyl, cycloalkenyl, cycloalkynyl, aryl, heterocyclyl, or heteroaryl; $R^a$ and $R^b$ are, independently, H, OH, alkyl, alkoxy, alkenyl, alkynyl, cycloalkyl, cycloalkenyl, cycloalkynyl, aryl, heterocyclyl, heteroaryl or an electron transfer promoter, wherein at least one of $R^a$ and $R^b$ is an electron transfer promoter; $R^1$ and $R^2$ are, independently, H, OH, alkyl, alkoxy, alkenyl, alkynyl, cycloalkyl, cycloalkenyl, cycloalkynyl, aryl, heterocyclyl, heteroaryl, or a leaving group; wherein at least one of $R^1$ and $R^2$ is a leaving group, wherein each of the alkyl, alkoxy, alkenyl, alkynyl, cycloalkyl, cycloalkenyl, cycloalkynyl, aryl, heterocyclyl and heteroaryl moieties is optionally substituted; or a pharmaceutically acceptable salt thereof.

In some embodiments, the NPB anti-cancer compound has the general formula III,

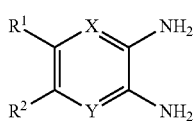

(III)

wherein X and Y are independently C—R³ or N; R³ is H, OH, halogen, alkyl, alkoxy, alkenyl, alkynyl, cycloalkyl, cycloalkenyl, cycloalkynyl, aryl, heterocyclyl, or heteroaryl; R¹ and R² are, independently, H, OH, alkyl, alkoxy, alkenyl, alkynyl, cycloalkyl, cycloalkenyl, cycloalkynyl, aryl, heterocyclyl, heteroaryl, or a leaving group; wherein at least one of R¹ and R² is a leaving group, wherein each of the alkyl, alkoxy, alkenyl, alkynyl, cycloalkyl, cycloalkenyl, cycloalkynyl, aryl, heterocyclyl and heteroaryl moieties is optionally substituted; or a pharmaceutically acceptable salt thereof.

Aromatic Ring Systems

In each of the general formulas I, II and III, the core of the molecule is a conjugated or aromatic ring system that may consist of one aryl or heteroaryl ring (monocyclic), or may consist of a multiple rings (polycyclic). In some cases, the aromatic core may comprise 2 or 3 fused rings to form a bi-cyclic, or tri-cyclic core, respectively. Aromatic ring systems are capable of transporting an electron transiently stabilized by the electron transfer promoter, such as $NH_2$ groups, acquired through reaction with a weakly-bound electron, to the site of a leaving group. When a temporary anion of the molecule is formed, it can rapidly cause a loss of the leaving group, such as a stable anion, and produce a highly reactive radical.

The aromatic core may be single 5- or 6-membered aromatic ring, such as aryl or heteroaryl. Some examples of 6-membered mono-cyclic rings include, but are not limited to, benzene, pyridine, and pyrazine. Some examples of 5-membered heteroaryl rings include, but are not limited to, furan, pyrole, thiophene and oxazole.

In some embodiments, e.g. embodiments of general Formula I, II or III, the compound comprises a 5- or 6-membered aryl or heteroaryl ring containing 0-2 ring heteroatoms selected from the group consisting of N, O and S, the remaining ring atoms being carbon. In some cases, the core is a 6-membered aromatic ring containing 0, 1 or 2 ring heteroatoms selected from N, such as benzene (0 N), pyridine (1 N), or pyrazine (2 N). In some cases, the core is a 6-membered aryl ring containing 0 ring heteroatoms, such as benzene. In some cases, the core is a 6-membered heteroaryl ring containing 1 or 2 ring heteroatoms selected from N, such as pyridine (1 N) or pyrazine (2 N).

In some embodiments, substituents (e.g. $R^c$ in Formula I) adjacent one another on the core ring may, together with the ring atoms to which they are attached, form a 5- or 6-membered saturated, partially saturated or unsaturated ring, thereby forming a polycyclic ring system. Some examples of fused bi-cyclic 6-membered rings include, but are not limited to, naphthalene, quinolone, isoquinoline, quinoxaline, quinazoline, cinnoline and phthalazine. Some examples of fused tri-cyclic 6-membered rings include, but are not limited to, anthracene, phenanthracene, and acridine. In some cases, a polycyclic ring system may comprise a combination of 5- and 6-membered ring moieties. Where the core is a polycyclic ring system, it is desirable that the compound as a whole retain its ability to transiently stabilize and transport an electron to the site of a leaving group such that a reactive radical to generate biological effects can be formed.

Electron Transfer Promoters

The anti-cancer compounds of the present disclosure comprise one or more electron transfer promoters coupled to the aromatic ring system (e.g. one or both of $R^a$ and $R^b$ in Formula I or II, and —$NH_2$ in Formula III). An "electron transfer promoter", as used herein, is an atom or functional group that assists in capturing and transiently stabilizing a weakly-bound electron. The electron is then transported through the aromatic ring system to cause breakage of a bond between a ring carbon atom and a leaving group. Once the leaving group breaks away from the ring, the resulting neutral radical is highly reactive, e.g. with DNA to cause DNA damage and death of a cancer cell. Thus, it is believed that the electron transfer promoter, preferably two electron transfer promoters in close proximity to one another, enhances the electron-attracting ability of the NPB molecule, making it more reactive with a weakly-bound electron existing in a cancer cell.

Where there are multiple electron transfer promoters on the molecule (e.g. $R^a$ and $R^b$ are both electron transfer promoters), the electron transfer promoters may be the same or different. In some embodiments, the electron transfer promoters are the same. In preferred embodiments, two electron transfer promoters are positioned in close proximity to one another on the ring, e.g. on adjacent ring carbons. This is a particularly effective arrangement for capturing and transferring electrons, particularly when strong leaving groups are present on the ring.

Examples of electron transfer promoters include but are not limited to —$NH_2$, —NEM, —$NR_2$, —OH, —OR, —O—, —$NHCOCH_3$, —NHCOR, —$OCH_3$, —OR, —$CH_3$, —$C_2H_5$, R, and —$C_6H_5$.

In some embodiments, e.g. of Formula I, II or III, the electron transfer promoter is selected from the group consisting of —$NH_2$, —NHR, —$NR_2$, —OH, —OR, —O—, —$NHCOCH_3$, —NHCOR, —$OCH_3$, —OR, —$CH_3$, —$C_2H_5$, R, and —$C_6H_5$. In some embodiments, e.g. of Formula I, II or II, the electron transfer promoter is selected from the group consisting of —$NH_2$, —NHR, —$NR_2$, —OH, —$NHCOCH_3$, —NHCOR, —$OCH_3$, and OR. In some embodiments, e.g. of Formula I, II or II, the electron transfer promoter is a selected form the group consisting of —$NH_2$, —NHR, —$NR_2$, —OH, and —O—. In some embodiments, the electron transfer promoter is selected from the group consisting of —$NH_2$, —NHR, —$NR_2$, and —OH. In some embodiments, the electron transfer promoter is selected form the group consisting of —$NH_2$, —NHR, —$NR_2$. In some embodiments, the electron transfer promoter is —$NH_2$. In some embodiments, the electron transfer promoter is NHR. In some embodiments, the electron transfer promoter is —$NR_2$. In some embodiments, e.g. of Formula I, II or II, the electron transfer promoter is selected from the group consisting of —$NHCOCH_3$, —NHCOR, —$OCH_3$, and OR.

R in any of the above may, for example, be substituted or unsubstituted alkyl, alkoxy, alkenyl, alkynyl, cycloalkyl, cycloalkenyl, cycloalkynyl, aryl, heterocyclyl or heteroaryl groups. In the case of $R_2$, each R may be the same or different. In some embodiments, R is substituted or unsubstituted alkyl.

In some embodiments, e.g. of Formula I or II, one of $R^a$ and $R^b$ is an electron transfer promoter. In some embodiments, both of $R^a$ and $R^b$ is an electron transfer promoter. In some embodiments, both of $R^a$ and $R^b$ are the same electron transfer promoter. In some embodiments, IV and $R^b$ are positioned on adjacent ring atoms. In some embodiments, a leaving group is positioned meta, ortho or para to the electron transfer promoter. In some embodiments, a leaving group is positioned meta to the electron transfer promoter. In some embodiments, a leaving group is positioned ortho to the electron transfer promoter. In some embodiments, a leaving group is positioned para to the electron transfer promoter.

Leaving Groups

The NPB compounds of the present disclosure comprise one or more leaving groups coupled to the aromatic ring system (e.g. one or both of $R^1$ and $R^2$ in Formula I, II or III). Additional leaving groups may also be provided as substituents on the aromatic ring. Where there are multiple leaving groups, the leaving groups may be the same or different. In some embodiments, the leaving groups are the same. The presence of a strong leaving group (e.g., a highly oxidizing atom, such as a halogen atom) on the molecule can enhance the reactivity of the molecule with weakly-bound electrons existing in a cancer cell, particularly when the leaving group is operatively positioned with respect to the electron transfer promoter (e.g. within 1, 2 or 3 ring atoms).

A leaving group, as used herein, is a molecular fragment that departs from the heterolytic bond cleavage. It can be an anion or neutral atom/molecule, but in either case it is crucial that the bond breakage (dissociation) of the NPB molecule, i.e., the formation of a leaving group, results in an unpaired electron at the remaining (the ring) part or the leaving group (e.g., a halogen atom) of the NPB molecule, that is, forming a reactive radical. Common anionic leaving groups include, but are not limited to, halides, such as, Cl, Br, I and F (e.g. $Cl^-$, $Br^-$, $I^-$, $F^-$), and sulfonate esters, such as tosylate, nosylate, mesylate and triflate. Other leaving groups include, but are not limited to, dinitrogen, dialkyl ethers, alcohols, nitrates, phosphates, and other inorganic esters.

In some embodiments, e.g. of Formula I, II or II, the leaving group is an anionic leaving group. In some embodiments, the leaving group is halogen. In some embodiments, the leaving group is Cl, Br, I or F. In some embodiments, the leaving group is Cl. In some embodiments, the leaving group is Br. In some embodiments, the leaving group is I. In some embodiments, the leaving group is F. In some embodiments, the leaving groups are halogen selected from the group consisting of Cl, Br and I. In some embodiments, the leaving group is a neutral species of one of these leaving groups.

In some embodiments of Formula I, one or two $R^c$ groups on Ring A are leaving groups. In some embodiments of Formula I, two $R^c$ groups on Ring A are leaving groups.

In some embodiments of Formula I, Ring A is a 6-membered aryl or heteroaryl ring, such as benzene, pyridine or pyrazine, each of $R^a$ and $R^b$ are $NH_2$; two $R^c$ substituents on Ring A are halogen each positioned meta to one of $R^a$ and $R^b$ on Ring A; and any remaining Re groups are as defined herein. In some embodiments, Ring A is benzene. In some embodiments, where Ring A is benzene, the remaining carbons on Ring A are unsubstituted carbon. In some embodiments, Ring A is pyridine. In some embodiments, where Ring A is pyridine, the remaining carbon on Ring A is unsubstituted. In some embodiments, Ring A is pyrazine.

In some embodiments, the leaving group is positioned ortho (e.g. within 1 ring atom), meta (e.g. within 2 ring atoms) or para (e.g. within 3 ring atoms) to the electron transfer promoter.

Substituents

In embodiments of Formula I, II or III, carbon atoms may be unsubstituted or substituted, unless otherwise specified.

In embodiments, of Formula I, II or III, unless defined otherwise, ring carbon atoms may be unsubstituted or substituted. Substituents may include, for example, OH, halogen, alkyl, alkoxy, alkenyl, alkynyl, cycloalkyl, cycloalkenyl, cycloalkynyl, aryl, heterocyclyl or heteroaryl groups. Each of the carbon-based substituents (e.g. alkyl, alkoxy, alkenyl, alkynyl, cycloalkyl, cycloalkenyl, cycloalkynyl, aryl, heterocyclyl or heteroaryl) may optionally be further substituted.

In embodiments of Formula I, $R^c$ is, independently for each occurrence, H, OH, alkyl, alkoxy, alkenyl, alkynyl, cycloalkyl, cycloalkenyl, cycloalkynyl, aryl, heterocyclyl, heteroaryl, a leaving group, or two adjacent $R^c$ groups taken together with the ring atoms to which they are attached form a 5- or 6-membered saturated, partially saturated or unsaturated ring which contains 0-2 ring heteroatoms selected from N, O and S and which can be optionally substituted with 1-4 $R^d$; wherein at least one $R^c$ is a leaving group. $R^d$ is independently OH, alkyl, alkoxy, alkenyl, alkynyl, cycloalkyl, cycloalkenyl, cycloalkynyl, aryl, heterocyclyl or heteroaryl; and n=1-4 (e.g. 1, 2, 3 or 4). Each of the alkyl, alkoxy, alkenyl, alkynyl, cycloalkyl, cycloalkenyl, cycloalkynyl, aryl, heterocyclyl and heteroaryl moieties may be optionally substituted.

In embodiments of Formula I and II, $R^a$ and $R^b$ are, independently, H, OH, alkyl, alkoxy, alkenyl, alkynyl, cycloalkyl, cycloalkenyl, cycloalkynyl, aryl, heterocyclyl, heteroaryl or an electron transfer promoter, wherein at least one of IV and $R^b$ is an electron transfer promoter. Each of the alkyl, alkoxy, alkenyl, alkynyl, cycloalkyl, cycloalkenyl, cycloalkynyl, aryl, heterocyclyl and heteroaryl moieties may be optionally substituted.

In embodiments of formula II or III, where X and Y are independently $C-R^3$ or N, and $R^3$ may be H, OH, halogen, alkyl, alkoxy, alkenyl, alkynyl, cycloalkyl, cycloalkenyl, cycloalkynyl, aryl, heterocyclyl, or heteroaryl. Each of the alkyl, alkoxy, alkenyl, alkynyl, cycloalkyl, cycloalkenyl, cycloalkynyl, aryl, heterocyclyl and heteroaryl moieties may be optionally substituted.

In embodiments of formula II or III, $R^1$ and $R^2$ are, independently, H, OH, alkyl, alkoxy, alkenyl, alkynyl, cycloalkyl, cycloalkenyl, cycloalkynyl, aryl, heterocyclyl, heteroaryl, or a leaving group. Each of the alkyl, alkoxy, alkenyl, alkynyl, cycloalkyl, cycloalkenyl, cycloalkynyl, aryl, heterocyclyl and heteroaryl moieties may be optionally substituted. In the above, at least one of $R^1$ and $R^2$ is a leaving group. In some embodiments, both $R^1$ and $R^2$ are leaving groups, where $R^1$ and $R^2$ may be the same or different.

Unless otherwise specified, optionally substituted carbon-based groups above may further include one or more functional groups on the substituent, such as hydroxyl, amino, amido, cyano, nitro, carboxyl, ester, ether, ketone, aldehyde, aryl, and heteroaryl, or a combination thereof.

A skilled person will be able to modify the compounds disclosed herein to produce numerous anti-cancer compounds in accordance with the present disclosure. When selecting substituents, factors such as stability, water solubility, toxicity and reactivity (e.g. reactivity with an electron) of the resulting compound, among other factors, should be considered.

Non-Limiting Exemplary NPB Compounds

Some exemplary non-limiting NPB compounds of the present disclosure are shown below:

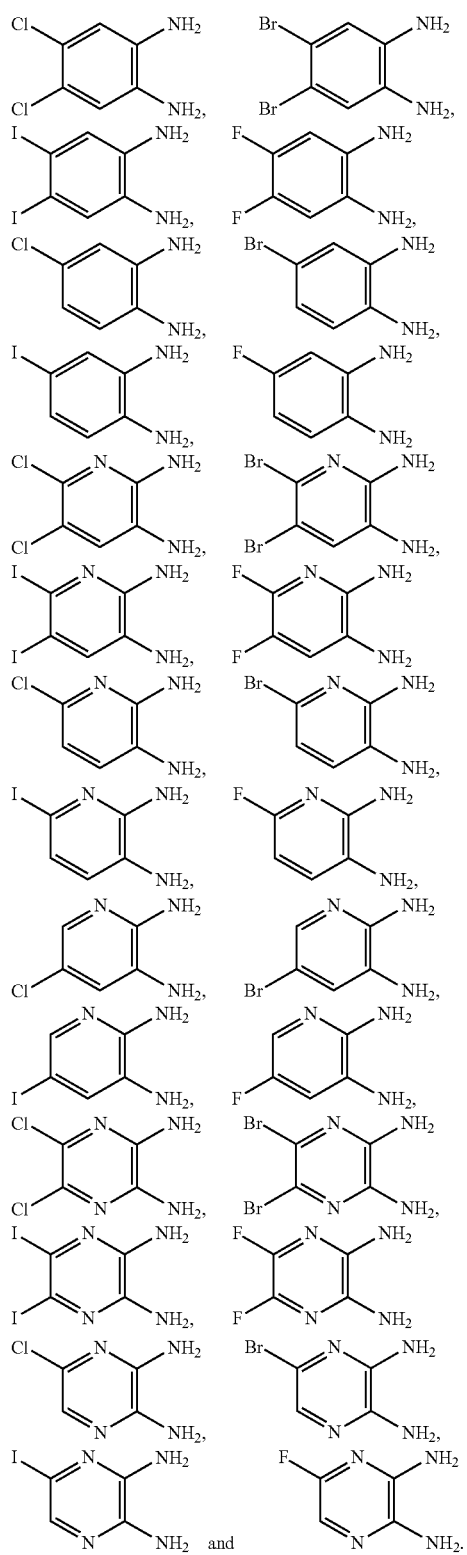

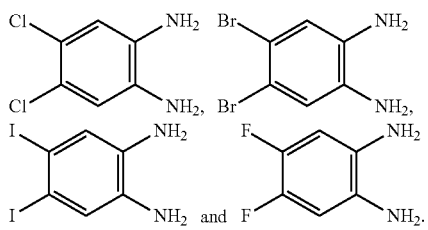

ments, a halogen leaving group is positioned meta to each of the NH₂ groups. It has been found that compounds having this structure are highly effective anti-cancer agents. Without being bound by theory, it is believed that such embodiments are particularly effective due to combination of two strong electron transfer promoters in close proximity to one another on the aromatic ring system, capable of capturing a weakly-bound electron and transporting it through the ring to the site of a nearby leaving group to thereby form a highly-reactive radial that can attack DNA and cause cancer cell death.

In some embodiments, the NPB compound is selected from the group consisting of:

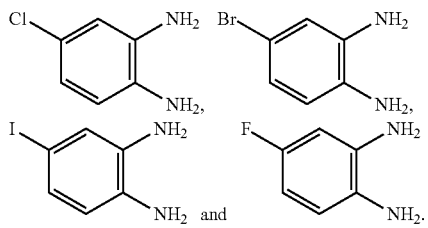

In some embodiments, the NPB compound is selected from the group consisting of:

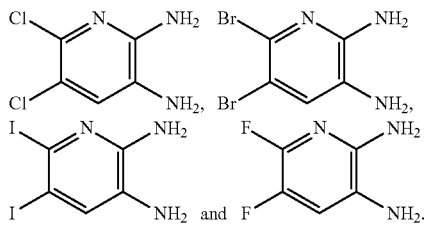

In some embodiments, the NPB compound is selected from the group consisting of:

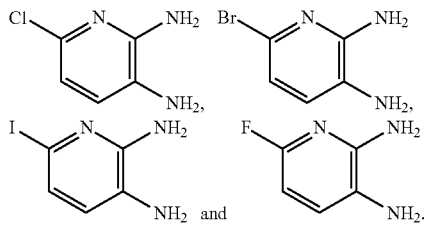

In some embodiments, the NPB compound is selected from the group consisting of:

In each of the above exemplary embodiments, the compound comprises a 6-membered aryl or heteroaryl ring selected from benzene, pyridine and pyrazine; two NH₂ electron transfer promoter groups positioned adjacent to one another on the ring, and at least one halogen leaving group positioned meta to one of the NH₂ groups. In some embodi- In some embodiments, the NPB compound is selected from the group consisting of:

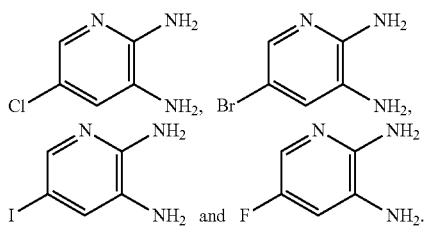

In some embodiments, the NPB compound is selected from the group consisting of:

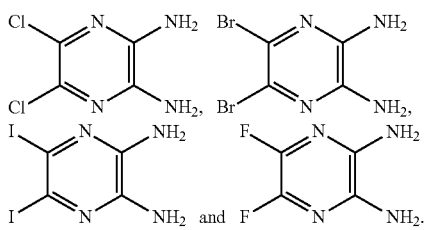

In some embodiments, the NPB compound is selected from the group consisting of:

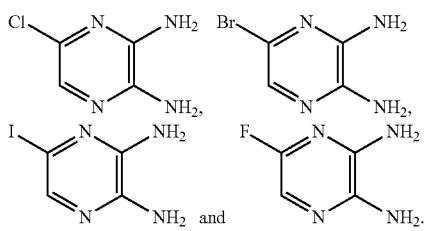

Electron Affinity

The electron affinity ($E_A$) of an atom or molecule is generally defined as the energy change when an electron is added to a neutral atom or molecule to form a negative ion:

$$X + e^- \rightarrow X^- + \text{energy}.$$

Molecules having a positive electron affinity (e.g. >0 eV) are more susceptible to receiving electrons than molecules having a negative electron affinity (e.g. <0.0 eV). In accordance with the present disclosure, a positive electron affinity is a desirable property as it relates to the reactivity of the NPB compounds with weakly-bound electrons existing in a cancer cell. It is therefore preferable that the NPB compounds have an electron affinity greater than 0.0 eV.

In some embodiments, e.g. embodiments of Formula I, II or III, the electron affinity of the NPB compounds disclosed herein is positive (e.g. >0.0 eV). In some embodiments, the electron affinity of the NPB is between about 0.0 eV and about +5.0 eV, between about 0.0 eV and about +4.0 eV, between about 0.0 eV and about +3.0 eV, or between about 0.0 eV and about +2.5 eV.

In some embodiments, the electron affinity of the NPB is between about +0.2 eV and about +5.0 eV, or between about +0.2 eV and about +4.0 eV, or between about +0.2 eV and about +3.0, or between about +0.2 eV and about +2.0 eV.

In some embodiments, the electron affinity of the NPB is between about +0.5 eV and about +3.0 eV, between about +0.5 eV and about +2.5 eV, between about +0.5 eV and about +2.0 eV, or between about +0.5 eV and about +1.5 eV.

The electron affinity of a molecule may be determined by skilled persons using methods known in the art.

Radiolabelled NPB Compounds

The NPB compounds of the present disclosure may be radiolabelled, i.e., said compounds may contain one or more atoms containing an atomic mass or mass number different from the atomic mass or mass number: ordinarily found in nature. Exemplary radioisotopes of hydrogen, carbon, phosphorous, fluorine and chlorine include $^3$H, $^{14}$C, $^{32}$P, $^{35}$S, $^{43}$F and $^{36}$Cl, respectively. Radiolabelled compounds can generally be prepared by methods well known to those skilled in the art. In some cases, such radiolabelled compounds can be prepared by carrying out general synthetic procedures and substituting a readily available radiolabelled reagent for a non-radiolabelled reagent.

Chemical Definitions

The following well-known chemical terms have the following general meanings, unless otherwise specified.

As used herein, the term "aryl" means a substituted or unsubstituted aromatic hydrocarbon ring system having 6-14 ring atoms, e.g. 6 ring atoms, which may be a mono-, bi- or tri-cyclic aromatic ring system, including but not limited to those aryl groups in the molecules disclosed or exemplified herein. In some embodiments disclosed herein, "aryl" denotes a 6-membered aromatic ring, which may optionally be fused to one or more aromatic or non-aromatic rings.

The term "alkyl" denotes a saturated linear or branched hydrocarbon group containing, e.g., from 1 to 10 carbon atoms, e.g. from 1 to 6 carbon atoms or from 1 to 4 carbon atoms, for example, methyl, ethyl, propyl, isopropyl, n-butyl, i-butyl, 2-butyl, t-butyl including but not limited to those alkyl groups in the molecules disclosed or exemplified herein. The term "lower alkyl" may also be used and it typically refers to a linear or branched hydrocarbon group containing 1-6 carbon atoms (e.g. $C_1$-$C_6$ alkyl). $C_1$-$C_6$ alkyl is intended to include $C_1$, $C_2$, $C_3$, $C_4$, $C_5$, and $C_6$ alkyl groups. Furthermore, alkyl groups may be substituted or unsubstituted.

The term "alkoxy" denotes a group wherein the alkyl residues are as defined above, and which is attached via an oxygen atom, e.g. methoxy and ethoxy. Alkoxy can optionally be substituted with one or more substituents. For example, "alkoxy" refers to groups —O-alkyl, wherein the alkyl group is as defined above. Examples of "alkoxy" include, but are not limited to, methoxy, ethoxy, n-propoxy, i-propoxy, t-butoxy, n-butoxy, s-pentoxy and the like. Furthermore, alkoxy groups may be substituted or unsubstituted.

The term "alkenyl" denotes a carbon chain of from 2 to 12, e.g. from 2 to 6, carbon atoms comprising a double bond in its chain. For example, $C_{2-6}$-alkenyl groups, include, e.g., ethenyl, propen-1-yl, propen-2-yl, buten-1-yl, buten-3-yl, penten-1-yl, penten-2-yl, penten-3-yl, penten-4-yl, hexen-1-yl, hexen-2-yl, hexen-3-yl, hexen-4-yl and hexen-5-yl. Furthermore, alkenyl groups may be substituted or unsubstituted.

The term "alkynyl" is intended to include hydrocarbon chains of either linear or branched configuration, having one or more carbon-carbon triple bonds that may occur in any stable point along the chain. Unless otherwise specified, "alkynyl" groups refer refers to groups having 2 to 8, e.g. 2 to 6 carbons. Examples of "alkynyl" include, but are not limited to prop-2-ynyl, but-2-ynyl, but-3-ynyl, pent-2-ynyl, 3-methylpent-4-ynyl, hex-2-ynyl, hex-5-ynyl, etc. Furthermore, alkynyl groups may be substituted or unsubstituted.

The term "cycloalkyl" denotes any stable cyclic or polycyclic hydrocarbon group containing 3 to 13 carbons, e.g., e.g. from 3 to 6 carbons. As in the case of other alkyl moieties, cycloalkyl can optionally be substituted with one or more substituents.

The term "cycloalkenyl" includes any stable cyclic or polycyclic hydrocarbon groups of from 3 to 13 carbon atoms, e.g. 5 to 8 carbon atoms, which contains one or more unsaturated carbon-carbon double bonds that may occur in any point along the cycle. As in the case of other alkenyl moieties, cycloalkenyl may optionally be substituted.

Cycloalkynyl includes any stable cyclic or polycyclic hydrocarbon groups of from 5 to 13 carbon atoms, which contains one or more unsaturated carbon-carbon triple bonds that may occur in any point along the cycle. As in the case of other alkynyl moieties, cycloalkynyl may optionally be substituted.

The term "heterocyclyl" refers to non-aromatic ring systems having five to fourteen ring atoms, e.g. 5 to 10 ring atoms, in which one or more ring carbons, e.g. 1 to 4, are each replaced by a heteroatom such as N, O, or S, the rest of the ring members being carbon atoms. The heterocyclyl can optionally be substituted with one or more substituents, independently at each position.

The term "heteroaryl" refers to a mono- or polycyclic aromatic ring system having 5-14 ring atoms, e.g. 5 or 6 ring atoms, containing at least one ring heteroatom selected from N, O, or S, the rest of the ring members being carbon atoms. Heteroaryl moieties can optionally be substituted, independently at each position. Examples of heteroaryl moieties include but are not limited to those in the molecules disclosed or exemplified herein.

The term "aliphatic group" refers to, e.g., alkyl, alkenyl, alkynyl, alkoxy, haloalkyl, cycloalkyl, cycloalkenyl, cycloalkynyl or non-aromatic heterocyclic groups. Aliphatic groups may contain one or more substituents.

The term "amine" may refer to an organic compound or functional group (i.e. amino) that contains a basic nitrogen atom with a lone electron pair, including, primary amine ($NRH_2$), secondary amine ($NR_1R_2H$), and tertiary amine ($NR_1R_2R_3$) where each R may be the same or different. Also, two R groups may denote members of a ring, e.g., where N is a heteroatom in a heterocyclic or heteroaryl ring.

Also included within the scope of the present disclosure are pharmaceutically acceptable salts of the compounds disclosed herein.

The descriptions of compounds of the present application are limited by principles of chemical bonding known to those skilled in the art. Accordingly, where a group may be substituted by one or more substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions.

Pharmaceutical Compositions and Dosage Forms

The NPB compounds disclosed herein may be present in a pharmaceutical composition, or in one of various pharmaceutical dosage forms, suitable for administration to a subject. Pharmaceutical compositions and dosage forms comprising the NPB compounds of the present disclosure are useful for targeted chemotherapy.

A "pharmaceutical composition" refers to a combination of ingredients that facilitates administration of one or more agents of interest (e.g. a NPB compound) to a subject. A pharmaceutical composition generally comprises one or more agents of interest in admixture with one or more pharmaceutically acceptable carriers or diluents. Many pharmaceutically-acceptable "carriers" and "diluents" are known in the art and these generally refer to a pharmaceutically-acceptable materials, compositions, or vehicles, including liquid or solid fillers, diluents, excipients, solvents, binders, or encapsulating materials.

Each component in the composition must be "pharmaceutically acceptable" in the sense of being compatible with the other ingredients of a pharmaceutical formulation. Each component the composition, including the NPB compound, must also be "biocompatible", such that the composition is suitable for contact with the tissues or organs of a subject without excessive toxicity, irritation, allergic response, immunogenicity, or other problems or complications, commensurate with a reasonable benefit/risk ratio.

For more information on pharmaceutical compositions, see, e.g., Remington: The Science and Practice of Pharmacy, 21st Edition; Lippincott Williams & Wilkins: Philadelphia, Pa., 2005; Handbook of Pharmaceutical Excipients, 5th Edition; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Preformulation and Formulation, Gibson Ed CRC Press LLC: Boca Raton, Fla., 2004).

The pharmaceutical compositions disclosed herein may be formulated in any suitable dosage form, including single-unit and multiple-unit dosage forms. Exemplary dosage forms include, for example, a liquid, a solution, a suspension, an emulsion, a concentrate, a powder, a paste, a gel, a gum, a drop, a tablet, a capsule or a microcapsule. In some embodiments, the dosage form is a liquid. In some embodiments, the liquid is a solution, a suspension, or an emulsion.

Routes of Administration

The NPB compounds and pharmaceutical compositions containing them may be administered by any suitable route of administration. For example, the NPB compound be administered locally (e.g. into a tumor), regionally (e.g. into a body cavity) or systemically (e.g. into a blood vessel, such as a vein or artery).

In some embodiments, the NPB compound is formulated for enteral administration, topical administration, parenteral administration, or nasal administration. Enteral administration may comprise, for example, oral administration.

In some embodiments, the NPB compound or composition is formulated for parenteral administration. Parenteral administration may comprise, for example, intravenous, intraarterial, intracerebral, intraperitoneal, intramuscular, subcutaneous, intracardiac, or intraosseous administration. In some embodiments, the parenteral administration is intravenous administration, e.g. injection or infusion. In some embodiments, the parenteral administration is intraarterial administration. In some embodiments, the parenteral administration is intraperitoneal administration.

In some embodiments, the parenteral administration is systemic or regional. In some embodiments, the parenteral administration is systemic. In some embodiments, the NPB compound or composition is administered intravenously.

Dosage of NPB Compound

The NPB compound or composition may be administered according to any treatment regimen deemed appropriate by the skilled worker (e.g. clinician).

The dosage requirements of the NPB compounds and pharmaceutical compositions containing them will vary with the particular compounds or combinations employed, the route of administration, the particular disease or condition to be treated, including cancer and other diseases or conditions, and the patient to be treated. Treatment will generally be initiated with small dosages less than the optimum dose of the compound. Thereafter, the dosage is increased until the optimum effect under the circumstances is reached. In general, the NPB compounds and compositions according to the present invention are administered at a concentration that will afford effective results without causing harmful or deleterious side effects. As with any chemotherapy, a certain degree of toxic side effects may be considered acceptable.

In general, a sufficient amount of the NPB compound should be employed to effectively kill cancer cells. Generally, a dose of the NPB compound will be selected such that the NPB compound does not contribute significant unwanted effects to the therapy (the subject).

When administered for the prevention or treatment or inhibition of a particular disease or condition, the effective dosage of the NPB compound may vary depending upon the particular compound utilized, the mode of administration, the condition, and severity thereof, of the condition being treated, as well as the various physical factors related to the individual being treated. In many cases, satisfactory results may be obtained when the compound is administered in a daily dosage of between about 0.01 mg/kg and about 500 mg/kg, between about 0.1 mg/kg and about 125 mg/kg, between 1 mg/kg and about 50 mg/kg, between 1 mg/kg and about 25 mg/kg, between about 0.3 mg/kg and about 15 mg/kg, or between about 0.5 mg/kg and 5 mg/kg, or between about 5 mg/kg and 10 mg/kg. In some cases, the subject may receive a single-dose treatment or multiple-dose treatments. In some embodiments, the NPB compounds are substantially non-toxic to normal cells and therefore may be tolerated at relatively high doses (e.g. 10 mg/kg-about 50 mg/kg, or between about 10 mg/kg to about 30 mg/kg). The projected daily dosages are expected to vary with route of administration. Thus, parenteral dosing will often be at levels of roughly 10% to 20% of oral dosing levels.

Methods of Treatment

The present disclosure encompasses methods of treating cancer and other diseases and conditions treatable (or believed to be treatable) by chemotherapy. In one aspect, the present disclosure relates to methods of treating cancer. In another aspect, the present disclosure relates a targeted chemotherapy for cancer. The methods and targeted chemotherapies disclosed herein are typically administered to individuals who have been diagnosed with cancer. However, in some cases, the targeted chemotherapy may be administered to individuals who do not yet show clinical signs of cancer, but who are at risk of developing cancer, or to subjects who have previously been diagnosed with cancer but are in a period of remission or at risk of a relapse. Toward this end, the present disclosure also relates to methods of preventing or reducing the risk of developing cancer, as well as methods of treating a relapse or prolonging a remission.

In one aspect, there is provided a method of generating chemotherapeutic effects in a subject in need thereof comprising administering an effective amount of a compound as defined herein. In one aspect, the present disclosure relates to methods of treating cancer in a subject in need thereof by administering an effective amount of a NPB compound as defined herein to a subject. In some embodiments, the method may be for prevention, control, inhibition, or complete cure of cancer in a subject.

In some embodiments, the treatment excludes radiation. In other words, the compounds are used in the absence of radiation such that they are used as anti-cancer agents rather than radiosensitizers. This means that the subject is not receiving radiation treatment in a manner that would interact with the NPB anti-cancer activity. The subject may however receive radiation treatment at another time that does not interact with the compounds of the invention.

In some embodiments, the cancer is one that is sensitive to a Pt-based anti-cancer drug (e.g. cisplatin) or another cancer therapy with toxic side effects. In some embodiments, the cancer is one that is resistant to a Pt-based anti-cancer drug (e.g. cisplatin) or another cancer therapy with toxic side effects.

The compounds disclosed herein may also be used to treat other diseases or conditions treatable by chemotherapy, for example, AL amyloidosis, ankylosing spondylitis, multiple sclerosis, Crohn's disease, psoriasis, psoriatic arthritis, systemic lupus erythematosus, rheumatoid arthritis, scleroderma, autoimmune disorders, noncancerous plasma cell dyscrasia, trigeminal neuralgia, acoustic neuromas, severe thyroid eye disease, pterygium, pigmented villonodular synovitis, and prevention of keloid scar growth, vascular restenosis, and heterotopic ossification. The NPB compounds may also be used in conditioning regimens prior to bone marrow transplant (hematopoietic stem cell transplant). Thus, in another aspect, there is provided a method of treating a disease or condition treatable by chemotherapy in a subject by administering an effective amount of a NPB compound as defined herein to the subject. The disease or condition may be a non-cancer disease or condition. In some embodiments, the disease is cancer.

In another aspect, there is provided a method of reducing or overcoming Pt-based drug (e.g., cisplatin) toxicity, wherein any of the methods described above are applied to a cell or a cancer that is sensitive to Pt-based drug (cisplatin) treatment, or are applied to a subject having a cell or a cancer that is sensitive to Pt-based drug (cisplatin) treatment.

In another aspect, there is provided a method of overcoming Pt-based drug (e.g., cisplatin) resistance, wherein any of the methods described above are applied to a cell or a cancer that is resistant to Pt-based drug (cisplatin) treatment, or are applied to a subject having a cell or a cancer that is resistant to Pt-based drug (cisplatin) treatment.

In another aspect, the method comprises administering to a subject in need thereof a therapeutically effective amount of a compound highly reactive with an electron. In preferred targeting and radical formation and reaction, the agent is capable of showing an anticancer effect and no systemic or acute toxic effects.

In another aspect, there is provided method of inducing an anti-cancer effect in a cancer cell, comprising: administering to the cancer cell an effective amount of a NPB compound as defined herein. In some embodiments, the anti-cancer effect is killing of the cancer cell. In some embodiments, the cancer cell is a tumour cell.

In another aspect, there is provided a method of inducing apoptosis in a cancer cell, comprising, administering to the cell an effective amount of a compound as defined herein.

The therapy is administered in a therapeutically effective amount. The features of the chemotherapy are as described in any of the embodiments disclosed herein.

It is to be understood that the terminology used herein is for the purpose of describing specific embodiments only and is not intended to be limiting. It is further to be understood that unless specifically defined herein, the terminology used herein is to be given its common meaning as known to skilled persons in the relevant field.

The term "subject" as used herein refers to a human or an animal to be treated, in particular, a mammal. Mammalian animals may include, for example, primate, cow, sheep, goat, horse, dog, cat, rabbit, rat, or mouse. In some embodiments, the subject is a human, although the compounds disclosed herein are useful for vertinary applications as well. The terms "subject" and "patient" may be used interchangeably.

The terms "disorder" and "disease" may be used interchangeably herein and may include conditions.

The term "cancer" (e.g. neoplastic disorder) as used herein refers to a disorder involving aberrant cell growth, proliferation or division (e.g. neoplasia). As cancer cells grow and divide they pass on their genetic mutations and proliferative characteristics to progeny cells. A "tumour" (e.g. neoplasm) is an accumulation of cancer cells. The methods and combinations disclosed herein may be used in the treatment of cancer, cancer cells, tumors and/or symptoms associated therewith.

Exemplary types of cancer that may be treated in accordance with the methods, uses and combinations of the present disclosure include, but are not limited to, testicular cancer, bladder cancer, cervical cancer, ovarian cancer, breast cancer, prostate cancer, head cancer, neck cancer, lung cancer (e.g. non small cell lung cancer), endometrial cancer, pancreatic cancer, Kaposi's sarcoma, adrenal cancer, leukemia, stomach cancer, colon cancer, rectal cancer, liver cancer, stomach cancer, esophageal cancer, renal cancer, thyroid cancer, uterine cancer, skin cancer, oral cancer, brain cancer, spinal cord cancer, gallbladder cancer. The cancer may, for example, include sarcoma, carcinoma, melanoma, lymphoma, myeloma, or germ cell tumours. In some embodiments, the cancer is testicular cancer, bladder cancer, cervical cancer, ovarian cancer, breast cancer, prostate cancer, head cancer, neck cancer, or lung cancer (e.g. non small cell lung cancer).

An "anti-cancer agent" refers to a therapeutic agent that directly or indirectly kills cancer cells, for example, by triggering apoptosis, or directly or indirectly prevents, stops or reduces the proliferation of cancer cells. In some cases, an "anti-antineoplastic agent" may include more than one therapeutic agent.

The term "a side effect" refers to one of the effects of chemotherapy, such as kidney toxicity, liver toxicity, severe nausea and vomiting, bone marrow depression, myelosuppression/immunosuppression, mucositis (inflammation of the lining of the digestive tract), alopecia (hair loss), cytopenia, pain, fatigue, cachexia, cutaneous complications, such as hypersensitivity reactions, and neurological, pulmonary, cardiac, reproductive and endocrine complications.

As used herein, the terms "treat," "treating" and "treatment" generally include prevention, reduction or eradication of a symptom of a disease or condition to be treated. With respect to cancer, the terms "treat," "treating" and "treatment" may include, for example, the prevention, eradication, removal, amelioration, modification, reduction, management or control of a tumor, cancer (tumor) cells or cancer, the minimization, prevention or delay of metastasis, the prevention or delay of onset of relapse, or the prolongation of survival of the subject.

The term "metastasis," as used herein, refers to the dissemination of tumor cells via lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

The term "effective amount" or "therapeutically effective amount" is intended to mean that amount of a therapeutic component, or components in a combination therapy, that will elicit a desired biological or medical response in a cell, tissue, tumor, system, or subject, which result is generally sought by a researcher, veterinarian, doctor or other clinician or technician. When referring to the effective amount of a NPB anti-cancer compound to be administered in chemotherapy, the effective amount of the compound may be an amount sufficient to provide a desired anti-cancer effect.

An "anticancer effect" may include, but is not limited to, reduction, prevention, inhibited growth or elimination of cancer cells, a tumor, or cancer; reduced or inhibited cancer cell proliferation; increased or enhanced killing or apoptosis of cancer cells; reduction or prevention of metastasis, and/or prolonged survival of a subject. In some cases, a desired biological or medical response may be amelioration, alleviation, lessening, or removing of one or more symptoms of cancer, or reduction in one or more toxic side effects associated with a particular cancer treatment.

By "inhibiting" or "reducing", e.g. cancer cell proliferation, it is generally meant to slow down, to decrease, or, for example, to stop the amount of cell proliferation, as measured using methods known to those of ordinary skill in the art, by, for example, 10%, 20%, 30%, 40%, 50%, 60%, 70%, 80%, 90%, 95%, or 100%, when compared to proliferating cells that are either not treated or are not subjected to the methods and combinations of the present application.

By "reducing" a tumor it is generally meant to reduce the size of a tumour, as measured using methods known to those of ordinary skill in the art, by, for example, 10%, 20%, 30%, 40%, 50%, 60%, 70%, 80%, 90%, 95%, or 100%, when compared to tumor size before treatment or compared to tumors that are not subjected to the methods and the NPB anti-cancer compounds of the present application.

By "increased" or "enhanced" killing or apoptosis of cancer cells, it is generally meant an increase in the number of dead or apoptotic cells, as measured using methods known to those of ordinary skill in the art, by, for example, 10%, 20%, 30%, 40%, 50%, 60%, 70%, 80%, 90%, 95%, 100%, 200%, 300% or more, when compared to cells that are either not treated or are not subjected to the methods and the NPB anti-cancer compounds of the present application. An increase in cell killing or apoptosis could also be measured as a decrease in cell viability, as measured using a standard cell viability assay.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

As used herein, the singular forms "a", "an", and "the" include plural references unless indicated otherwise.

Terms of degree such as "substantially", "about" and "approximately", as used herein, mean a reasonable amount of deviation of the modified term such that the end result is not significantly changed. These terms of degree should be construed as including a deviation of at least ±5% of the modified term if this deviation would not negate the meaning of the word it modifies.

Combination Therapy

The NPB anti-cancer compounds disclosed herein may be administered as a sole therapy or may be used in conjunction with one or more additional therapies, such as surgery or drug or radiation therapy. For instance, the additional therapy may be a cancer therapy including surgery, e.g. to remove a primary tumor, or a therapeutic agent, e.g., an antibiotic, anti-inflammatory agent or anticancer agent. Anticancer agents may include, for example, classic chemotherapeutic agents, as well as molecular targeted therapeutic agents, biologic therapy agents, and radiotherapeutic agents. Anticancer agents used in further combination with the chemotherapy of present disclosure may include agents selected from any of the classes known to those of ordinary skill in the art, including, for example, electron-donating agents, alkylating agents, anti-metabolites, plant alkaloids and terpenoids (e.g., taxanes), topoisomerase inhibitors, anti-tumor antibiotics, hormonal therapies, molecular targeted agents, and the like. In some embodiments, the anti-cancer agent is an alkylating agent, an antimetabolite, an electron-donating agent, a vinca alkaloid, a taxane, a topoisomerase inhibitor, an anti-tumor antibiotic, a tyrosine kinase inhibitor, or an immunosuppressive macrolide. It will be understood that the additional agents selected should not significantly reduce effectiveness of the NPB compounds or induce/enhance unwanted toxic side effects.

In another aspect, the present disclosure provides a combination therapy comprising a NPB compound as disclosed herein and another therapeutic agent or therapy (e.g. surgery or radiation). In preferred embodiments, the combinations have a net anti-cancer effect that is greater than the anticancer effect of the individual components of the combination when administered alone. Preferably, the anticancer effect is increased without a concomitant increase in toxic side effects.

In one aspect, there is provided a combination therapy for treating cancer or another disease treatable by chemotherapy comprising administering an effective amount of a compound as defined as defined herein to the subject; and administering one or more additional therapeutic agents to the subject. In some embodiments, the therapeutic agent is a chemotherapeutic agent.

Synergistic combinations are particularly desirable. In some embodiments, the combination exhibits a synergistic anti-cancer effect. The terms "synergistic" and "synergy" imply that the effect of the combined components of the combination is greater than the sum of the effects of the individual components when administered alone.

Uses

The NPB anti-cancer compounds disclosed herein can be used for targeted chemotherapy, e.g. for generating anti-cancer effects in the subject receiving the treatment with minimal toxicity. Thus, in one aspect, there are provided anti-cancer compounds as defined herein for use in generating anti-cancer effects of chemotherapy in a subject.

In another aspect, there are provided NPB anti-cancer compounds as defined herein for use in the treatment of cancer in a subject. In another aspect, there are provided NPB anti-cancer compounds as defined herein for use in combination with another agent/therapy in the treatment of cancer. In another aspect, there are provided NPB anti-cancer compounds as defined herein for use in the manufacture of a medicament for the treatment of cancer. In another aspect, there are provided NPB anti-cancer compounds as defined herein for use in the manufacture of a medicament for use in combination with another agent/therapy for the treatment of cancer. In another aspect, there are provided NPB anti-cancer compounds as defined herein for use in treating a disease or condition treatable by chemotherapy in a subject.

In some embodiments, the use excludes radiation.

In some embodiments, the subject has a cancer that is sensitive to platinum-based agent (e.g., cisplatin) treatment but with significant toxic effects. In some embodiments, the subject has a cancer that is resistant to platinum-based agent (e.g., cisplatin) treatment.

In accordance with the use, the chemotherapy is for administration in a therapeutically effective amount.

The NPB anti-cancer compounds disclosed herein can be used in vitro or in vivo to induce anti-cancer effects. In one aspect, there are provided NPB anti-cancer compounds as defined herein for use in treating a cancer cell (e.g. to induce an anti-cancer effect in a cancer cell).

Additional features of the use are as described in any of the embodiments disclosed herein.

Kits and Commercial Packages

In another aspect, there are provided kits and commercial packages related to the NPB anti-cancer compounds as disclosed herein for use in chemotherapy. In some embodiments, a kit or commercial package is provided comprising a NPB compound as disclosed herein. In some embodiments, the instructions are for use in combination with another agent/therapy in the treatment of cancer.

Dissociative Electron Transfer (DET) Reaction

The present inventor recently deduced the molecular mechanism of action of cisplatin in chemotherapy and in combination with radiotherapy [Lu, 2007; 2010; Lu et al. 2007]. Although cisplatin is a well-known DNA-attacking agent, its precise molecular mechanism of action had remained elusive. Through the use of femtosecond time-resolved laser spectroscopy (fs-TRLS), it was demonstrated that cisplatin is a very effective molecule for the dissociative-electron transfer (DET) reaction with a weakly-bound electron, e.g., a prehydrated electron ($e_{pre}^-$) generated by radiolysis of water:

$$e_{pre}^- + Pt(NH_3)_2Cl_2 \rightarrow [Pt(NH_3)_2Cl_2]^{*-} \rightarrow Cl^- + Pt(NH_3)_2Cl^*$$

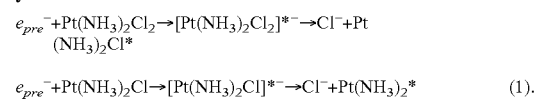

The resultant cis-Pt(NH$_3$)$_2$ radical highly effectively leads to DNA strand breaks [Lu, 2007]. It is well known that unrepaired DSBs in the cell are the most lethal form of DNA damage and directly relate to apoptosis and final clonogenic cell death.

The present inventor has now surprisingly discovered that certain non-platinum-based organic molecules can also participate in the DET reaction with a weakly-bound electron that may exist in the reductive environment inside a cancer cell, essentially acting as cisplatin analogues. Some general features of the NPB anti-cancer compounds of the present disclosure are that they comprise an aromatic ring (rather than a platinum coordinating ion), coupled to one or more electron transfer promoters, such as NH$_2$ groups, and one or more leaving groups, such as halogen. Such compounds are demonstrated herein to be effective anti-tumor compounds for chemotherapy.

Advantageously, such compounds are also demonstrated herein to be significantly less toxic to normal cells than a Pt-based agent (e.g., cisplatin). In fact, the examples provided herein demonstrate that the exemplary compounds are substantially non-toxic to normal cells, even at very high doses (200 μM).

It is demonstrated herein that contacting cancer cells with a non-platinum-based NPB anti-cancer compound of the disclosure in vitro or in vivo provides an anti-cancer efficacy of chemotherapy, while the compound itself is substantially non-toxic within the usable doses.

Based on the deduced dissociative-electron-transfer (DET) mechanism of cisplatin, described above, the non-platinum-based anti-cancer compound (NPB) is believed to react with a weakly-bound electron ($e_{wb}^-$) in a cancer cell via a DET reaction as follows:

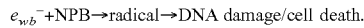
$e_{wb}^-$+NPB→radical→DNA damage/cell death.

Figure 2:
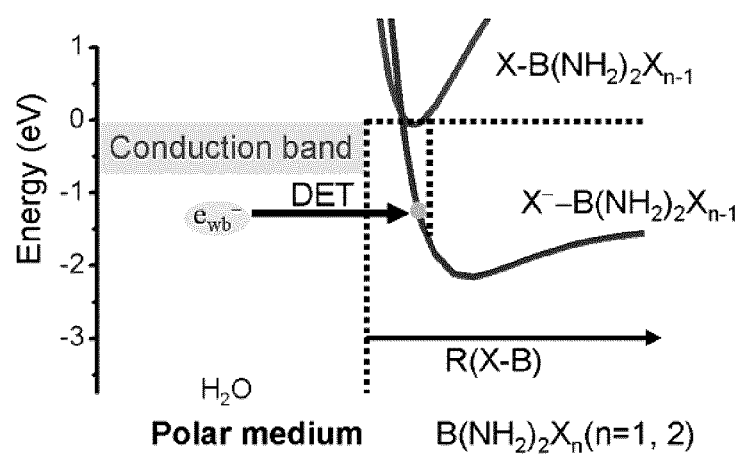
FIG. 2. Schematic diagram for the dissociative electron transfer (DET) reaction of a NPB compound [B(NH$_2$)$_2$X$_n$, n=1,2] with a weakly-bound electron ($e_{wb}^-$). When an electron-attracting NPB molecule is around an $e_w^-$ in a cancer cell, DET can take place to form a transient molecular anion NPB*$^-$ that then undergoes a chemical bond breakage (dissociation) to form a reactive radical: $e_{wb}^-$+NPB→NPB*$^-$→radical formation. The latter can subsequently result in biological effects such as DNA damage and apoptosis (cell death).

This DET reaction mechanism is schematically shown in FIG. 2. The resultant radical can effectively lead to DNA damage and apoptosis (cell death), e.g. DNA damage and cell death in a cancer cell or tumor.

Studies were carried out to demonstrate the DET mechanism of the above compounds and to explore their in vitro and in vivo anti-cancer effects. Some of the results are discussed below.

FS-TRLS Study of NPB Anti-Cancer Compounds

Figure 3:
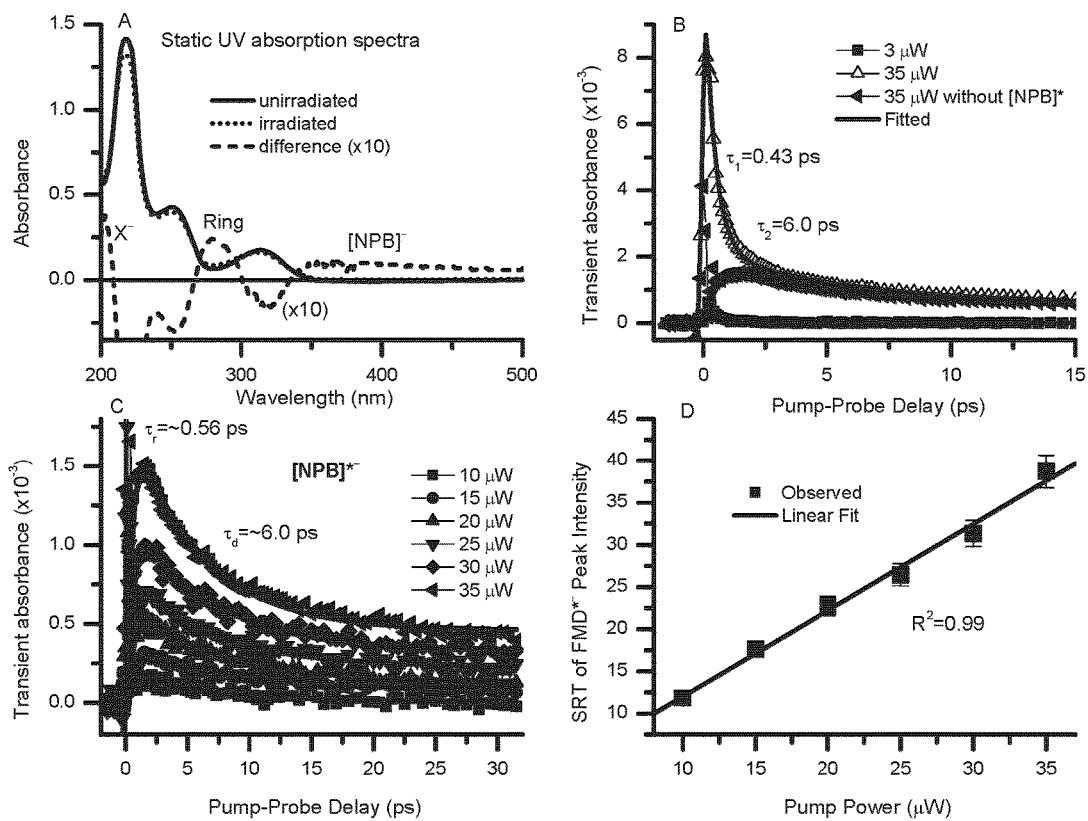
FIG. 3. Femtosecond (fs) laser spectroscopic observation of NPB*$^-$ resulting from the ultrafast DET reaction of a NPB compound (Compound B) with a weakly-bound electron $e_{wb}^-$. Here, $e_{wb}^-$ is readily generated by two-UV photolysis of a polar solvent molecule (e.g., H$_2$O) by a fs pump laser pulse. The generated electron goes rapidly through the p-like excited (weakly-bound) precursor state ($e_{wb}^-$) in the polar liquid with an ultrashort lifetime of about 0.5 picosecond, during which an effective DET reaction with a NPB compound can occur. A. Static electronic (UV) absorption spectra of the NPB solution, before and after extensive exposure to pump fs laser pulses at 350 nm. Their difference spectrum shows three visible absorption bands, which can reasonably be attributed to the stabilized [B(NH$_2$)$_2$X$_n$]$^-$ at 350-600 nm, the protonated de-halogenated aromatic ring at ~280 nm and the halogen anion at ~200 nm, respectively. B. Transient absorption kinetic traces of the NPB solution, pumped at 350 nm with lowest and high powers (3 μW and 35 μW, respectively corresponding to 0.006 and 0.07 μJ/pulse) and probed at 400 nm, after subtracting the kinetic trace for the pure solvent (ethanol). At the lowest pump power, only the neutral single-photon excited state NPB* exhibiting a rapid decay of $\tau_1$=0.43 ps was detected, where both states, NPB* and NPB*$^-$ ($\tau_2$=6.0 ps), were detected at the high pump power. C. The kinetic traces of NPB*$^-$ with various pump powers were obtained after subtracting the kinetic trace for the NPB* state that has a linear power dependence. The solid lines are the best fits to the obtained kinetic traces of NPB*$^-$, giving a rise time of ~0.56 ps, corresponding to the lifetime of $e_{wb}^-$, and a dissociative lifetime of ~6.0 ps. D. The square root of the NPB*$^-$ peak intensity versus pump power, confirming the quadratic NPB*$^-$ yield dependence on pump power to generate $e_{wb}^-$. Note that under the identical conditions, no DET reaction of BrdU/IdU with $e_{wb}^-$ was observed, indicating that the DET reaction of a NPB compound is much stronger than that of BrdU/IdU.

The reactivity of a NPB with a weakly-bound electron ($e_{wb}^-$) was studied by fs-TRLS measurements, as outline in Example 1. FIG. 3 shows that the DET reaction of compound B as an exemplary NPB was indeed highly effective, compared with those of halopyrimidines such as bromodeoxyuridine (BrdU) and iododeoxyuridine (IdU). The latters, which were tested as potential anti-cancer agents but failed in Phase III clinical trials [Prados et al., 1999], showed no DET reactions detected under the identical experimental conditions, probably due to the lack of an electron-transfer promoter in the structure of BrdU and IdU. This suggests that the present disclosed NPBs are highly promising as effective anti-cancer agents for chemotherapy of cancer.

In Vitro Toxicity Tests of NPB Anti-Cancer Compounds

Figure 4:
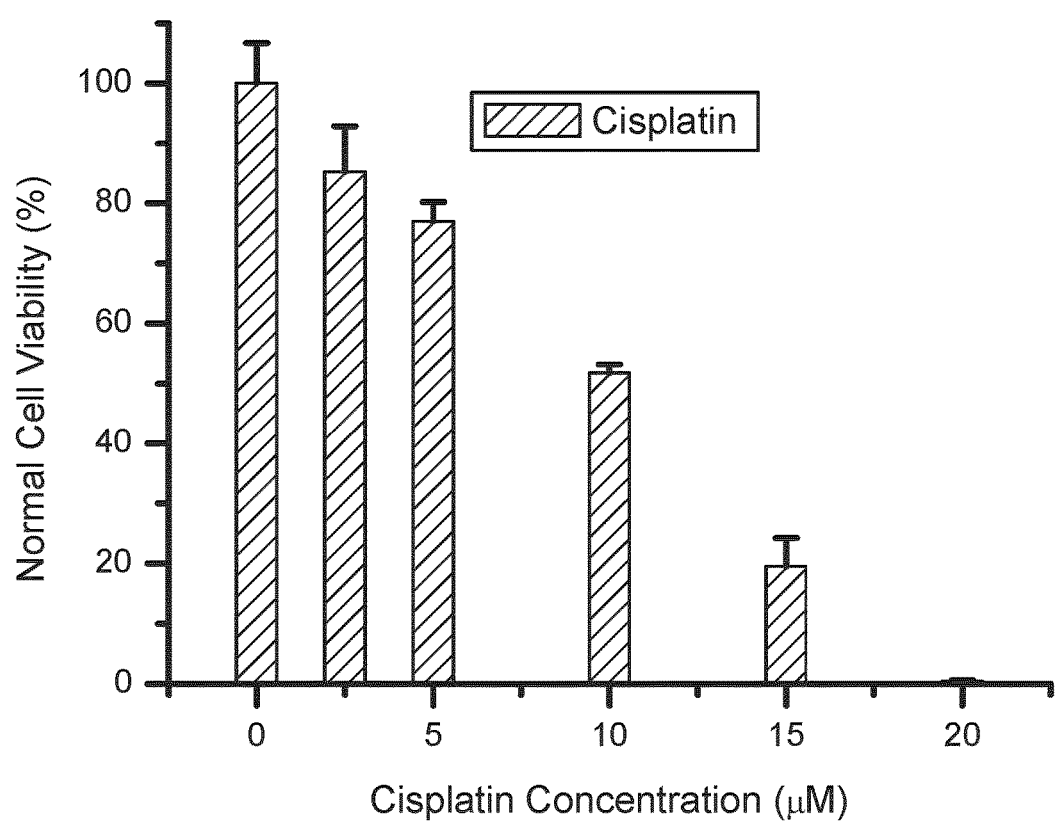
FIG. 4 illustrates cell survival rates of human normal cells (GM05757) after the 72-hr treatment of cisplatin with various concentrations. The viability of cells in 96-well plates was measured by MTT assay. This result confirms that cisplatin itself is highly toxic as a chemotherapeutic drug.
Figure 5:
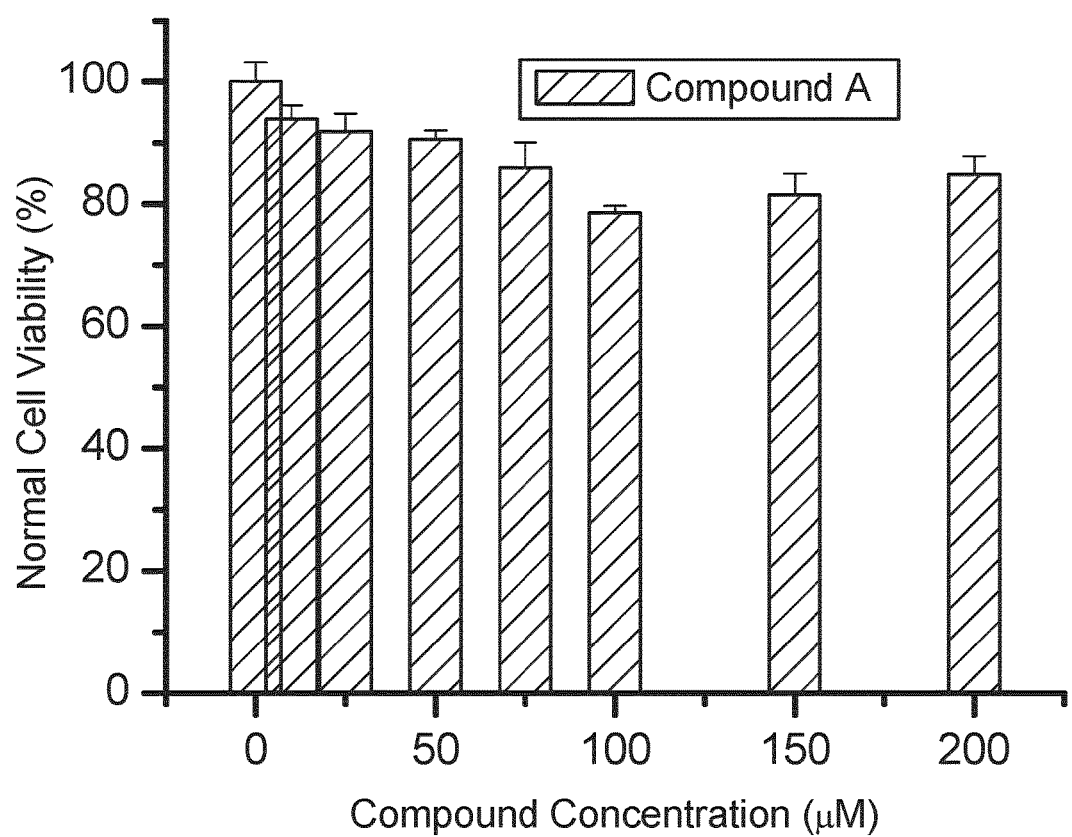
FIG. 5 illustrates cell survival rates of human normal cells (GM05757) after the 96-hr treatment of Compound A with various concentrations. The viability of cells in 96-well plates was measured by MTT assay. This result shows that Compound A itself shows little toxicity up to 200 μM.
Figure 6:
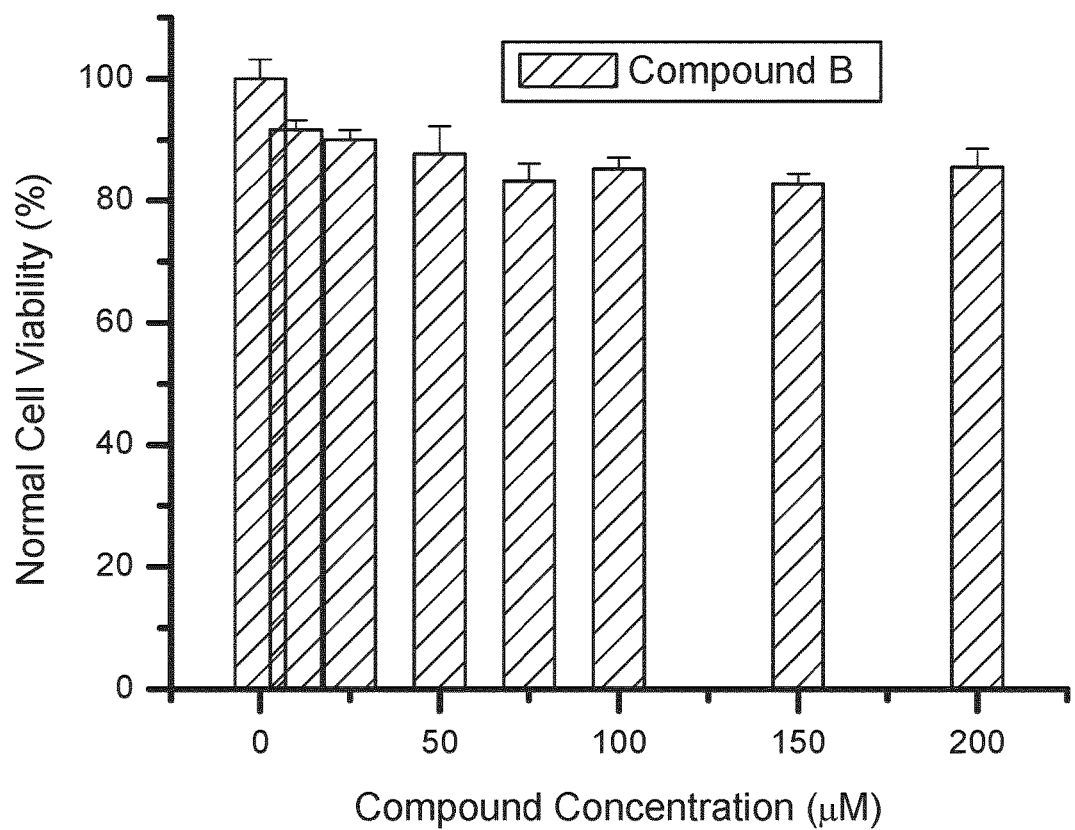
FIG. 6 illustrates cell survival rates of human normal cells (GM05757) after the 96-hr treatment of Compound B with various concentrations. The viability of cells in 96-well plates was measured by MTT assay. This result shows that Compound B itself shows little toxicity up to 200 μM.
Figure 7:
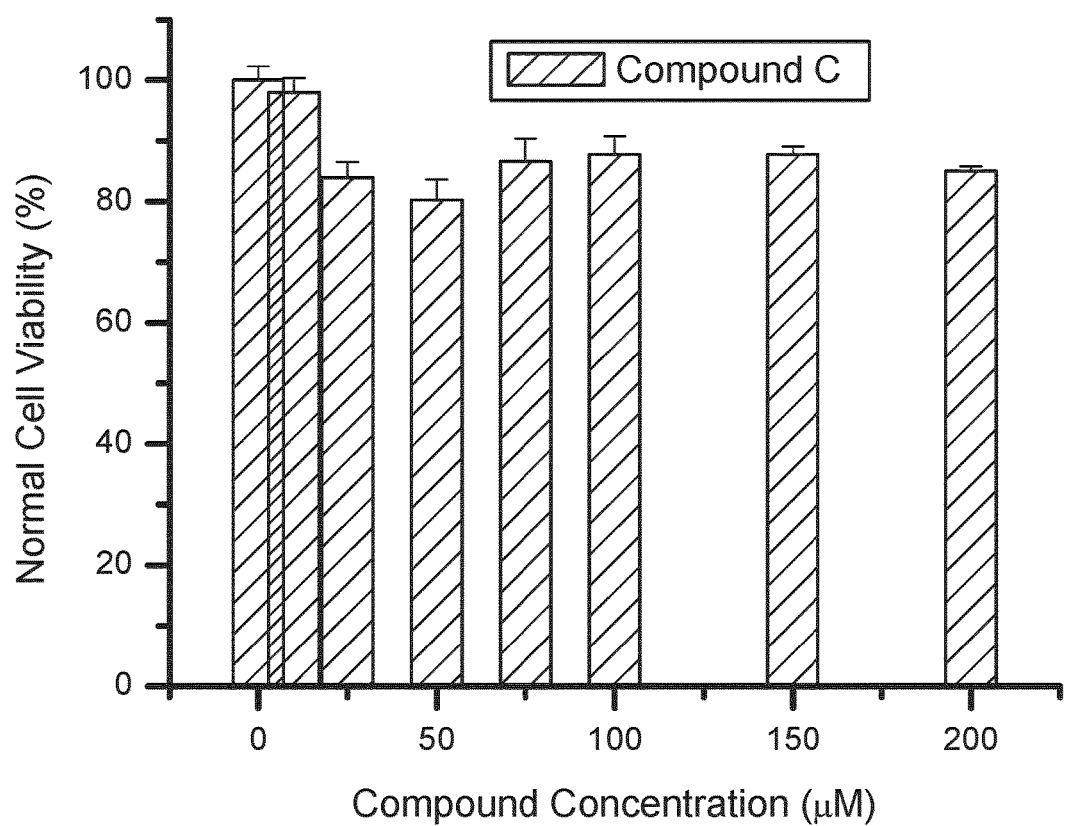
FIG. 7 illustrates cell survival rates of human normal cells (GM05757) after the 96-hr treatment of Compound C with various concentrations. The viability of cells in 96-well plates was measured by MTT assay. This result shows that Compound C itself shows little toxicity up to 200 μM.
Figure 8:
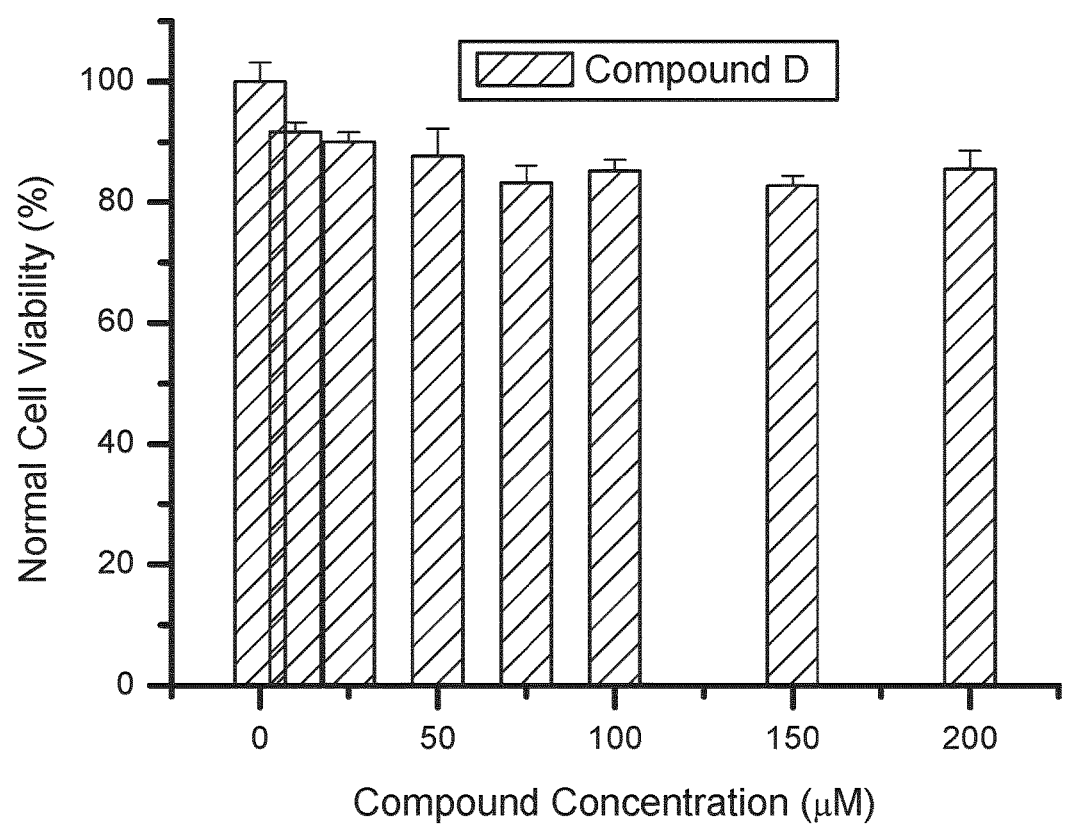
FIG. 8 illustrates cell survival rates of human normal cells (GM05757) after the 96-hr treatment of Compound D with various concentrations. The viability of cells in 96-well plates was measured by MTT assay. This result shows that Compound D itself shows little toxicity up to 200 μM.
Figure 9:
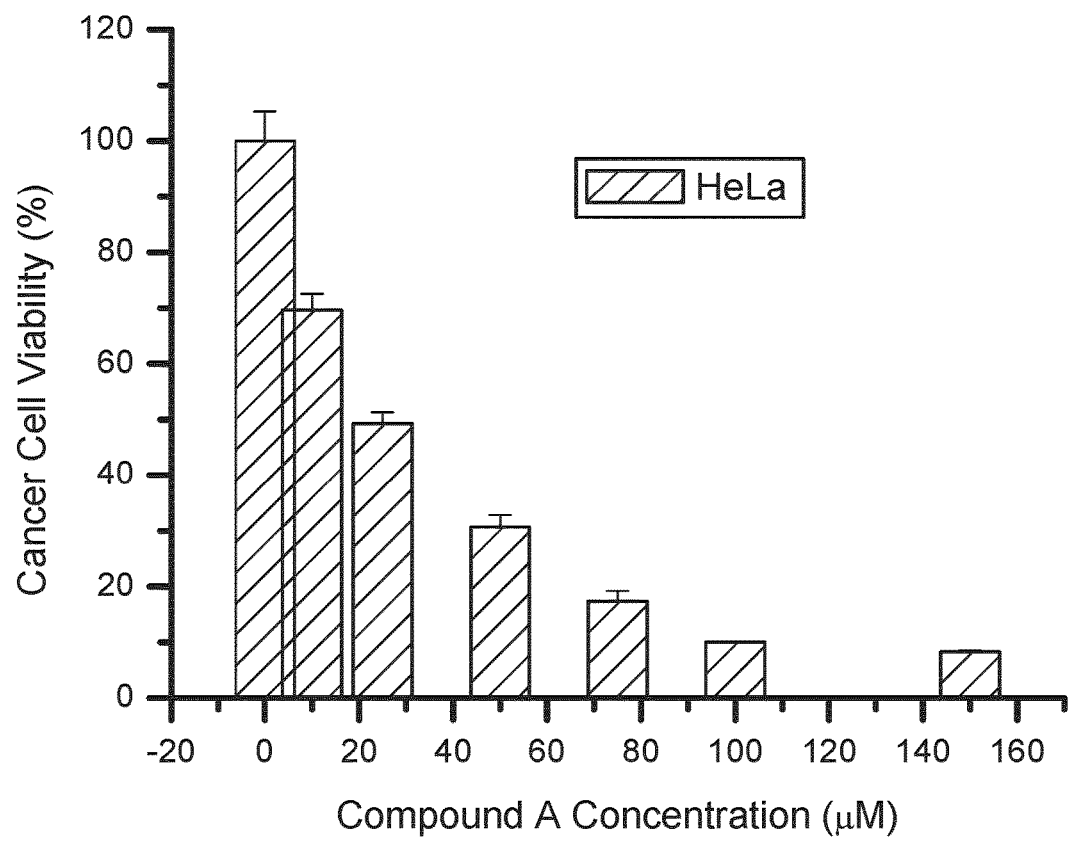
FIG. 9 illustrates cell survival rates of human cervical cancer (HeLa) cells after the 96-hr treatment of Compound A with various concentrations. The viability of the cells in 96-well plates was measured by MTT assay. A significant killing of cancer cells by Compound A was observed.
Figure 10:
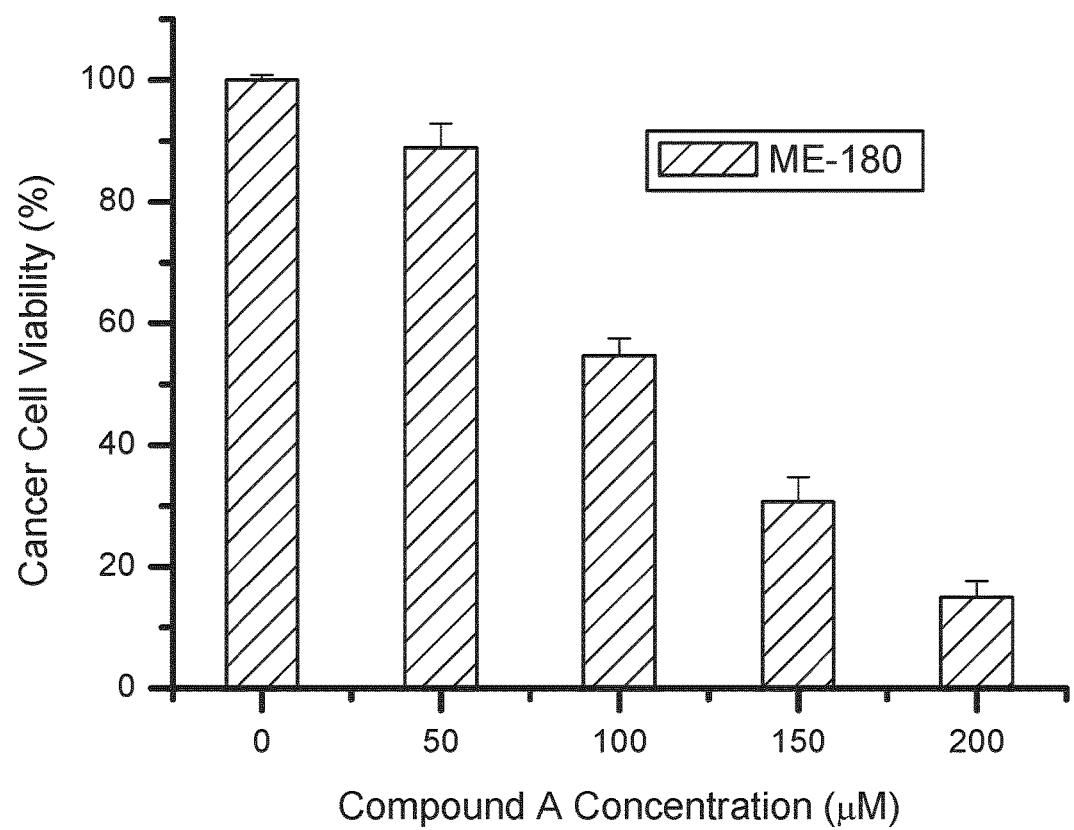
FIG. 10 illustrates cell survival rates of human cervical cancer (ME-180) cells after the 96-hr treatment of Compound A with various concentrations. The viability of the cells in 96-well plates was measured by MTT assay. A significant killing of cancer cells by Compound A was observed.
Figure 11:
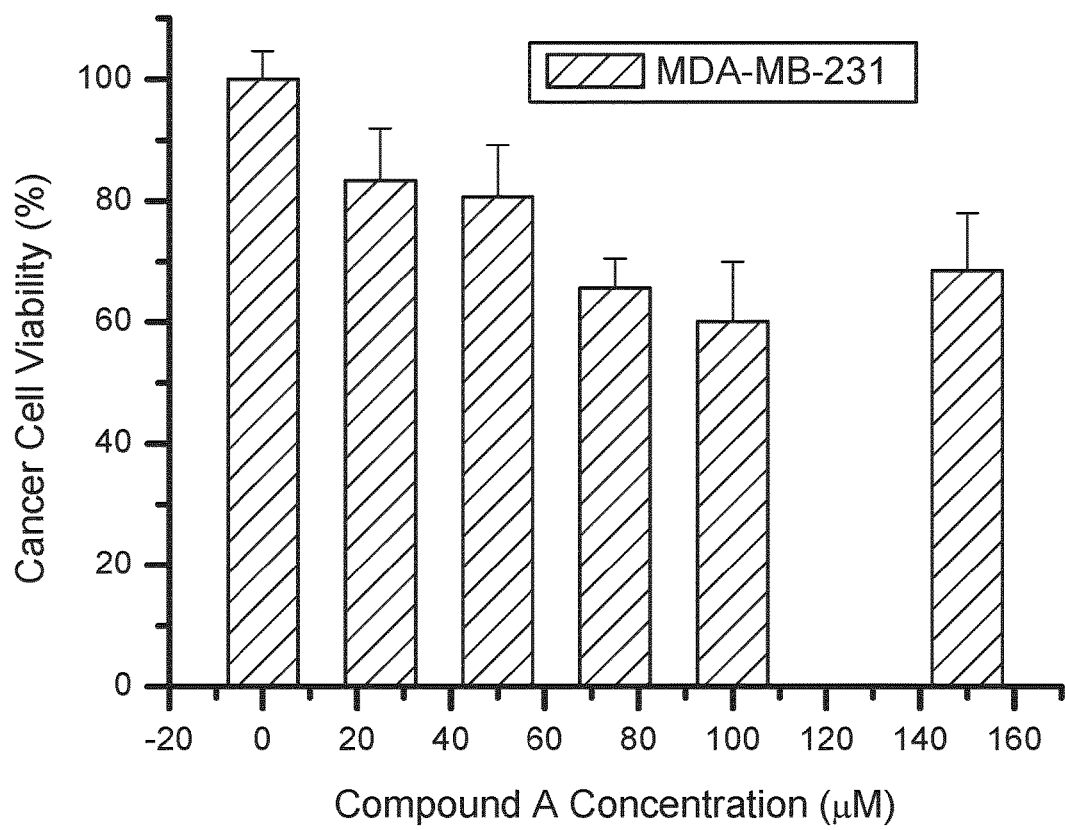
FIG. 11 illustrates cell survival rates of human breast cancer (MDA-MB-231) cells after the 96-hr treatment of Compound A with various concentrations. The viability of the cells in 96-well plates was measured by MTT assay. A significant killing of cancer cells by Compound A was observed.
Figure 12:
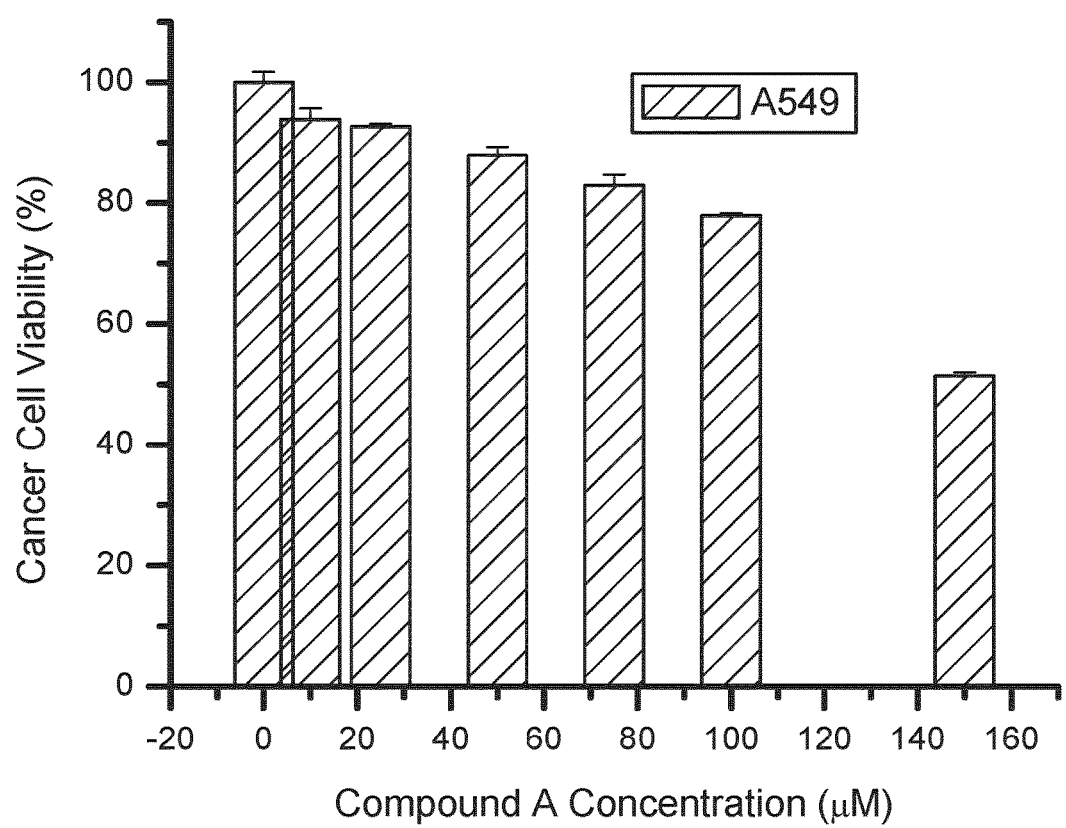
FIG. 12 illustrates cell survival rates of human lung cancer (A549) cells after the 96-hr treatment of Compound A with various concentrations. The viability of the cells in 96-well plates was measured by MTT assay. A significant killing of cancer cells by Compound A was observed.
Figure 13:
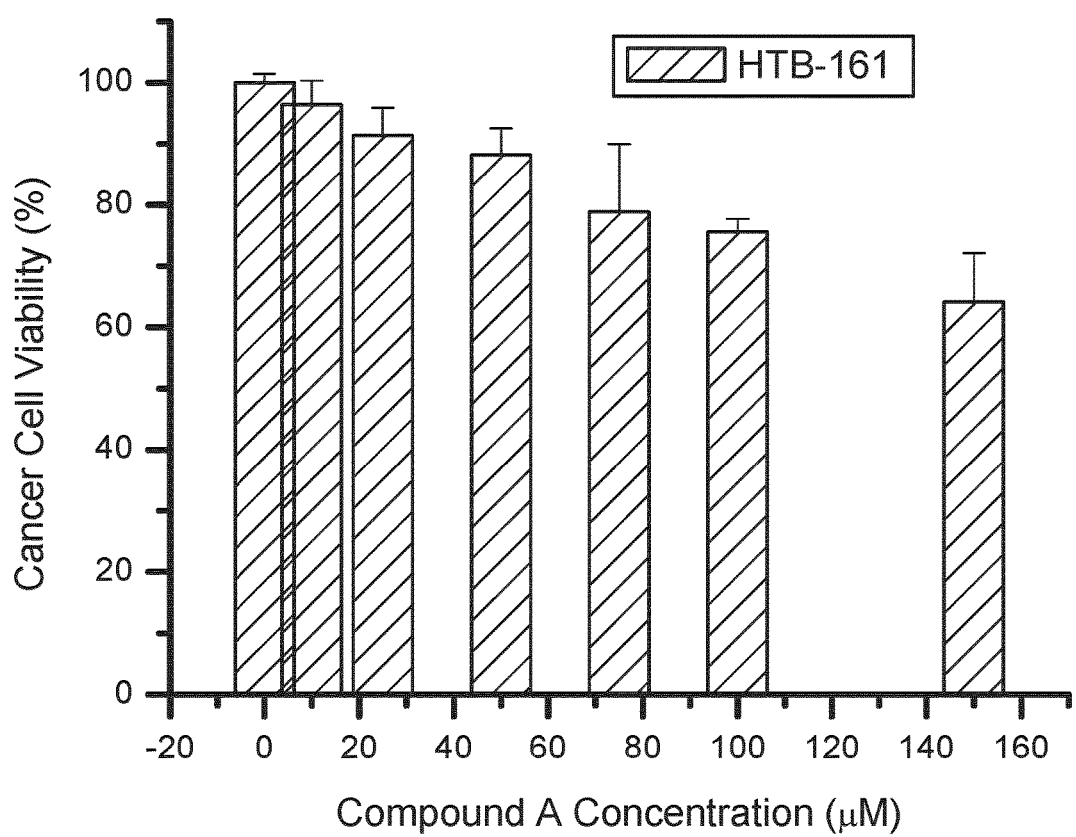
FIG. 13 illustrates cell survival rates of cisplatin-resistant human ovarian cancer (HTB-161) cells after the 96-hr treatment of Compound A with various concentrations. The viability of the cells in 96-well plates was measured by MTT assay. A significant killing of cisplatin-resistant cancer cells by Compound A was observed.
Figure 14:
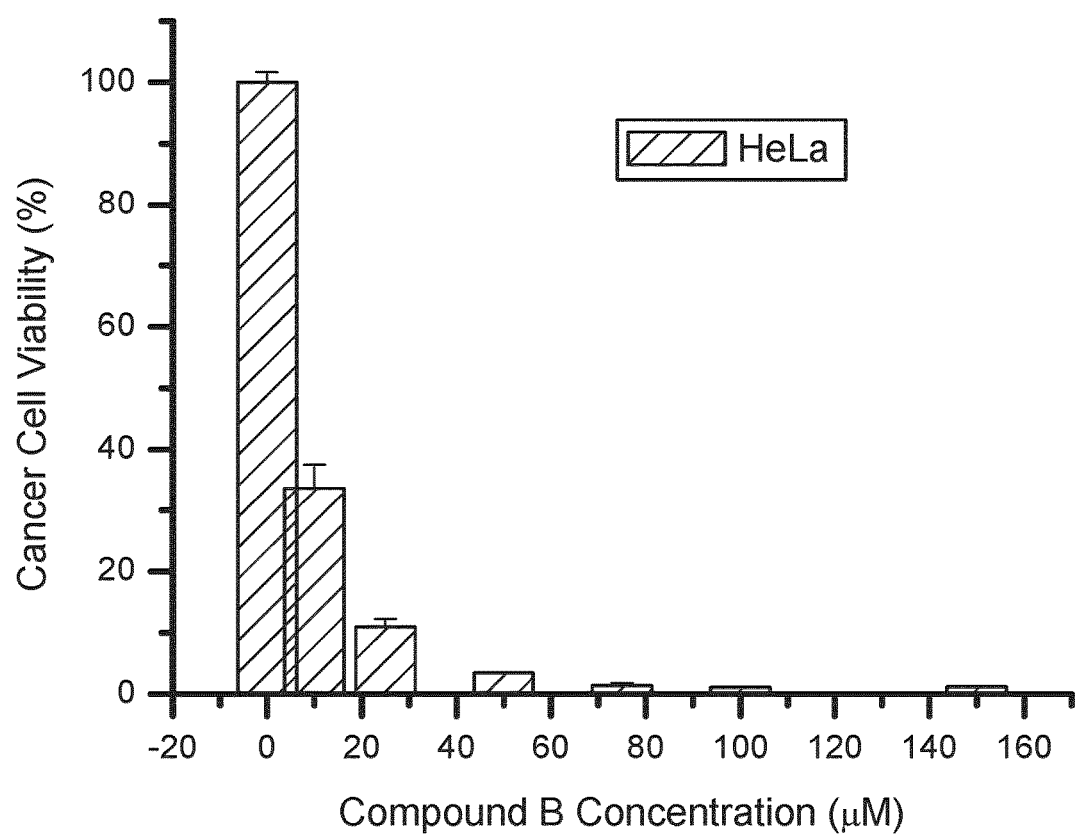
FIG. 14 illustrates cell survival rates of human cervical cancer (HeLa) cells after the 96-hr treatment of Compound B with various concentrations. The viability of the cells in 96-well plates was measured by MTT assay. A significant killing of cancer cells by Compound B was observed.
Figure 15:
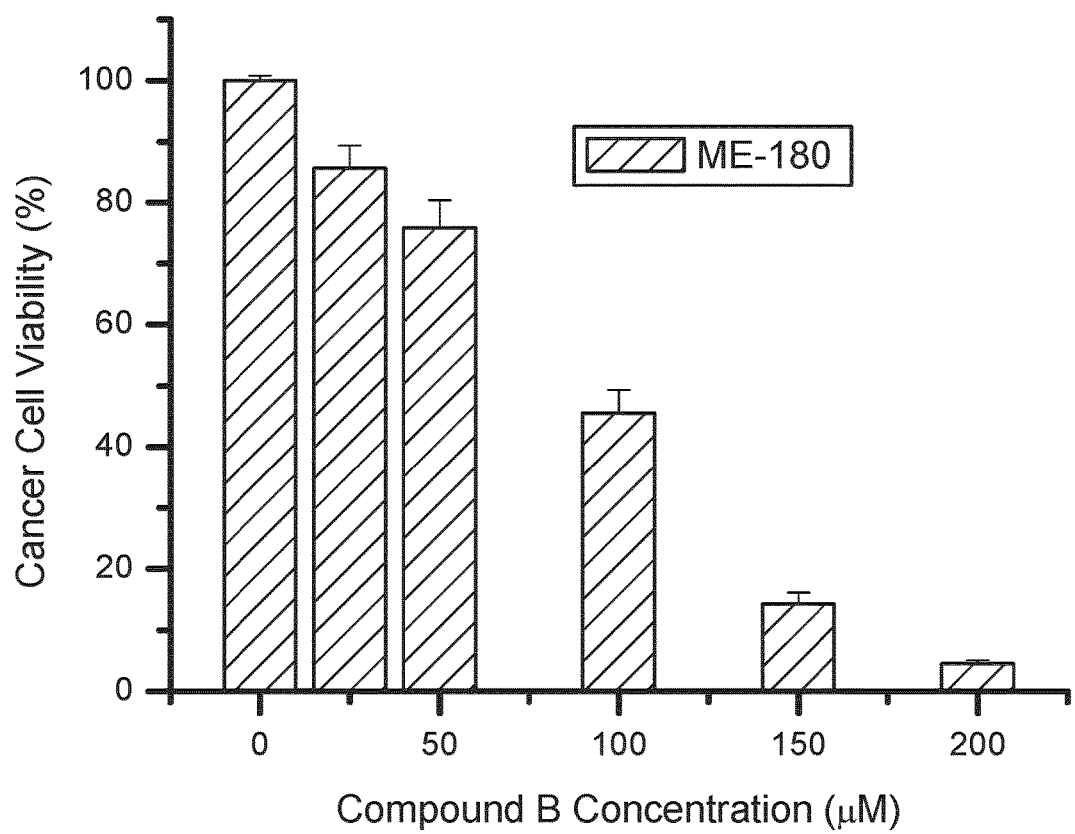
FIG. 15 illustrates cell survival rates of human cervical cancer (ME-180) cells after the 96-hr treatment of Compound B with various concentrations. The viability of the cells in 96-well plates was measured by MTT assay. A significant killing of cancer cells by Compound B was observed.
Figure 16:
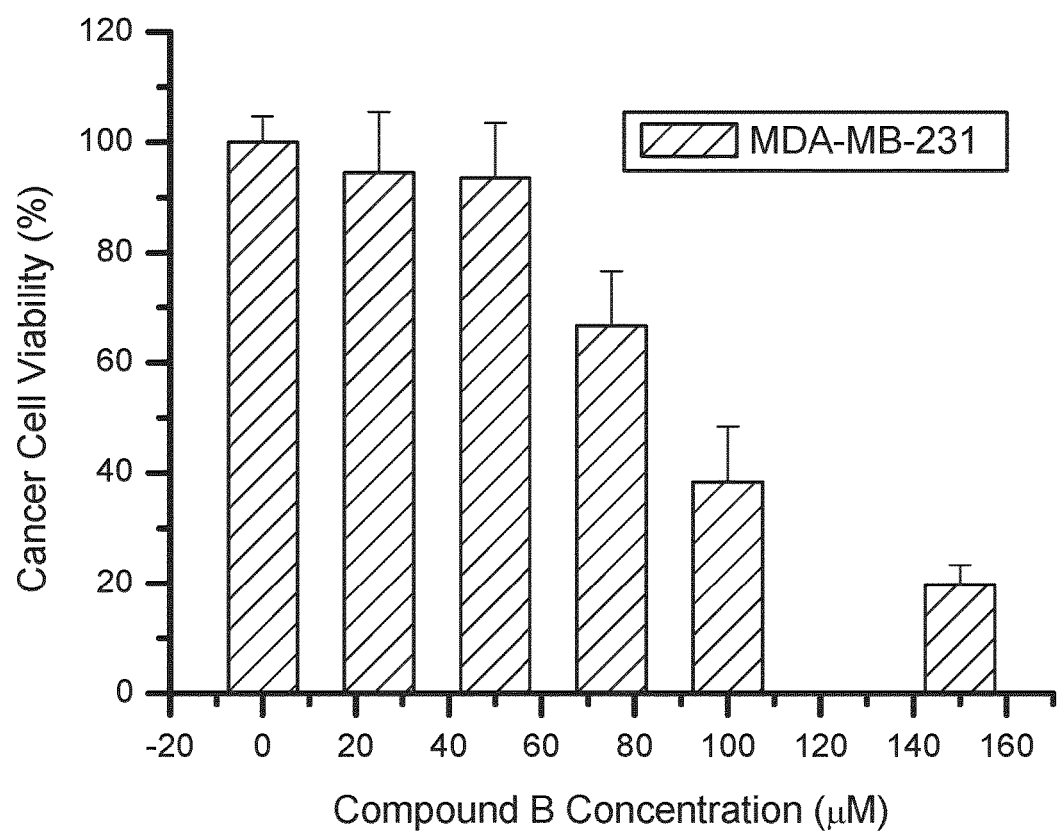
FIG. 16 illustrates cell survival rates of human breast cancer (MDA-MB-231) cells after the 96-hr treatment of Compound B with various concentrations. The viability of the cells in 96-well plates was measured by MTT assay. A significant killing of cancer cells by Compound B was observed.
Figure 17:
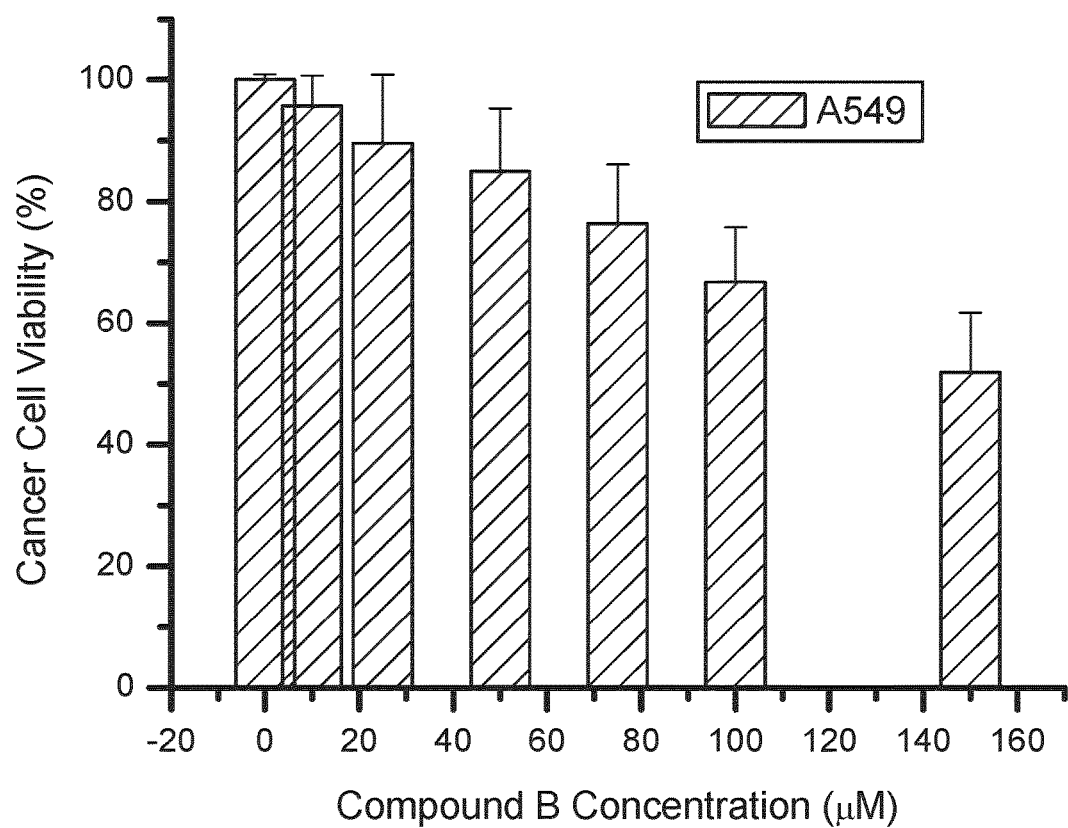
FIG. 17 illustrates cell survival rate of human lung cancer (A549) cells after the treatment of Compound B with various concentrations for 96 hr. A significant killing of cancer cells by Compound B was observed.
Figure 18:
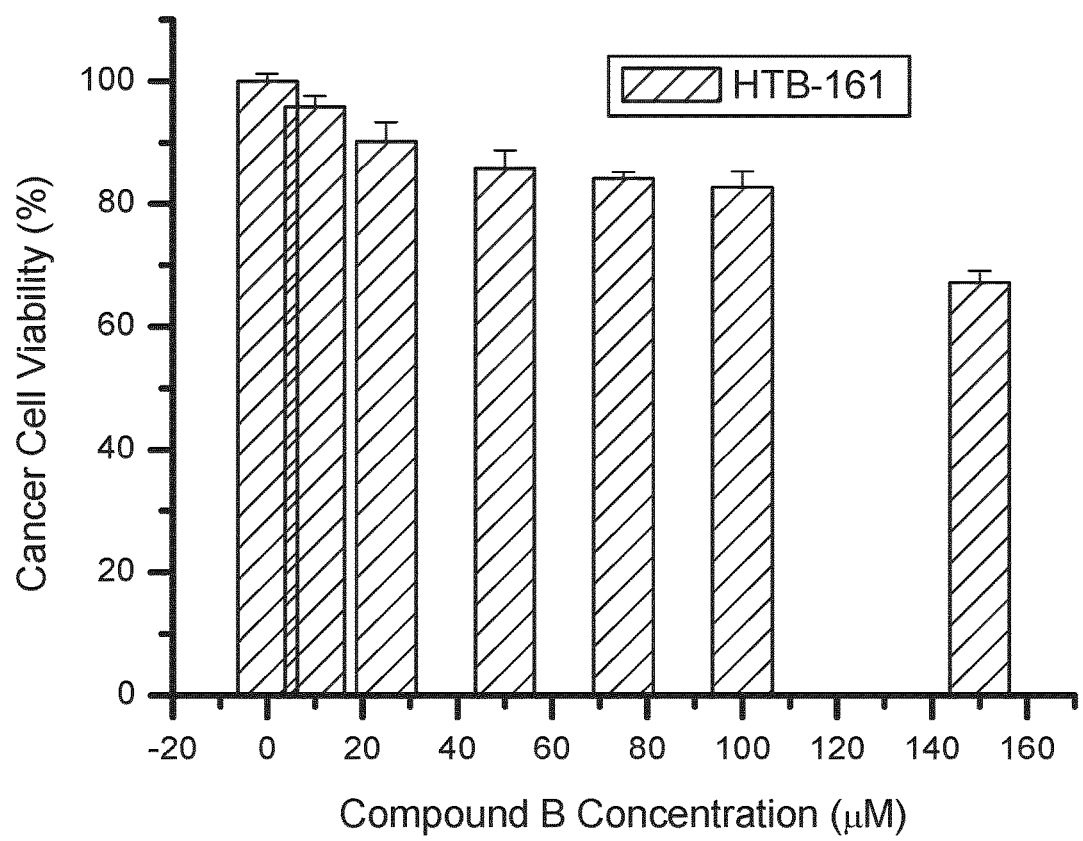
FIG. 18 illustrates cell survival rates of cisplatin-resistant human lung cancer (HTB-161) cells after the 96-hr treatment of Compound B with various concentrations. The viability of the cells in 96-well plates was measured by MTT assay. A significant killing of cancer cells by Compound B was observed.
Figure 19:
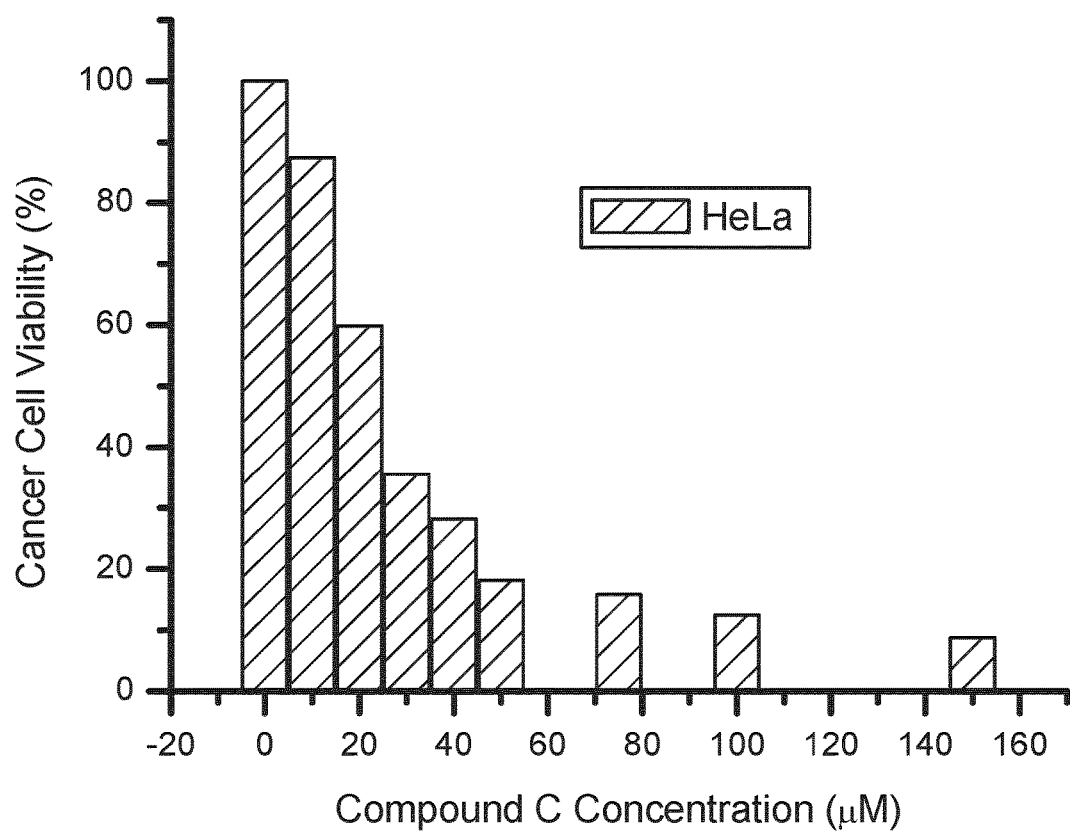
FIG. 19 illustrates cell survival rates of human cervical cancer (HeLa) cells after the 96-hr treatment of Compound C with various concentrations. The viability of the cells in 96-well plates was measured by MTT assay. A significant killing of cancer cells by Compound C was observed.
Figure 20:
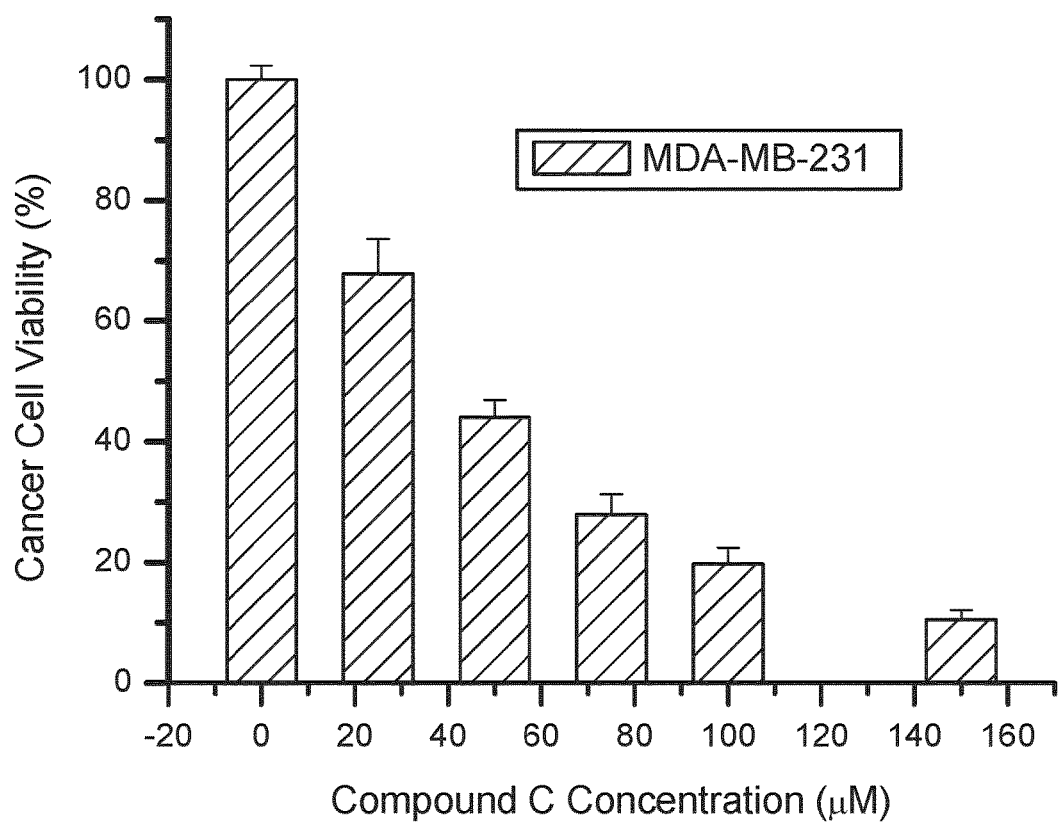
FIG. 20 illustrates cell survival rates of human breast cancer (MDA-MB-231) cells after the 96-hr treatment of Compound C with various concentrations. The viability of the cells in 96-well plates was measured by MTT assay. A significant killing of cancer cells by Compound C was observed.
Figure 21:
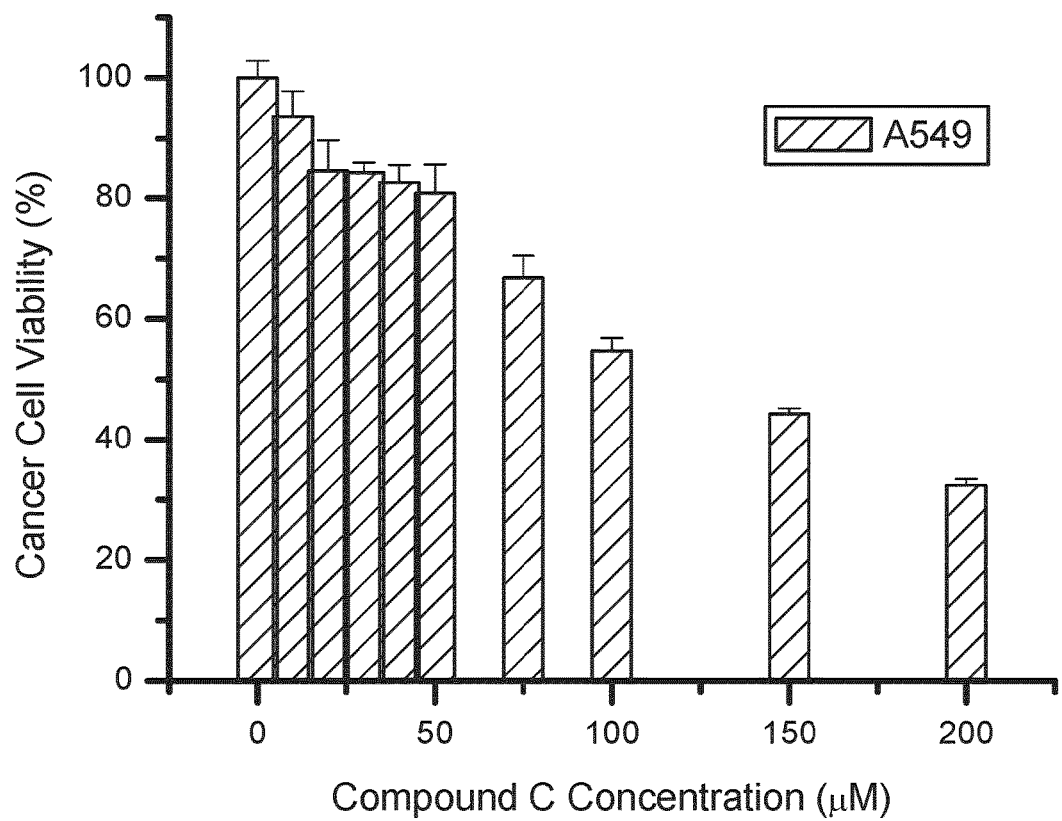
FIG. 21 illustrates cell survival rate of human lung cancer (A549) cells after the treatment of Compound C with various concentrations for 72 hr. A significant killing of cancer cells by Compound C was observed.
Figure 22:
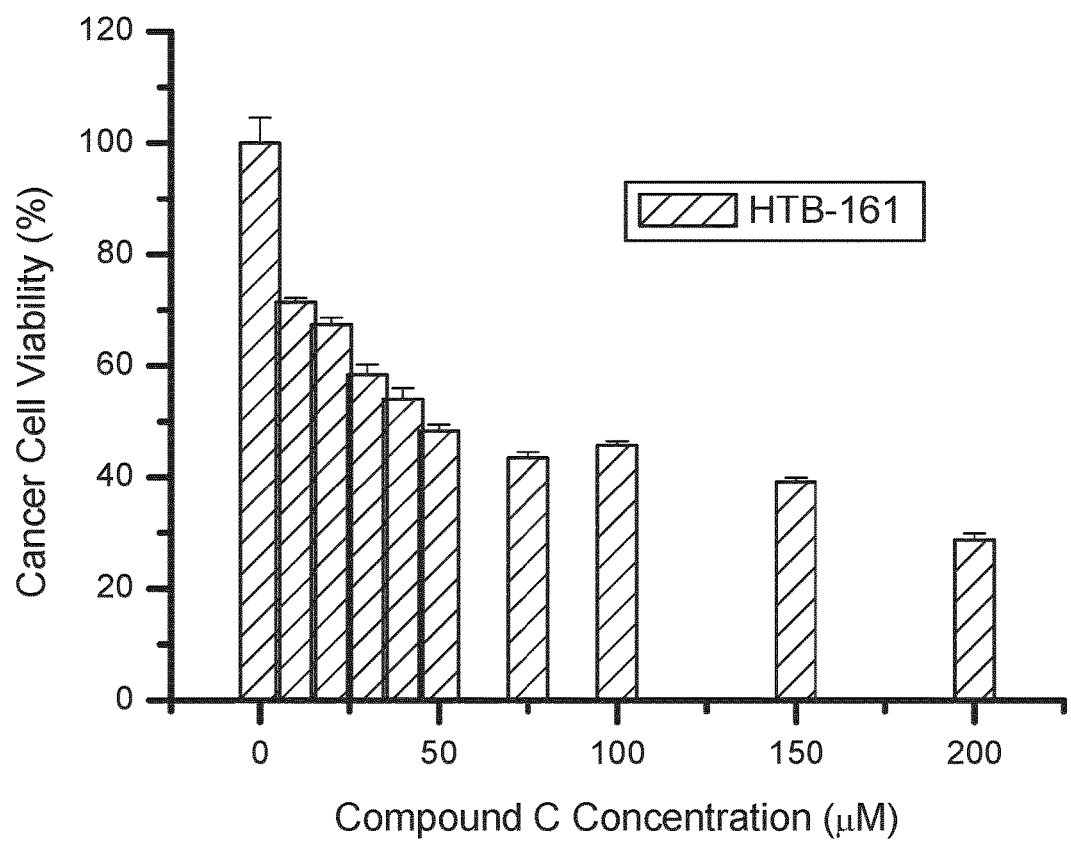
FIG. 22 illustrates cell survival rate of cisplatin-resistant human ovarian cancer (HTB-161) cells after the treatment of Compound C with various concentrations for 96 hr. A significant killing of cancer cells by Compound C was observed.
Figure 23:
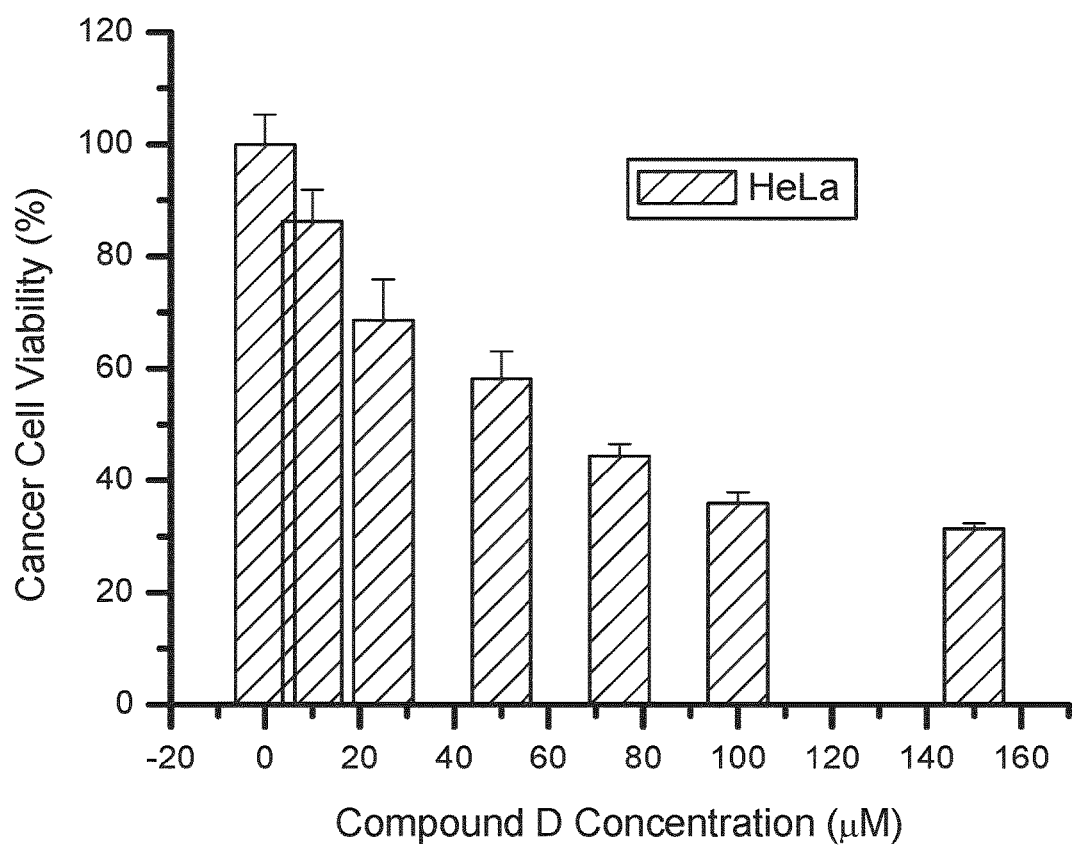
FIG. 23 illustrates cell survival rates of human cervical cancer (HeLa) cells after the 96-hr treatment of Compound D with various concentrations. The viability of the cells in 96-well plates was measured by MTT assay. A significant killing of cancer cells by Compound D was observed.
Figure 24:
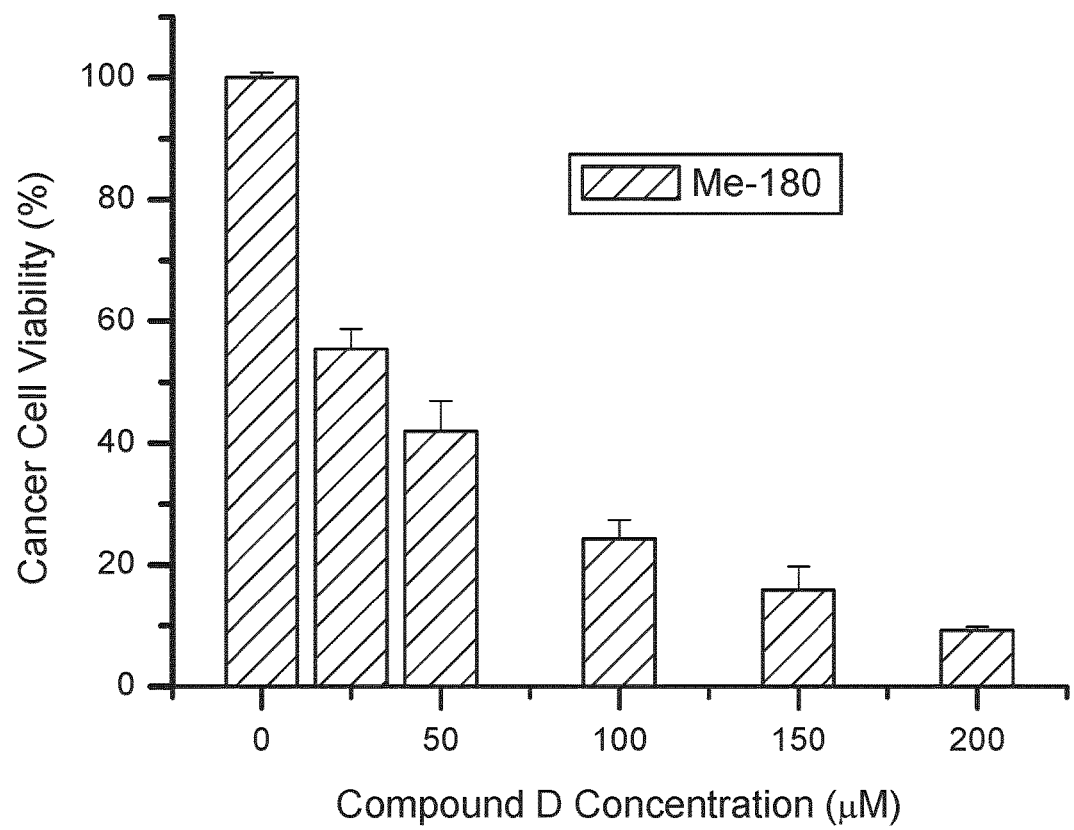
FIG. 24 illustrates cell survival rates of human cervical cancer (ME-180) cells after the 96-hr treatment of Compound D with various concentrations. The viability of the cells in 96-well plates was measured by MTT assay. A significant killing of cancer cells by Compound D was observed.
Figure 25:
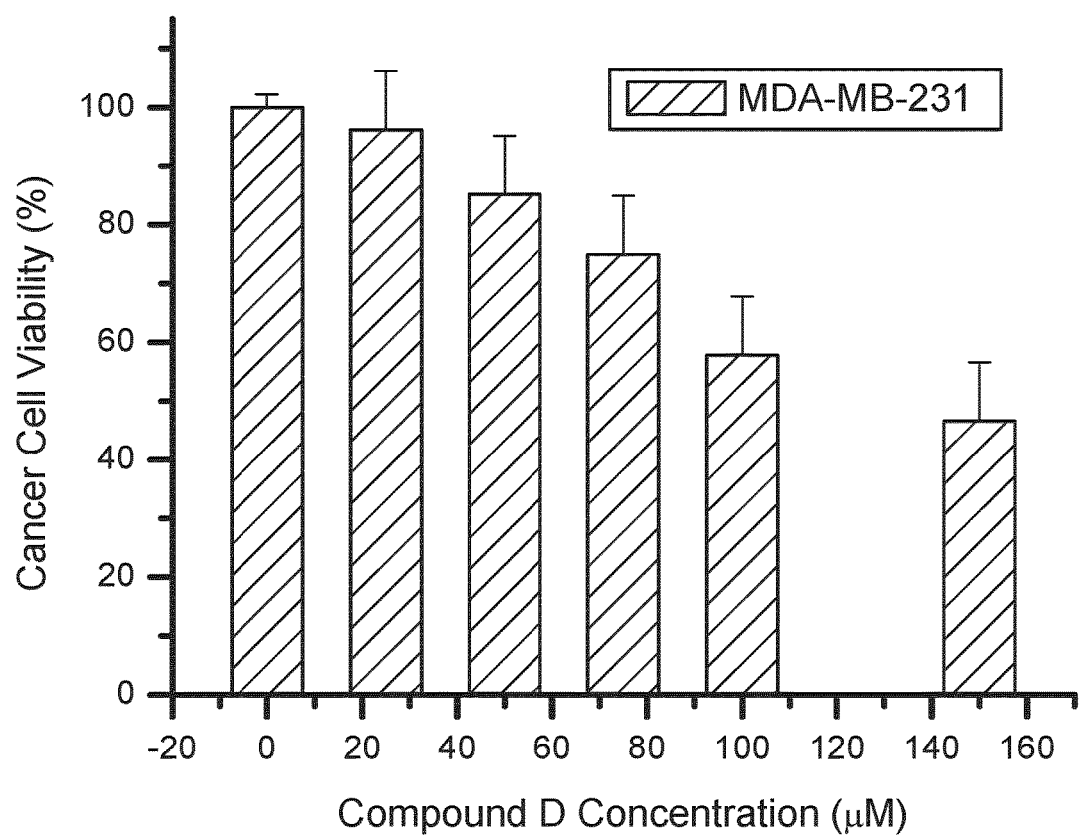
FIG. 25 illustrates cell survival rates of human breast cancer (MDA-MB-231) cells after the 96-hr treatment of Compound D with various concentrations. The viability of the cells in 96-well plates was measured by MTT assay. A significant killing of cancer cells by Compound D was observed.
Figure 26:
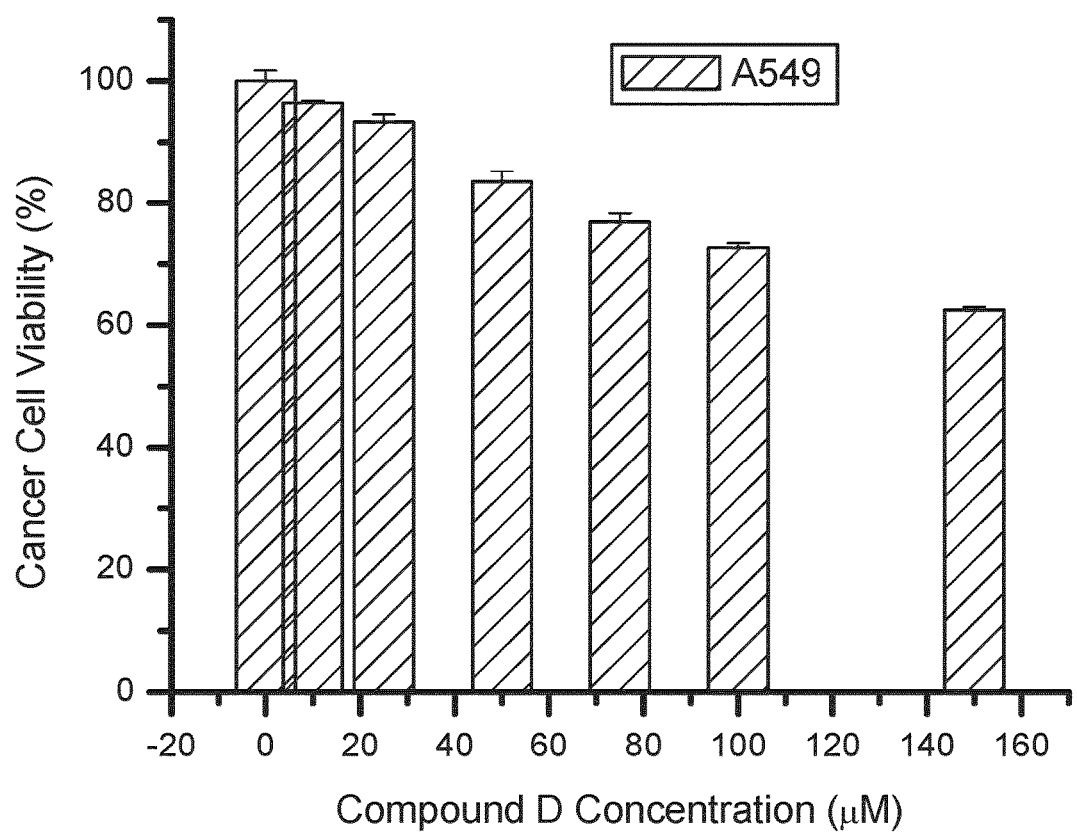
FIG. 26 illustrates cell survival rate of human lung cancer (A549) cells after the treatment of Compound D with various concentrations for 96 hr. A significant killing of cancer cells by Compound D was observed.
Figure 27:
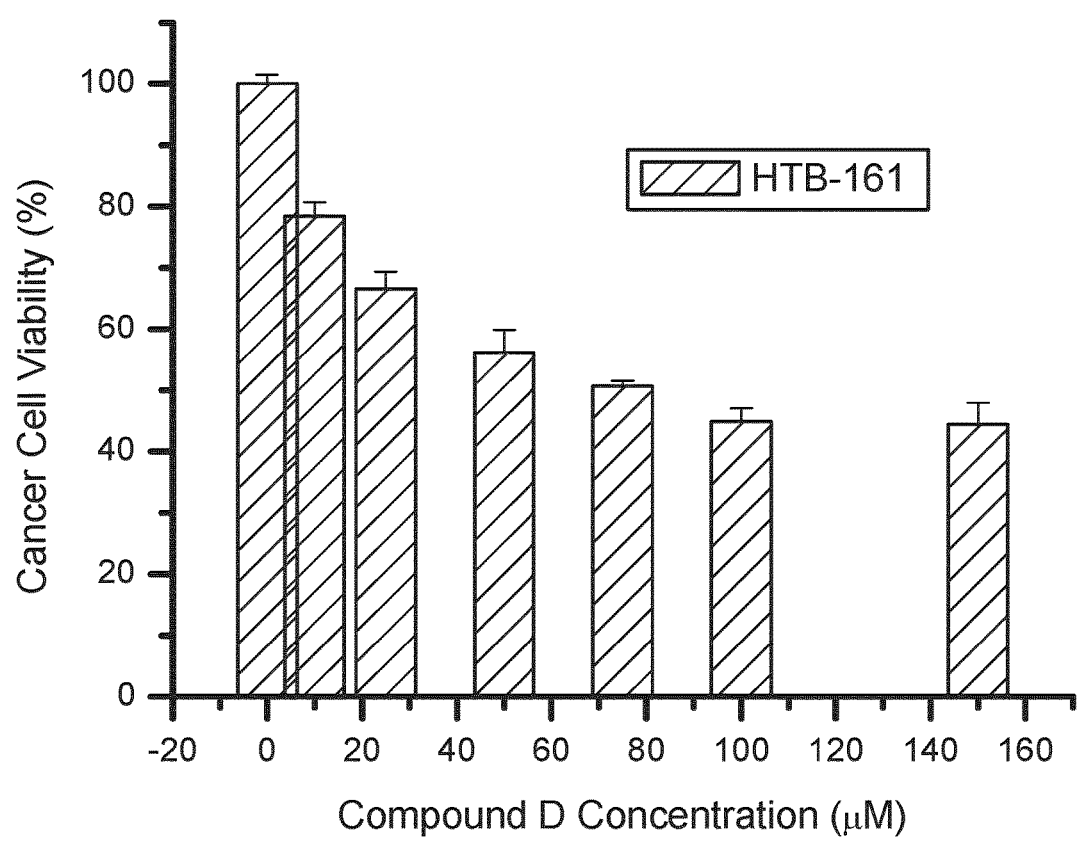
FIG. 27 illustrates cell survival rates of cisplatin-resistant human ovarian cancer (HTB-161) cells after the 96-hr treatment of Compound D with various concentrations. The viability of the cells in 96-well plates was measured by MTT assay. A significant killing of cisplatin-resistant cancer cells by Compound D was observed.

The in vitro toxicity of cisplatin or NPB anti-cancer compounds alone was investigated in human (skin) normal cells (GM05757), as outlined in Example 2. The GM05757 cell line has been widely used as human normal cells in cancer research, particularly in testing new anti-cancer agents [Choudhury et al. 2009]. FIG. 4 shows that the normal cells were effectively killed by the 72-hr treatment of cisplatin in a dose-dependent manner with a measured IC50 of about 10 µM (at which the cell survival rate is 50% with respect to untreated cells), confirming that cisplatin is indeed highly toxic as a chemotherapeutic drug. In contrast, the results plotted in FIGS. 5-8 show that NPB anti-cancer compounds, Compounds A, B, C and D, had essentially no toxicity toward normal cells in doses up to 200 µM for the treatment up to 96 hr. Thus, these NPBs are expected to induce few or no toxic side effects, in contrast to the heavy-metal (Pt)-based chemotherapeutic drug (cisplatin) in animals and humans. The viability of cells was measured by MTT assay, one of the most commonly used cell viability assays. This method involves the conversion of MTT (3-(4, 5-dimethylthiazol-2-yl)-2,5-diphenyltetrazolium bromide) to an insoluble formazan by metabolically-active cells (live cells). Using a solubilizing agent, the formazan is dissolved and its absorbance measured, giving indication to the number of cells that survive. This is a well-established quantitative method that is rapid in terms of the required drug treatment time as well as the total protocol time compared to the clonogenic assay, which measures cell survival on the long-term scale.

In Vitro Anti-Cancer Effect Tests of NPB Anti-Cancer Compounds

The in vitro anti-cancer effects of NPBs were investigated in human cervical cancer (HeLa or ME-180), breast cancer (MDA-MB-231) and lung cancer (A549) cell lines, as well as cisplatin-resistant human ovarian cancer (NIH:OVCAR-3, HTB-161) cell line, as outlined in Example 3. FIGS. 9-27 show cell survival rates of various human cancer cells after the treatment with each NPB at various concentrations for 96 hr. These results show that Compounds A, B, C and D led to effective killing of cancer cells in a dose dependent manner. Significant anti-cancer effects of NPBs were clearly observed. For example, nearly all cervical cancer cells (ME-180) or breast cancer cells (MDA-MB-231) were killed with the presence of about 150-200 µM Compound B or C or D, which showed no toxicity against human normal cells.

Figure 28:
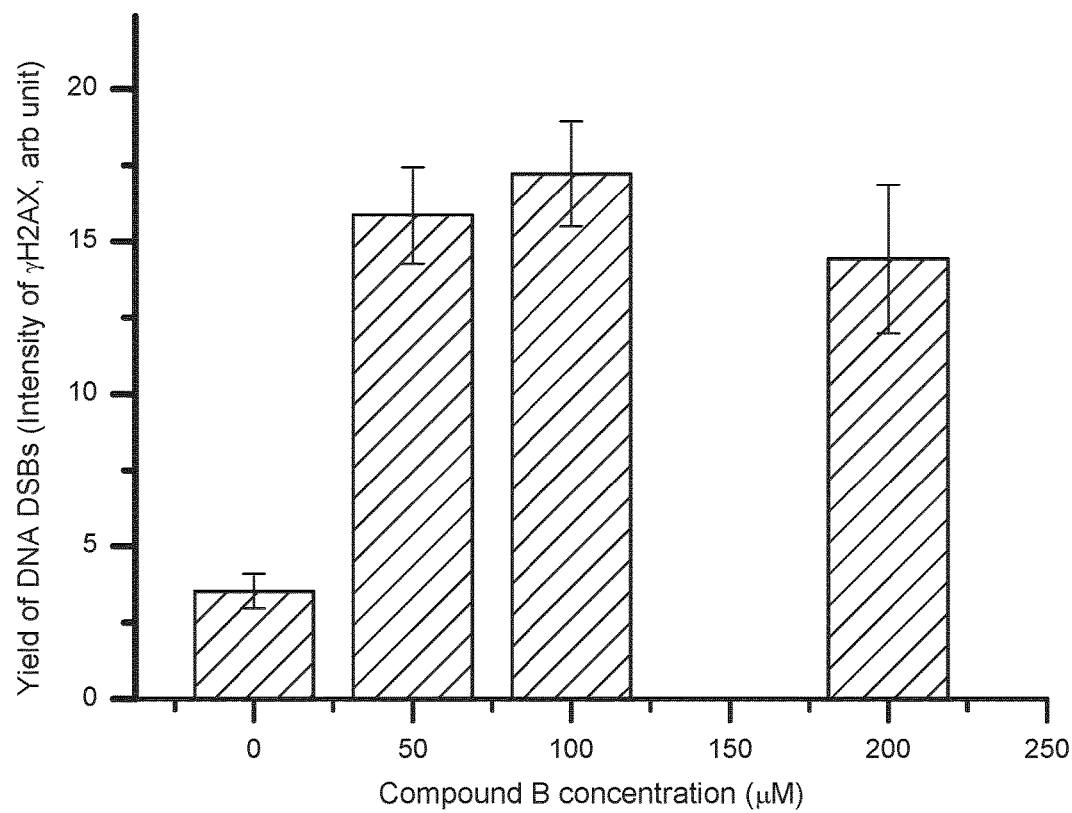
FIG. 28 shows the yield of DNA double-strand breaks (DSBs) (the γ-H2AX intensity) in ME-180 cells versus compound B concentration. ME-180 cells were treated with various concentrations of Compound B for 12 hours at 37° C., 5% $CO_2$. Imaging of double-strand breaks (DSBs) in human cervical cancer (ME-180) cells was obtained using the HCS DNA Damage Kit. The yields of DNA DSBs versus Compound B concentration were obtained by quantitative analyses of activated γ-H2AX using an Image J software. The results show that a significant amount of DNA DSBs was observed in the ME-180 cells treated with Compound B.
Figure 29:
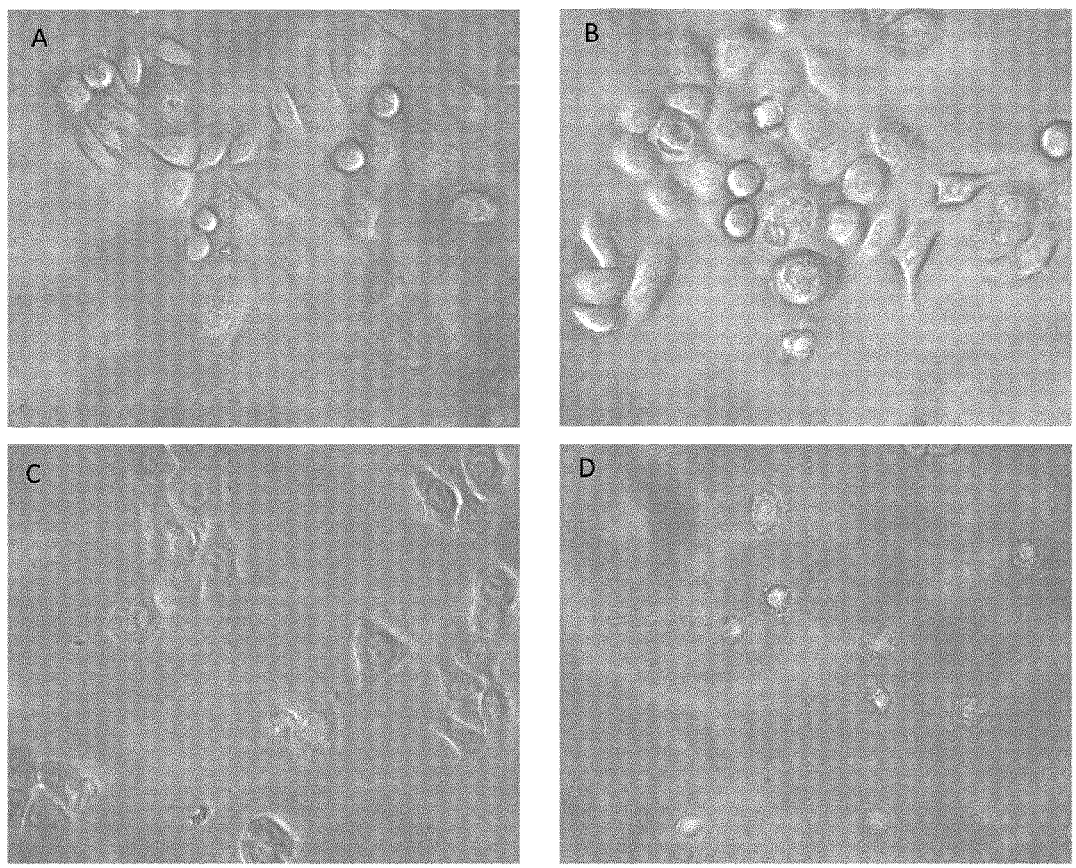
FIG. 29 shows representative images of human cervical cancer (ME-180) cells undergoing activation of caspases and apoptosis induced by the treatment of 0-200 μM compound B for 48 h, as detected by the CellEvent™ Caspase-3/7 Green Detection Kit (Invitrogen) using fluorescence microscopy: A. Control (0 μM); B. 50 μM; C. 100 μM; D. 200 μM. The apoptotic cells with activated caspases were represented by green fluorescence. Although the green fluorescence in the black & white images shown here is invisible, nuclear condensation, which is typical of late-stage apoptosis, is clearly seen. It is shown that Compound B at 200 μM caused a significant population (≥60%) of apoptotic cells.

In Vitro DNA Double-Strand Break and Apoptosis Tests of NPB Anti-Cancer Compounds The DNA double-strand breaks (DSBs) and apoptosis induced by Compound B as an exemplary NPB compound were investigated in human cervical cancer (ME-180) cell line, as outlined in Examples 4 and 5. The DNA DSBs and apoptosis in the treated cancer cells were detected by the γH2AX DNA damage assay and the CellEvent™ Caspase-3/7 Green Detection Kit (both were purchased from Invitrogen), respectively. FIG. 28 shows that Compound B induced a significant amount of DNA DSBs in the treated cancer cells, while FIG. 29 shows that it also correspondingly resulted in a significant percent of apoptosis in the cancer cells treated by 0-200 µM compound B.

The in vitro results presented herein strikingly demonstrate that the presence of an NPB compound effectively kills tumor cells but no normal cells by inducing significant DNA DSBs and apoptosis in cancer cells. Thus, the NPBs are expected to generate a sufficient anti-cancer effect while inducing minimal or no toxic side effects in animals and humans.

In Vivo Anti-Cancer Effects of NPB Anti-Cancer Compounds

The in vivo anti-cancer effects of Compound B, as an exemplary NPB compound, were investigated in the xenograft mouse tumor model of human cervical cancer (ME-180), as outlined in Example 6. The administration of Compound B significantly suppressed tumor growth, compared with the control group receiving no compounds in the tumor model, as can be seen from the tumor (volume) growth curves shown in FIG. 30. All of these results show that Compound B resulted in a significant growth inhibition and regrowth delay of the tumor in mice. Given that only a small daily dose (7 mg/kg, equivalent to an estimated concentration of about 50 µM in mice) of compound B used and that Compound B has minimal overall and acute toxicity at concentrations up to 200 µM, it is predicted that these results can be extrapolated to a larger compound dose or more frequent treatments so that a maximal therapeutic effect can be achieved.

In Vivo Toxicity Studies of NPB Anti-Cancer Compounds

Figure 31:
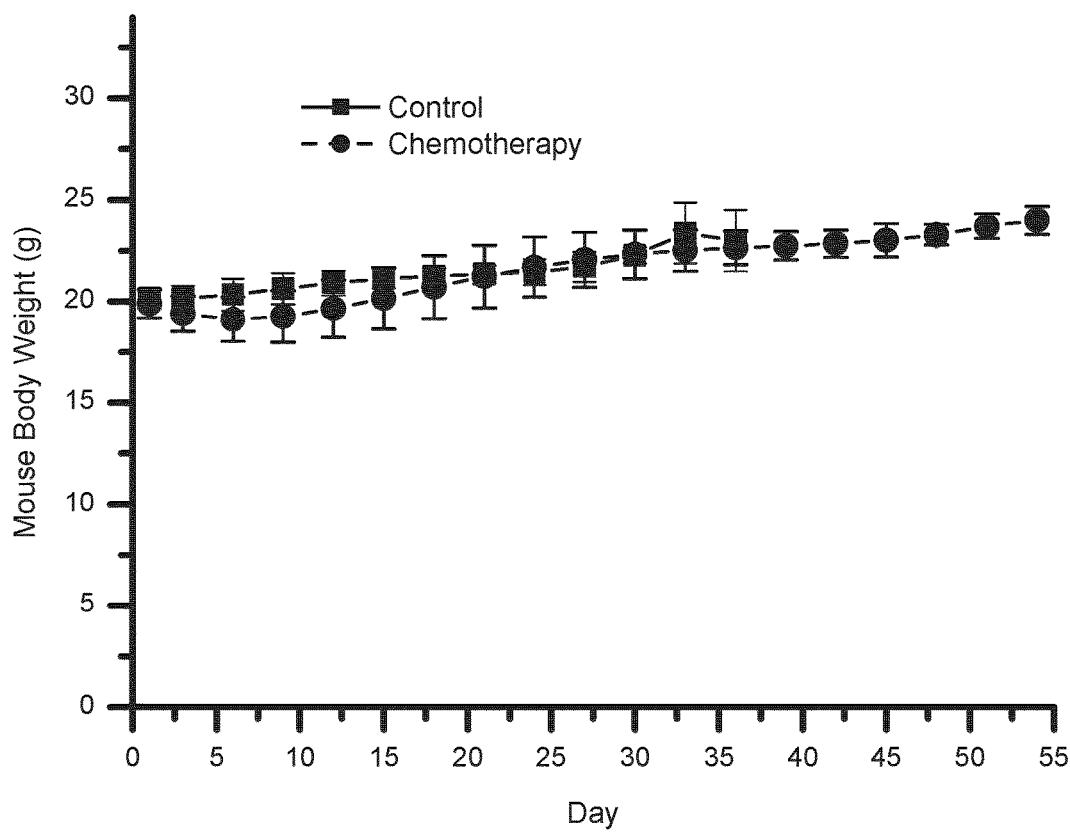
FIG. 31 shows mouse weight variation for the treatment of Compound B at 7 mg/kg given daily for 5 days. There is no significant change between the control group and the treated group, indicating that Compound B has no overall toxicity.

The overall drug toxicity was studied in 6-8 week SCID mice through a survival assay and body weight measurements, and the acute drug toxicity was measured through the following parameters: blood collection and histology, as outlined in Example 7. The hepatotoxicity (ALT, ALP, total bilirubin), nephrotoxicity (blood urea, creatinine), and electrolytes (Na, K, Cl) were analyzed by biochemical methods or HPLC-mass spectroscopy. In the present studies, Compound B as an exemplary NPB compound was intentionally administered by IP injection into mice at 0, and 7 mg/kg daily for 5 days due to the non-toxicity observed in vitro cell line experiments. Mice were observed for any physical toxicity. At the end of the study, whole organs were harvested in order to assess liver, and kidney toxicity. Blood was also collected. FIG. 31 shows that there was no effect on the weight of mice with time, i.e., Compound B exhibited no physical toxicity. Moreover, the results plotted in FIG. 32 show that Compound B even given at the high dose (5 day×7 mg/kg/day=35 mg/kg) induced no observable acute toxicity, i.e., no hepatotoxicity, no nephrotoxicity, and no changes in electrolytes.

It is believed that the in vitro and in vivo results from the Examples provided herein can be extrapolated to other compounds and combinations, cancer cells, cancer models and human cancers beyond those exemplified. With the information provided herein, a rational approach can be used to identify other new anti-cancer agents besides those exemplified herein that can be used in chemotherapy to generate their anticancer effects. Various screening assays known to those skilled in the art can be used to assess the effect of a particular agent, as can the in vitro and in vivo experiments set forth in the Examples. Those agents demonstrating anti-cancer effects will be particularly preferred, as well as those that do not result in toxic side effects compared to treatment with the Pt-based anticancer agents. This rational approach to identifying effective anti-cancer agents represents an efficient and economical alternative to random screening assays.

Skilled professionals will readily be able to determine the effective amounts required for the chemotherapy in vivo, e.g. so as to achieve the desired anticancer effect while having minimal toxic side effects. Effective dosages may vary depending on the type and stage of cancer, the route of administration, the treatment regimen, among other factors. Studies can furthermore be conducted by skilled professionals in order to determine the optimal drug dose to be used.

One advantage of the NPBs disclosed herein is that the disclosed DET reaction mechanism is designed to be preferentially active at tumor cells. This is in contrast to the case in normal cells, where a NPB will have a low reactivity, thus the DET will not occur or its reaction efficiency will be significantly lowered in normal tissue due to the lack of a reductive intracellular environment [Lu et al., 2013]. Thus the disclosed compounds will make a naturally targeted chemotherapy of multiple types of cancers, including (but not limited to) as cervical, ovarian, breast, lung, prostate, brain and spinal cord, head and neck, liver, stomach, leukemia, and colorectal cancers.

Some desired characteristics of the NPBs include one or a combination of the following: (1) biocompatible; (2) effective reaction with weakly-bound electrons; (3) effective killing of cancer cells so that certain doses can be used; (4) inert to normal cells and thus minimal toxicity (ideally, substantially non-toxic) at doses to be administered; (5) reactive in a reductive or hypoxic tumor environment; (6) preferentially reactive with cancer cells; (7) capable of entering a cell and preferably nucleus; and/or (8) applicable to multiple types of tumors.

Applying the principles disclosed herein, persons of skill in the art will be able to identify anti-cancer compounds that can induce the anti-cancer effect of targeted chemotherapy. Thus, the scope of the present disclosure extends beyond the exemplary NPB compounds disclosed.

A number of theories, hypotheses, beliefs and postulations are discussed herein. Such theories, hypotheses, beliefs and postulations are not intended to be binding or to limit the scope of the disclosure.

EXAMPLES

The examples set forth below are intended to illustrate but not limit the scope of the disclosure.

Example 1. Femtosecond Laser Spectroscopic Observation of the DET Reaction of Anti-Cancer Compounds (NPBS) with a Weakly-Bound Electron 1.1 fs-TRLS Method Femtosecond (fs) time-resolved laser spectroscopy (fs-TRLS) is the most versatile and powerful technique for real-time observation of molecular reactions. It uses laser flashes of such short duration that we are down to the time scale on which the reactions actually happen—femtoseconds (fs) (1 fs=$10^{-15}$ seconds). The DET reaction of a new NPB anti-cancer compound with a weakly-bound electron was studied by the fs-TRLS methodology, which was demonstrated previously [Lu, 2007; 2010]. For the latter, briefly our fs laser amplifier system (Spectra-Physics, Spitfire) produced laser pulses with a pulse width of 100-120 fs at a repetition rate of 500 Hz. A intense pump pulse at 350 nm was used to generate a weakly-bound electron ($e_{wb}^-$) by 2-photon excitation of a $H_2O$ molecule into a higher energy state $H_2O^*$ that then ionizes to produce an $e_{wb}^-$; a probe pulse at 400 nm coming at certain delay was used to monitor the DET reaction with the electron by detecting transient absorbance of the reaction intermediate anion state.

1.2 Results

A representative fs-TRLS observation of the DEA reaction of a new NPB anti-cancer compound (e.g., Compound B) is shown in FIG. 3. The results show that the DET reaction of compound B with $e_{wb}^-$ is highly effective, which is much stronger than that of bromodeoxyuridine (BrdU) or iododeoxyuridine (IdU). The latter does not have the electron-transfer promoter groups (diamino) and its DET reaction is observed to be negligible with the identical experimental conditions. This observation illustrates that the disclosed compounds are potent anti-cancer agents.

1.3 Discussion

The presence of (mono- or di-)halogen and diamino groups in the disclosed NPB compounds can indeed enhance their DET reactions with a weakly-bound electron that exists in the reductive intracellular environment of a cancer cell.

Example 2. In Vitro Tests on the Toxicity of NPBs in Treating Human Normal Cells 2.1 Materials & Methods 2.1.1 Chemicals and Reagents Cisplatin, dichloro-diamino-benzene (Compound A), bromo-diamino-benzene (Compound D), insulin, and 3-(4, 5-Dimethylthiazol-2-yl)-2,5-diphenyltetrazolium bromide (MTT) were obtained from Sigma-Aldrich. Dibromo-diamino-benzene (Dibromo-phenylenediamine, Compound B) was obtained from TCI-America. Diiodo-diaminobenzene (Compound C) was synthesized, purified and crystalized in our laboratory, and the structures and purity were examined by NMR and mass spectrometry. MEM and fetal bovine serum (FBS), penicillin G and streptomycin were obtained from Hyclone Laboratories (UT, USA). Stock solution of cisplatin was freshly prepared in ultrapure water or saline, and stock solutions of Compounds A, B, C, D were prepared in pure ethanol, where the final concentration of ethanol was ≤1% when treated to cells.

2.1.2 Cell Culture

A human skin diploid fibroblast (GM05757 cell line) was obtained from the Coriell Cell Repository directly. Fetal bovine serum (FBS) was obtained from Hyclone Laboratories (UT, USA). The GM05757 normal cells were cultivated with MEM (Hyclone) supplemented with 10% FBS, 100 units/mL penicillin G and 100 µg/mL streptomycin (Hyclone). The cells were maintained at 37° C. in a humidified atmosphere containing 5% $CO_2$.

2.1.3 Cell Viability Measurement by MTT

The toxic effects of NPBs on cell viability were determined by the 3-[4,5-dimethylthiazol-2-yl]-2,5-diphenyl tetrazoliumbromide (MTT) assay. Cells were cultured in 96-well plates ($5 \times 10^3$ cells/well) for 24 h. The culture medium was replaced by fresh culture medium and incubated for 72 or 96 h with varying drug concentrations. The MTT assay of cell viability was then conducted. Briefly, 100 µl new medium without phenol red containing 1.2 mM MTT (sigma) (i.e., adding 10 µl 12 mM MTT stock solution in PBS) were added to each well and incubated for 4 h. The medium was then removed, and the formazan crystals solubilized by 100 µL/well DMSO (or alternatively by 100 µl/well SDS and incubated for another 4 h). The surviving fraction was determined by measuring the absorbance at 540 nm (570 nm for SDS solubilization) using a Multiskan Spectrum UV/Vis microplate reader (Thermo Scientific), which is directly proportional to the number of viable cells.

2.2 Results

To test the toxicity of NPBs on human normal cells, the standard MTT assay was utilized and cisplatin was used as a reference. Human normal (GM05757) cells were treated with various drug concentrations (0-50 µM for cisplatin and 0-200 µM for compound A/B/C/D). The results are shown in FIGS. 4-8. First, it is clearly seen in FIG. 4 that cisplatin exhibits severe toxicity even at low concentrations of ≤30 µM with a measured IC50 of about 10 µM for the 72 hr treatment. This result confirms that cisplatin as an anti-cancer agent is indeed a highly toxic. In contrast, it is clearly demonstrated in FIGS. 5-8 that the present disclosed NPBs, Compounds A, B, C and D, have essentially no toxicity toward the normal cells even with the 96-hr treatment at very high concentration of 200 µM. These results demonstrate the contrast difference between the heavy-metal (Pt)-based chemotherapeutic drug (cisplatin) and NPBs. Thus, these NPB molecules are expected to induce no or minimal systematic toxic side effects in animals and humans.

2.3 Discussion

As the present inventor hypothesized, normal cells due to the lack of a reductive intracellular environment have a low reactivity to the disclosed compounds that are highly oxidizing. Therefore, the NPBs show no or low toxicity towards normal cells. The disclosed compounds are in contrast to the clinically used cisplatin which has a high affinity to human normal cells and is highly toxic. Thus, these NPBs have the potential to be excellent non-toxic anticancer agents.

Example 3. In Vitro Anti-Cancer Results of NPBs in Treating Various Cancer Cells

3.1 Materials & Methods

3.1.1 Chemicals and Reagents

Cisplatin, dichloro-diamino-benzene (Compound A), bromo-diamino-benzene (Compound D), insulin, and 3-(4,5-Dimethylthiazol-2-yl)-2,5-diphenyltetrazolium bromide (MTT) were obtained from Sigma-Aldrich. Dibromo-diamino-benzene (Dibromo-phenylenediamine, Compound B) was obtained from TCI—America. Diiodo-diaminobenzene (Compound C) was synthesized, purified and crystalized in our laboratory, and the structures and purity were examined by NMR and mass spectrometry. MEM and fetal bovine serum (FBS), penicillin G and streptomycin were obtained from Hyclone Laboratories (UT, USA). Stock solution of cisplatin was freshly prepared in ultrapure water or saline, and stock solutions of Compounds A, B, C, D were prepared in pure ethanol, where the final concentration of ethanol was ≤1% when treated to cells.

3.1.2 Cell Culture

A human skin diploid fibroblast (GM05757 cell line) was obtained from the Coriell Cell Repository directly, while the human cervical cancer cell line (HeLa, ATCC#: CCL-2; or ME-180), human breast cancer cell line (MDA-MB-231), human ovarian cancer cell line (NIH:OVCAR-3, ATCC#: HTB-161) and human lung cancer cell line (A549, ATCC#: CCL-185™), together with RPMI 1640, F-12K, McCoy's 5A and L-15 culture media, were obtained from the American Type Culture Collection (ATCC) directly. Fetal bovine serum (FBS) was obtained from Hyclone Laboratories (UT, USA). The GM05757 normal cells and HeLa cells were cultivated with MEM (Hyclone) supplemented with 10% FBS, 100 units/mL penicillin G and 100 µg/mL streptomycin (Hyclone). The complete growth media for ME-180, NIH:OVCAR-3, A549 and MDA-MB-231 cells were the ATCC-formulated McCoy's 5A Medium supplemented with 10% FBS, RPMI 1640 medium with 20%, F-12K medium with 10% FBS, and L-15 Medium (Leibovitz) with 10% FBS, respectively. The cells were maintained at 37° C. in a humidified atmosphere containing 5% $CO_2$.

3.1.3 Cell Viability Measurement by MTT

The anti-cancer effects of NPBs on cell viability were determined by the 3-[4,5-dimethylthiazol-2-yl]-2,5-diphenyl tetrazoliumbromide (MTT) assay. Cells were cultured in 96-well plates ($5 \times 10^3$ cells/well) for 24 h. The culture medium was replaced by fresh culture medium and incubated for 96 h with varying drug concentrations. The MTT assay of cell viability was then conducted. Briefly, 100 µl new medium without phenol red containing 1.2 mM MTT (sigma) (i.e., adding 10 µl 12 mM MTT stock solution in PBS) were added to each well and incubated for 4 h. The medium was then removed, and the formazan crystals solubilized by 100 µL/well DMSO (or alternatively by 100 µl/well SDS and incubated for another 4 h). The surviving fraction was determined by measuring the absorbance at 540 nm (570 nm for SDS solubilization) using a Multiskan Spectrum UV/Vis microplate reader (Thermo Scientific), which is directly proportional to the number of viable cells.

3.2 Results

The in vitro anti-cancer effects of NPBs were investigated in human cervical cancer (HeLa or ME-180), breast cancer (MDA-MB-231) and lung cancer (A549) cell lines, as well as the cisplatin-resistant human ovarian cancer (NIH:OVCAR-3, HTB-161) cell line. FIGS. 9-27 show cell survival rates of various human cancer cells after the treatment of a NPB with various concentrations for 96 hr. These results show that Compounds A, B, C and D killed cancer cells in a dose dependent manner, in striking contrast to the results for human normal cells (FIGS. 5-8). It is clearly seen that the cancer cells were effectively killed by the presence of NPBs. For example, nearly all cervical cancer cells (ME-180) and breast cancer cells (MDA-MB-231) were killed with the presence of about 200 µM Compound B or C or D, which showed no toxicity against human normal cells.

3.3 Discussion

The in vitro results presented herein demonstrate that the presence of a NPB (Compound A/B/C/D) effectively kills tumor cells but not normal cells, as shown in FIGS. 5-27. Thus, the NPBs are expected to have the significant anti-cancer efficacy of chemotherapy while inducing minimal or no toxic side effects in animals or humans.

Example 4. A NPB Compound (B) Induces DNA Double-Strand Breaks in Cancer Cells 4.1 Materials & Methods
  4.1.1 Chemicals and Reagents
  Ultrapure water for life science with a resistivity of >18.2 MΩ/cm and TOC <1 ppm obtained freshly from a Barnstead Nanopure water system was used. The γH2AX DNA damage assay kit was purchased from Invitrogen.
  4.1.2 The γH2AX DNA Damage Assay
  The γH2AX DNA damage assay (Invitrogen) was used to detect DSBs of genomic DNA in cancer cells. The phosphorylated H2AX foci are a biomarker of DNA DSB. DNA DSBs are measured by specific antibody-based detection of phosphorylated H2AX (γH2AX) in the nucleus. Briefly, the human cervical cancer (ME-180) cells were treated with different concentrations of compound B for 12 h under the cell culture conditions described above. Then following the detailed experimental procedures described in the Protocol provided by the manufacturer, we performed the HCS DNA Damage Assay of the treated cells. The images of cells were acquired with a Nikon Eclipse TS100 fluorescence microscope; quantitative analyses of activated γ-H2AX (DNA DBS yield) in the cells were performed using an Image J software.
  4.2. Results
  As shown in FIG. 28, the treatment of compound B induced a significant amount of DSBs in genomic DNA in cervical cancer cells.
  4.3. Discussion
  The result is particularly interesting, as DNA DSBs are well-known to be difficult for the cell to repair and thus potent inducers of cell death. This is consistent with what is observed for the cytotoxicity of the therapy of compound B, as shown in FIGS. 9-27, and is consistent with the proposed dissociative-electron-transfer (DET) mechanism for the NPB compound with weakly-bound electrons in cancer cells (FIGS. 2 and 3).

Example 5. Compound B Induces Significant Apoptosis in Human Cervical Cancer (ME-180) Cells 5.1 Materials & Methods
  5.1.1 Chemicals and Reagents
  The CellEvent™ Caspase-3/7 Green Detection Kit was purchased from Invitrogen.
  5.1.2 Cell Culture
  Human cervical cancer (ME-180) cells were purchased from the American Type Culture Collection (ATCC). Cells were cultivated with MEM (Hyclone) supplemented with 10% fetal bovine serum (Hyclone), 100 units/mL penicillin G and 100 μg/mL streptomycin (Hyclone). The cells were maintained at 37° C. in a humidified atmosphere containing 5% $CO_2$.
  5.1.3 Apoptosis Assays by Fluorescence Microscopy
  The CellEvent™ Caspase-3/7 Green Detection Kit (Invitrogen) was used for the detection of activated caspases and apoptotic cells following the vendor's protocol. This kit provides a fluorescent inhibitor of caspases (FLICA) specific for caspase-3 and -7; the cells show green fluorescence for activated caspase-3 and -7. The reagent consists of a four amino acid peptide (DEVD) conjugated to a nucleic acid binding dye. This cell-permeant substrate is intrinsically non-fluorescent, because the DEVD peptide inhibits the ability of the dye to bind to DNA. After activation of caspase-3 or caspase-7 in apoptotic cells, the DEVD peptide is cleaved, enabling the dye to bind to DNA and produce green fluorescence. Briefly, to use the CellEvent™ Caspase-3/7 Green Detection Reagent, add the substrate to the cells in complete growth medium, incubate for 30 minutes, and image. Apoptotic cells with activated caspase-3/7 show bright green nuclei, while cells without activated caspase 3/7 exhibit minimal fluorescence signal. This robust assay has been shown to be highly specific for caspase-3/7 activation and can be used to monitor caspase-3 or -7 activation with live-cell fluorescence imaging. Because the cleaved reagent labels nuclei of caspase 3/7-positive cells, this stain can also provide information on nuclear morphology, including condensed nuclei typical of late-stage apoptosis. ME-180 cells were grown to 60% confluence and then treated with 0-200 μM compound B for 48 h. The fluorescence was detected with a Nikon Eclipse TS100 microscope. Images were captured with an attached camera.
5.2 Results
  To test whether the NPB compound-mediated killing of cancer cells is due to induction of apoptosis, we used the CellEvent™ Caspase-3/7 Green Detection Kit. The results in FIG. 29 show that the treatment of Compound B resulted in a significant activation of caspase-3 and -7, which was evident from a significant enhancement in green fluorescence. Moreover, compound B also caused significant changes on nuclear morphology, showing condensed nuclei in the treated cancer cells, which is typical of late-stage apoptosis. These results indicate a significant induction of apoptosis when the cells were treated with 0-200 μM Compound B.
5.3 Discussion
  The cytotoxicity effect of compound B was correlated with the increase in the amount of activated caspases 3/7 exhibited by the treated cells. These results indicate that compound B resulted in a significant increase in apoptosis of the treated cancer cells. This is consistent with the results of compound B induced DNA DSBs, as shown in FIG. 28.

Example 6. In Vivo Test of Compound B in the Xenograft Mouse Model of Human Cervical Cancer (ME-180) in Female SCID Mice 6.1 Materials and Protocol
  6.1.1 Study Groups
  The two groups in the experiment were: (1) control article (5% EtOH/medium); (2) Compound B at 7 mg/kg in 5% EtOH/medium daily for 5 days, as shown in Table 1.

TABLE 1

Study Groups in Example 6

| Group # | Group Name | No. mice | Drug Dose | Admin. Route | Volume (μL/20 g) | Schedule |
|---|---|---|---|---|---|---|
| 1 | Control | 5 | N/A | i.p. | 200 | Daily for 5 days |
| 2 | Compound B | 5 | 7 mg/kg | i.p. | 200 | daily for 5 days |

6.1.2 Mouse and Compound B Solution Preparation:
  6-8 week SCID mice were used in this study; Compound B as an exemplary NPB was dissolved in 5% EtOH: 95% cell culture medium (≈1:20).
  6.1.3. Cell Preparation (For s.c. Injection):
  ME-180 (human cervical cancer) cells were cultured in the ATCC-formulated McCoy's 5A Medium supplemented with 10% FBS. The cells in a flask were maintained at 37°

C. in a humidified atmosphere containing 5% $CO_2$. The cells were rinsed with PBS, trypsined for detachment from the bottom of the flask, mixed with fresh growth medium, and centrifuged to remove the supernatant. The cells were re-suspend with fresh medium to appropriate concentration for s.c. injection into the mice. Injection volume was 50 µl ($1.5 \times 10^6$ cells) per animal.

6.1.4 Xenograft Cervical Cancer Model by S.C.

ME-180 tumour cells were subcutaneously into female SCID mice (age 6-8 weeks) in a volume of 50 µL into the left flank using a 27-gauge needle. This was established as a subcutaneous (SC) xenograft mouse model of human cervical cancer.

6.1.5 Drug Dose Administration

Mice were individually weighed and injected intraperitoneally according to body weight for an injection concentration as outlined in the study group table above. The injection volume was based on 200 µL per 20 g mouse. The skin surface was wiped down with 70% isopropyl alcohol to clean the injection site.

6.1.6 Data Collection

Tumor size was measured as a function of time to assess tumor growth delay associated with treatment using slide caliper. Animals were also weighed at the time of tumour measurement. Tumours in mice were allowed to grow to a maximum of 1000 mm³ before termination.

6.1.7 Evaluation of Drug Induced Stress in the Mice

All animals were observed post administration, and at least once a day, more if deemed necessary, during the pre-treatment and treatment periods for mortality and morbidity. In particular, animals were monitored for signs of ill health such as body weight loss, change in appetite, behaviour changes such as altered gait, lethargy and gross manifestations of stress.

6.2 Results

Figure 30:
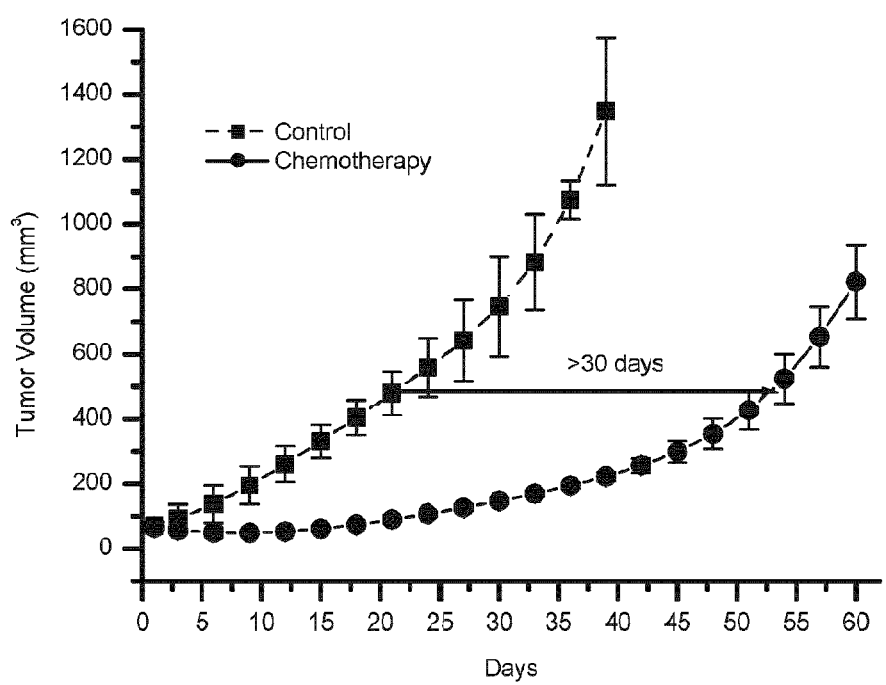
FIG. 30 shows tumor growth delays in the mouse xenograft cervical (ME-180) cancer model. Compound B at 7 mg/kg daily for 5 days was administered by IP injection into the mice. Tumor growth delays were measured between the times as the tumors reached 500 mm³ for the control group and the treated group. A growth delay of over 30 days was observed between the control and the chemotherapy group, indicative of a high drug efficacy.
Figure 30:
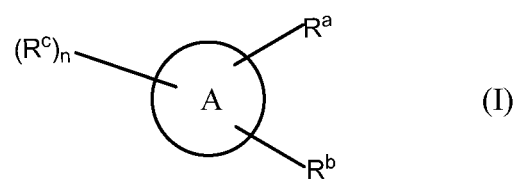

The in vivo anticancer effects of Compound B as an exemplary NPB compound were investigated in the xenograft mouse tumor model of human cervical cancer (ME-180). As shown in FIG. 30, it is clearly seen the administration of Compound B alone significantly suppressed tumor growth, compared with the control group with no treatment in the tumor model. The results also show that compound B resulted in a significant tumor regrowth delay of more than 30 days in vivo.

6.3 Discussion

Given that only a small dose (7 mg/kg, equivalent to 50 µM in mice) of compound B daily for 5 days used in the present experiment and that Compound B has the observed no or minimal overall and acute toxicity at higher doses (200 µM in vitro), it is reasonably expected that these results can be extrapolated to larger doses or more frequent treatments so that a maximal therapeutic effect could be achieved.

Example 7. In Vivo Test on the Toxicity of Compound B in SCID Mice 7.1 Materials and Protocol 7.1.1 Study Groups The two groups (five 6-8 week SCID mice/group) in the experiment were: (1) control article (in 5% EtOH/medium); and (2) Compound B 7 mg/kg in 5% EtOH/medium, as shown in Table 2. Compound B was injected IP every day for 5 days.

TABLE 2

Study Groups in Example 7

| Group # | Group Name | No. mice | TA/CA* Dose (mg/kg) | Admin. Route | Volume (µL/ 20 g) | Schedule (Days) |
| --- | --- | --- | --- | --- | --- | --- |
| 1 | Control | 5 | N/A | i.p. | 200 | Daily for 5 days |
| 2 | Compound B | 5 | 7 | i.p. | 200 | Daily for 5 days |

*TA: Test Article; CA: Control Article 7.1.2 Mouse and Compound B Solution Preparation:

6-8 week SCID mice were used in this study; Compound B as an exemplary NPB was dissolved in 5% EtOH: 95% cell culture medium (1:20).

7.1.3 Dose Administration 6-8 week SCID Mice were individually weighed and injected intraperitoneally (IP) according to body weight for an injection concentration as outlined in the study group table above. Compound B was administered by IP injection into mice at 0, and 7 mg/kg daily for 5 days. The injection volume was based on 200 µL per 20 g mouse. The skin surface was wiped down with 70% isopropyl alcohol to clean the injection site.

7.1.4 Data Collection and Analysis

The overall drug toxicity in mice was observed by a survival assay and body weight measurements, and the acute drug toxicity was measured by blood collection and histology. The hepatotoxicity (ALT, ALP, total bilirubin), nephrotoxicity (blood urea, creatinine), and electrolytes (Na, K, Cl) were analyzed by biochemical methods or HPLC-mass spectroscopy. Mice were observed for any physical toxicity. Blood samples were collected from the saphenous vein at various time points after drug injection. At the end of the study, whole organs were harvested in order to assess liver, and kidney toxicity.

7.1.5 Evaluation of Drug Induced Stress in the Mice

All animals were observed post administration, and at least once a day, more if deemed necessary, during the pre-treatment and treatment periods for mortality and morbidity. In particular, animals were monitored for signs of ill health such as body weight loss, change in appetite, behavior changes such as altered gait, lethargy and gross manifestations of stress.

7.2 Results

The overall drug toxicity was studied in 6-8 week SCID mice through a survival assay and body weight measurements, and the acute drug toxicity was studied by measurements of the hepatotoxicity (ALT, ALP, total bilirubin), nephrotoxicity (blood urea, creatinine), and electrolytes (Na, K, Cl). As shown in FIG. 31, Compound B showed no effect on the weight of mice with time, exhibiting no physical toxicity. Interestingly, it is also clearly shown in FIG. 32 that Compound B even given at a high dose (5 day×7 mg/kg/day=35 mg/kg), which is approximately 5 times the dose of cisplatin used in mouse experiments and humans, induced no observable acute toxicity, i.e., no hepatotoxicity, no nephrotoxicity, and no changes in electrolytes in mice.

7.3 Discussion

The in vivo results presented in FIGS. 30-32 have clearly demonstrated that Compound B exhibits a significant anti-cancer effect while inducing no or minimal toxicity in mice, no overall drug toxicity (no effects on mouse survival and body weight) and no acute toxicity (no hepatotoxicity, no nephrotoxicity, and no changes in electrolytes). These results are in excellent agreement with the in vitro results observed in human normal cells (shown in FIGS. 5-8) and human cancer cells (FIGS. 9-29). It is therefore demonstrated that Compound B as a NPB is a non-toxic and effective anticancer agent.

No signs of toxicity or ill health, neither overall drug toxicity (no effects on mouse survival and body weight), nor acute toxicity (no hepatotoxicity, no nephrotoxicity, and no changes in electrolytes), were noted in any of the animals treated.

The references cited herein are incorporated by reference in their entirety.

The above-described embodiments are intended to be examples only. Alterations, modifications and variations can be effected to the particular embodiments by those of skill in the art without departing from the scope of the disclosure, which is defined solely by the claims appended hereto.

REFERENCES

1. WO/2014/094178, "RADIOSENSITIZER COMPOUNDS FOR USE IN COMBINATION WITH RADIATION" (to Q.-B. Lu; Published on Jun. 26, 2014).
2. P. G. Rose, B. N. Bundy, E. B. Watkins, J. T. Thigpen, G. Deppe, M. A. Maiman, D. L. Clarke-Pearson, S. Insalaco. Concurrent cisplatin-based radiotherapy and chemotherapy for locally advanced cervical cancer. N. Engl. J. Med. 340, 1144-53 (1999).
3. D. M. Reese, Anticancer drugs, Nature 378, 532(1995).
4. H. Varmus, The New Era in Cancer Research. Science 312, 1162(2006).
5. B. Alberts, The Promise of Cancer Research, Science 320, 19(2008); The Challenge of Cancer. Science 331, 1491 (2011).
6. A. H. Zewail, Femtochemistry: Atomic-Scale Dynamics of the Chemical bond using ultrafast lasers (Nobel Lecture). Angew. Chem. Int. Ed. 39, 2587-2631 (2000).
7. Q.-B. Lu, Effects of Ultrashort-Lived Prehydrated Electrons in Radiation Biology and Their Applications for Radiotherapy of Cancer. Mutat. Res.: Rev. Mutat. Res. 704, 190-199 (2010).
8. L. Y. Lu, N. Ou, & Q.-B. Lu, Antioxidant Induces DNA Damage, Cell Death and Mutagenicity in Human Lung and Skin Normal Cells. Sci. Rep. 3, 3169(1-11) (2013)
9. Q.-B. Lu, Molecular Reaction Mechanisms of Combination Treatments of Low-Dose Cisplatin with Radiotherapy and Photodynamic Therapy, J. Med. Chem. 50, 2601-2604 (2007).
10. Q.-B. Lu, S. Kalantari, & C.-R. Wang, Electron Transfer Reaction Mechanism of Cisplatin with DNA at the Molecular Level. Mol. Pharmaceutics 4, 624-628 (2007).
11. M. D. Prados et al. "A phase 3 randomized study of radiotherapy plus procarbazine, CCNU, and vincristine (PCV) with or without BUdR for the treatment of anaplastic astrocytoma: a preliminary report of RTOG 9404", Int. J. Radiat. Oncol. Biol. Phys. 45, 1109(1999).
12. A. Choudhury et al., Targeting homologous recombination using imatinib results in enhanced tumor cell chemosensitivity and radiosensitivity, Mol Cancer Ther 8, 203-2013 (2009).

The invention claimed is:

1. A method of treating a cancer, comprising administering to a subject in need thereof a therapeutically effective amount of a non-platinum-based (NPB) compound, having the general formula III:

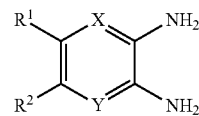

(III)

wherein:

X and Y are independently C—$R^3$ or N;

$R^1$ is a halogen selected from the group of Cl, Br, I or F;

one of $R^2$ and $R^3$ is H, OH, halogen, alkyl, alkoxy, alkenyl, alkynyl, cycloalkyl, cycloalkenyl, cycloalkynyl, aryl, heterocyclyl, or heteroaryl, and the other of $R^2$ and $R^3$ is H or halogen;

wherein each of the alkyl, alkoxy, alkenyl, alkynyl, cycloalkyl, cycloalkenyl, cycloalkynyl, aryl, heterocyclyl and heteroaryl moieties is optionally substituted by one or more functional groups selected from the list consisting of hydroxyl, amino, amido, cyano, nitro, carboxyl, ester, ether, ketone, aldehyde, or a combination thereof;

or a pharmaceutically acceptable salt thereof;

wherein the cancer is selected from a group consisting of: testicular cancer, bladder cancer, cervical cancer, ovarian cancer, breast cancer, prostate cancer, head and neck cancer, lung cancer, pancreatic cancer, stomach cancer, colorectal cancer, liver cancer, esophageal cancer, and brain cancer.

2. The method of claim 1, wherein at least one of X and Y are C—$R^3$ and $R^3$ is H.

3. The method of claim 1, wherein the compound is selected from the group consisting of:

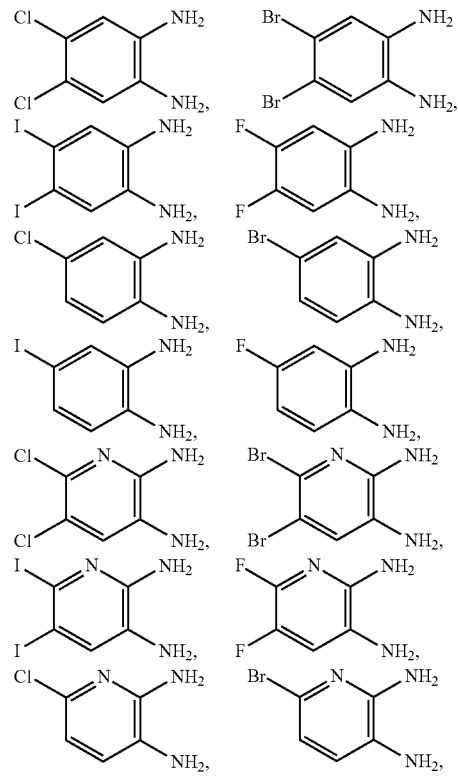

-continued

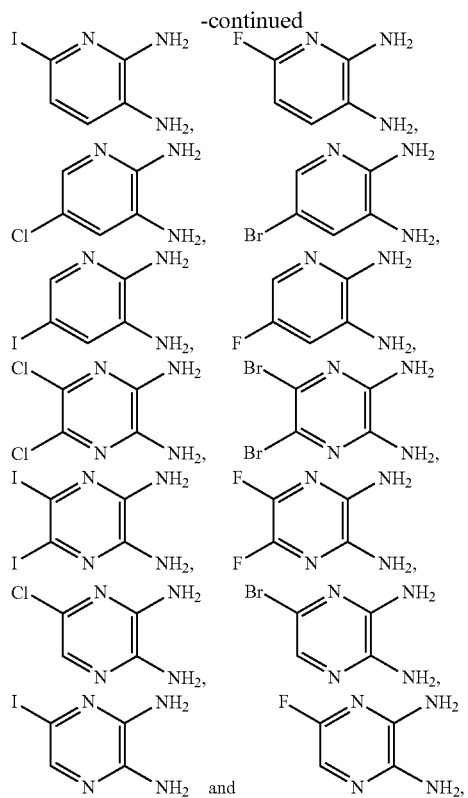

or
a pharmaceutically acceptable salt thereof.

4. The method of claim 2, wherein both of X and Y are C—R³ and R³ is H.

5. The method of claim 3, wherein the compound is selected from the group consisting of:

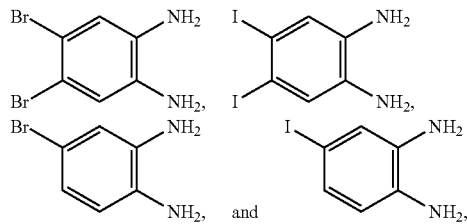

or a pharmaceutically acceptable salt thereof.

6. A method of treating myeloma or lymphoma treatable by cisplatin, the method comprising administering a conditioning regimen to a subject in need thereof, prior to a bone marrow transplant or hematopoietic stem cell transplant, wherein the conditioning regimen is comprised of a therapeutically effective amount of the compound having the general formula III:

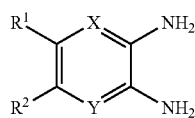

(III)

wherein:
X and Y are independently C—R³ or N;
R¹ is a halogen selected from the group of Cl, Br, I or F;
one of R² and R³ is H, OH, halogen, alkyl, alkoxy, alkenyl, alkynyl, cycloalkyl, cycloalkenyl, cycloalkynyl, aryl, heterocyclyl, or heteroaryl, and the other of R² and R³ is H or halogen;
wherein each of the alkyl, alkoxy, alkenyl, alkynyl, cycloalkyl, cycloalkenyl, cycloalkynyl, aryl, heterocyclyl and heteroaryl moieties is optionally substituted by one or more functional groups selected from the list consisting of hydroxyl, amino, amido, cyano, nitro, carboxyl, ester, ether, ketone, aldehyde, or a combination thereof;
or a pharmaceutically acceptable salt thereof;
and one or more pharmaceutically acceptable carriers or diluents.

7. The method of claim 1, wherein the therapeutically effective amount of the compound is administered with one or more pharmaceutically acceptable carriers or diluents.

8. A method of treating a non-cancer disease or condition selected from the group consisting of: psoriasis, Crohn's disease, psoriatic arthritis, rheumatoid arthritis, multiple sclerosis and lupus erythematosus, comprising administering to a subject in need thereof a therapeutically effective amount of a non-platinum-based (NPB) compound, wherein the compound is selected from the group consisting of:

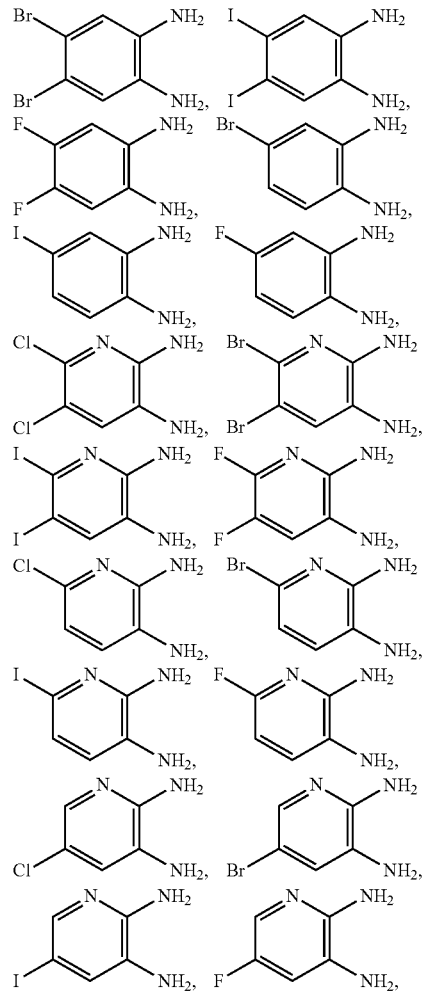

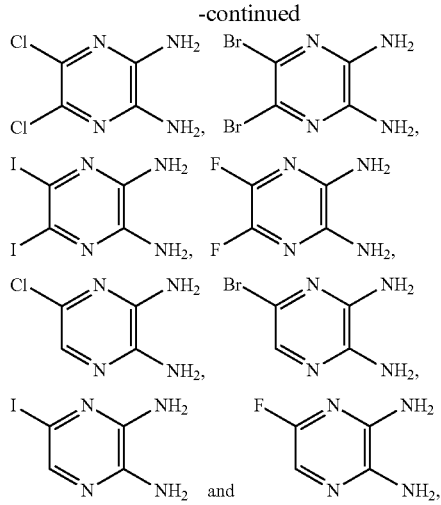

or a pharmaceutically acceptable salt thereof.

9. The method of claim 6, wherein the compound is selected from the group consisting of:

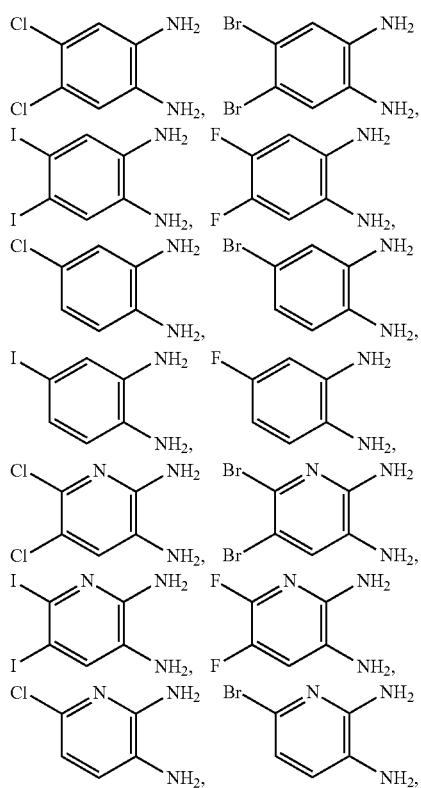

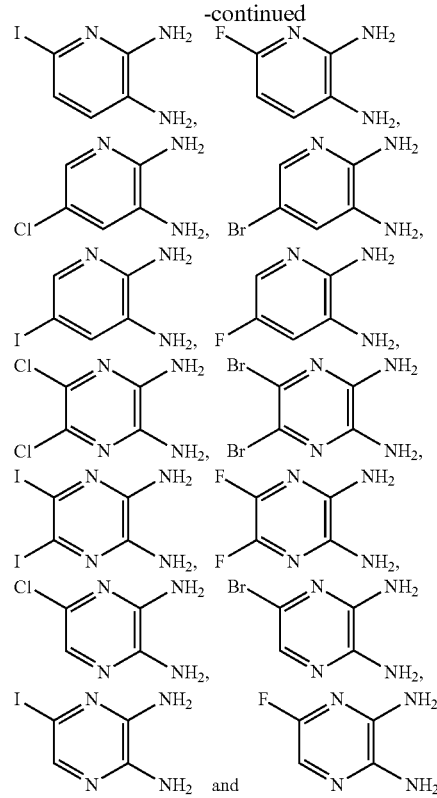

or a pharmaceutically acceptable salt thereof.

10. The method of claim 3, wherein the compound is administered alone or in conjunction with one or more additional chemotherapeutic agents or cancer therapies, excluding radiation.

11. The method of claim 5, wherein the compound is administered alone or in conjunction with one or more additional chemotherapeutic agents or cancer therapies, excluding radiation.

12. The method of claim 1, wherein the cancer is selected from the group consisting of: ovarian cancer, cervical cancer, breast cancer, lung cancer, head and neck cancer, and pancreatic cancer.

13. The method of claim 3, wherein the cancer is selected from the group consisting of: ovarian cancer, cervical cancer, breast cancer, lung cancer, head and neck cancer, and pancreatic cancer.

14. The method of claim 5, wherein the cancer is selected from the group consisting of: ovarian cancer, cervical cancer, breast cancer, lung cancer, head and neck cancer, and pancreatic cancer.

15. The method of claim 1, wherein the compound is administered alone or in conjunction with one or more additional chemotherapeutic agents or cancer therapies, excluding radiation.

* * * * *